United States Patent [19]

Narita et al.

[11] Patent Number: 4,698,352

[45] Date of Patent: Oct. 6, 1987

[54] 4-OXO-1,4-DIHYDRONICOTINIC ACID DERIVATIVES, SALTS THEREOF, AND ANTIBACTERIAL AGENTS CONTAINING THE SAME

[75] Inventors: Hirokazu Narita, Toyama; Yoshinori Konishi, Takaoka; Jun Nitta, Namekawa; Shunjiro Misumi, Chofu; Hideyoshi Nagaki, Toyama; Isao Kitayama, Toyama; Yoriko Nagai, Toyama; Yasuo Watanabe, Toyama; Nobuyuki Matsubara, Toyama; Shinzaburo Minami, Toyama; Isamu Saikawa, Toyama, all of Japan

[73] Assignee: Toyama Chemical Co., Ltd., Tokyo, Japan

[21] Appl. No.: 546,165

[22] Filed: Oct. 27, 1983

[30] Foreign Application Priority Data

Oct. 29, 1982 [JP] Japan .............................. 57-188930
Oct. 24, 1983 [JP] Japan .............................. 58-197624

[51] Int. Cl.$^4$ .................. A61K 31/455; C07D 213/80; C07D 401/02; C07D 405/02

[52] U.S. Cl. .................................. 514/339; 546/117; 546/122; 546/140; 546/144; 546/147; 546/153; 546/167; 546/193; 546/194; 546/256; 546/257; 546/258; 546/268; 546/269; 546/270; 546/271; 546/272; 546/273; 546/274; 546/275; 546/276; 546/277; 546/278; 546/279; 546/280; 546/281; 546/283; 546/284; 546/298; 544/105; 544/112; 544/113; 544/114; 544/116; 514/335; 544/118; 544/120; 544/122; 544/128; 544/129; 544/182; 544/216; 544/236; 544/237; 544/238; 544/257; 544/264; 544/278; 544/284; 544/333; 544/353; 544/365; 544/405; 514/236; 514/241; 514/242; 514/248; 514/249; 514/252; 514/253; 514/254; 514/256; 514/258; 514/259; 514/261; 514/307; 514/308; 514/314; 514/316; 514/318; 514/333; 514/334; 514/336; 514/337; 514/340; 514/341; 514/342; 514/343; 514/350

[58] Field of Search ............... 546/298, 284, 193, 283, 546/194, 281, 268, 278, 153, 279, 274, 280, 269, 275, 270, 277, 273, 276, 272, 256, 271, 257, 167, 258, 140, 122, 147, 117, 144; 424/266; 544/405, 237, 278, 333, 353, 112, 238, 284, 113, 365, 235, 114, 182, 257, 115, 216, 105, 117, 264, 236, 120, 122, 128, 129; 514/350, 254, 316, 340, 236, 259, 318, 341, 242, 261, 333, 342, 241, 258, 334, 343, 248, 256, 335, 249, 307, 336, 252, 308, 337, 253, 314, 339

[56] References Cited

U.S. PATENT DOCUMENTS 4,115,101 9/1978 Carlson ............................ 546/298

FOREIGN PATENT DOCUMENTS 2901868 7/1979 Fed. Rep. of Germany ...... 424/266

OTHER PUBLICATIONS

Chemical Abstracts 93:46426s.

*Primary Examiner*—Henry R. Jiles
*Assistant Examiner*—Dale A. Bjorkman
*Attorney, Agent, or Firm*—Oblon, Fisher, Spivak, McClelland & Maier

[57] ABSTRACT

This invention relates to a novel 4-oxo-1,4-dihydronicotinic acid derivative

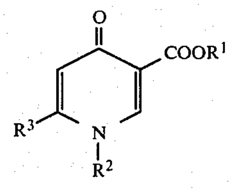

or a salt thereof, wherein $R^1$ is hydrogen or carboxyl-protecting group;

$R^2$ is substituted phenyl and naphthyl, or a substituted or unsubstituted heterocyclic group; and $R^3$ is haloalkyl, aminoalkyl, or substituted or unsubstituted alkenyl, phenylalkenyl, naphthylalkenyl, phenylalkyl, naphthylalkyl, phenylalkynyl, naphthylalkynyl, heterocyclic alkyl, heterocyclic alkenyl, phenyl, naphthyl, cycloalkyl, cycloalkenyl, carboxylic acyl, iminoalkyl, heterocyclic or bridged hydrocarbon, which has a broad antibacterial spectrum and a low toxicity, and are useful for treatment of diseases of human beings and animals, to a process for producing the same and to an antibacterial agent containing the same.

13 Claims, No Drawings

4-OXO-1,4-DIHYDRONICOTINIC ACID DERIVATIVES, SALTS THEREOF, AND ANTIBACTERIAL AGENTS CONTAINING THE SAME

BACKGROUND OF THE INVENTION

Field of the Invention

This invention relates to a novel 4-oxo-1,4-dihydronicotinic acid derivative and its salt, a process for producing the same, and an antibacterial agent containing the same.

SUMMARY OF THE INVENTION

The inventors of this invention have conducted extensive research to find a compound having a broad antibacterial spectrum, namely an excellent antibacterial activity against Gram-positive and Gram-negative bacteria, having low toxicity in mammals, giving a high blood level when administered orally or parenterally, and exhibiting a high effect on the treatment of diseases of human beings and animals. As a result, it has been found that a 4-oxo-1,4-dihydronicotinic acid derivative or its salt being substantially different in chemical structure from the various commercially available antibacterial agents, have the above-mentioned properties.

This invention provides a novel antibacterial compound having a broad antibacterial spectrum and a process for producing the same.

This invention also provides an antibacterial compound having low toxicity.

A further object of this invention is to provide an antibacterial compound which can be well absorbed orally or parenterally.

This invention further provides an antibacterial compound having an excellent effect on the treatment of diseases of human beings and animals.

Other objects and advantages of this invention will become apparent from the following description.

According to this invention, there is provided a 4-oxo-1,4-dihydronicotinic acid derivative and its salt, said derivative being represented by the formula (I),

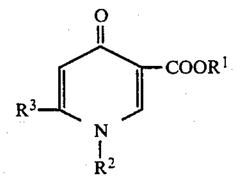

(I)

wherein $R^1$ represents a hydrogen atom or a carboxyl-protecting group; $R^2$ represents a substituted aryl group or a substituted or unsubstituted heterocyclic group; and $R^3$ represents a haloalkyl group, an aminoalkyl group or a substituted or unsubstituted alkenyl, aralkenyl, aralkyl, aralkadienyl, aralkynyl, heterocyclic alkyl, heterocyclic alkenyl, aryl, cycloalkyl, cycloalkenyl, acyl, iminoalkyl, heterocyclic or bridged hydrocarbon group, a process for producing the same, and an antibacterial agent containing the same.

In the formulas described herein, $R^1$ is a hydrogen atom or a carboxyl-protecting group. The carboxyl-protecting groups are available and include ester-forming groups which can be removed by catalytic reduction, chemical reduction or other treatments under mild conditions; ester-forming groups which can easily be removed in living bodies; and other known ester-forming groups which can easily be removed by treatment with water or an alcohol. such as organic silyl-containing groups, organic phosphorus-containing groups, organic tin-containing groups, or the like.

Examples of typical carboxyl-protecting groups are:

(a) alkyl groups, for example, $C_{1-4}$ alkyl;

(b) substituted lower alkyl groups, at least one of the substituents of which is halogen, nitro, acyl, alkoxy, oxo, cyano, hydroxyl, di—$C_{1-4}$ alkylamino, cycloalkyl, aryl, alkylthio, alkylsulfinyl, alkylsulfonyl, alkoxycarbonyl, 5-alkyl-2-oxo-1,3-dioxol-4-yl, 1-indanyl, 2-indanyl, furyl, pyridyl, 4-imidazolyl, phthalimido, succinimido, azetidino, aziridino, pyrrolidino, piperidino, morpholino, thiomorpholino, pyrrolyl, pyrazolyl, thiazolyl, isothiazolyl, oxazolyl, isoxazolyl, thiadiazolyl, oxadiazolyl, thiatriazolyl, oxatriazolyl, triazolyl, tetrazolyl, quinolyl, phenazinyl, benzofuryl, benzothienyl, benzoxazolyl, benzothiazolyl, coumarinyl, N-lower alkylpiperazino, 2,5-dimethylpyrrolidino, 1,4,5,6-tetrahydropyrimidinyl, 4-methylpiperidino, 2,6-dimethylpiperidino, 4-(5-methyl-2-pyrrolinyl), 4-(2-pyrrolinyl), N-methylpiperidinyl, 1,3-benzodioxolanyl, alkylamino, dialkylamino, acyloxy, acylamino, acylthio, dialkylaminocarbonyl, alkoxycarbonylamino, alkenyloxy, aryloxy, aralkyloxy, alicycle-oxy, heterocycle-oxy, alkoxycarbonyloxy, alkenyloxycarbonyloxy, aryloxycarbonyloxy, aralkyloxycarbonyloxy, alicycleoxycarbonyloxy, heterocycle-oxycarbonyloxy, alkenyloxycarbonyl, aryloxycarbonyl, aralkyloxycarbonyl, alicycleoxycarbonyl, heterocycle-oxycarbonyl, alkylanilino or alkylanilino substituted by halogen, lower alkyl, or lower alkoxy;

(c) cycloalkyl groups, lower-alkyl-substituted cycloalkyl groups, or [2,2-di(lower alkyl)-1,3-dioxolan-4-yl]methyl groups;

(d) alkenyl groups;

(e) alkynyl groups;

(f) phenyl group, substituted phenyl groups, at least one of the substituents of which is selected from the substituents exemplified in above (b); or aryl groups represented by the formula:

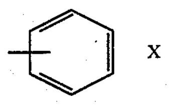

wherein —X— is —CH═CH—O—, —CH═CH—S—, —$CH_2CH_2S$—, —CH═N—CH═N—, —CH═CH—CH═CH—, —CO—CH═CH—CO—, or —CO—CO—CH═CH—, or substituted derivatives thereof, the substituents of which are selected from those exemplified in above (b), or the formula:

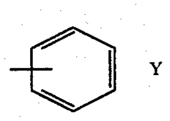

wherein —Y— is a lower alkylene group such as —$(CH_2)_3$— and —$(CH_2)_4$—, or substituted derivatives thereof, the substituents of which are selected from those exemplified in above (b);

(g) aralkyl groups which may be substituted, at least one of the substituents of which is selected from those exemplified in above (b);

(h) heterocyclic groups which may be substituted, at least one of the substituents of which is selected from those exemplified in above (b);

(i) alicyclic indanyl or phthalidyl groups or substituted derivatives thereof, the substituent of which is halogen or methyl; alicyclic tetrahydronaphthyl groups, or substituted derivatives thereof, the substituent of which is halogen or methyl; trityl group, cholesteryl group, or bicyclo[4,4,0]-decyl group;

(j) alicyclic phthalidylidene-lower alkyl group or substituted derivatives thereof, the substituent of which is halogen or lower alkyl group.

The carboxyl-protecting groups listed above are typical examples, and there may be used any groups selected from those disclosed in U.S. Pat. Nos. 3,499,909; 3,573,296; and 3,641,018, West German Offenlegungsschrift Nos. 2,301,014; 2,253,287; and 2,337,105.

Among them, preferable carboxyl-protecting groups are those which can readily be removed in living bodies such as 5-lower alkyl-2-oxo-1,3-dioxol-4-yl-lower alkyl groups, acyloxyalkyl groups, acylthioalkyl groups, phthalidyl group, indanyl group, phenyl group, substituted or unsubstituted phthalidylidene-lower alkyl groups or groups represented by the formulas:

$$-\underset{R^5}{\underset{|}{C}}H(CH_2)_mOR^4,\ -\underset{R^5}{\underset{|}{C}}HOCOOR^6 \text{ and } -\underset{R^7}{\underset{|}{C}}H(CH_2)_mCOOR^4$$

wherein $R^4$ represents a hydrogen atom or a straight or branched chain substituted or unsubstituted alkyl, alkenyl, aryl, aralkyl, alicyclic, or heterocyclic group; $R^5$ represents a hydrogen atom or an alkyl group; $R^6$ represents a straight or branched chain substituted or unsubstituted alkyl, alkenyl, aryl, aralkyl, alicyclic, or heterocyclic group; $R^7$ represents a hydrogen atom, a halogen atom or a substituted or unsubstituted alkyl, cycloalkyl, aryl or heterocyclic group or $-(CH_2)_n-COOR^4$ wherein $R^4$ is as defined above and n represents 0, 1 or 2, and m represents 0, 1 or 2.

The above-mentioned preferable carboxyl-protecting groups include specifically 5-lower alkyl-2-oxo-1,3-dioxol-4-yl-lower alkyl groups such as 5-methyl-2-oxo-1,3-dioxol-4-ylmethyl, 5-ethyl-2-oxo-1,3-dioxol-4-ylmethyl, 5-propyl-2-oxo-1,3-dioxol-4-ylmethyl, and the like; acyloxyalkyl groups, such as acetoxymethyl, pivaloyloxymethyl, propionyloxymethyl, butyryloxymethyl, isobutyryloxymethyl, valeryloxymethyl, 1-acetoxy-ethyl, 1-acetoxy-n-propyl, 1-pivaloyloxy-ethyl, 1-pivaloyloxy-n-propyl and the like; acylthioalkyl groups such as acetylthiomethyl, pivaloylthiomethyl, benzoylthiomethyl, p-chlorobenzoylthiomethyl, 1-acetylthio-ethyl, 1-pivaloylthio-ethyl, 1-benzoylthioethyl, 1-(p-chlorobenzoylthio)-ethyl and the like; alkoxymethyl groups such as methoxymethyl, ethoxymethyl, propoxymethyl, isopropoxymethyl, butyloxymethyl and the like; alkoxycarbonyloxylower alkyl groups such as methoxycarbonyloxymethyl, ethoxycarbonyloxymethyl, propoxycarbonyloxymethyl, isopropoxycarbonyloxymethyl, n-butyloxycarbonyloxymethyl, tert.-butyloxycarbonyloxymethyl, 1-methoxycarbonyloxyethyl, 1-ethoxycarbonyloxyethyl, 1-propoxycarbonyloxyethyl, 1-isopropoxycarbonyloxyethyl, 1-butyloxycarbonyloxyethyl and the like; alkoxycarbonylalkyl groups such as methoxycarbonylmethyl, ethoxycarbonylmethyl and the like; phthalidyl group; indanyl group; phenyl group; and phthalidylidenealkyl groups such as 2-(phthalidylidene)-ethyl, 2-(5-fluorophthalidylidene)-ethyl, 2-(6-chlorophthalidylidene)-ethyl, 2-(6-methoxyphthalidylidene)-ethyl and the like.

In respect of $R^2$ and $R^3$ in the formula [I], the aryl group includes, for example, phenyl, naphthyl and the like, and the heterocyclic group includes 5membered, 6-membered and fused ring type heterocyclic groups having at least one atom selected from N, S and O such as, thienyl, furyl, pyrrolyl, imidazolyl, pyrazolyl, thiazolyl, isothiazolyl, oxazolyl, isoxazolyl, furazanyl, pyrrolidinyl, pyrrolinyl, imidazolidinyl, imidazolinyl, pyrazolidinyl, pyrazolinyl, oxadiazolyl, thiadiazolyl, triazolyl, tetrazolyl, thiatriazolyl, pyridyl, pyrazinyl, pyrimidinyl, pyridazinyl, piperidinyl, piperazinyl, pyranyl, morpholinyl, pyridine-1-oxide-3- or 4-yl, pyridazine-1-oxide-6-yl, quinoline-1-oxide-6-yl, triazinyl, benzothienyl, naphthothienyl, benzofuryl, 2,3-dihydrobenzofuryl, benzothiazolyl, isobenzofuryl, chromenyl, indolidinyl, isoindolyl, indolyl, indazolyl, purinyl, quinolyl, 1,2,3,4-tetrahydroquinolyl, 1,2-dihydroquinolyl, isoquinolyl, phthalazinyl, naphthyridinyl, quinoxalinyl, 1,2,3,4-tetrahydroquinoxalinyl, quinazolinyl, cinnolinyl, pteridinyl, isochromanyl, chromanyl, indolinyl, isoindolinyl, benzoxazolyl, benzomorpholinyl, triazolopyridyl, tetrazolopyridazinyl, tetrazolopyrimidinyl, thiazolopyridazinyl, thiadiazolopyridazinyl, triazolopyridazinyl and the like. Furthermore, the haloalkyl group in $R^3$ includes halo-$C_{1-8}$alkyl groups, for example, fluoromethyl, chloromethyl, bromomethyl, 1- or 2-fluoroethyl, 1- or 2-bromoethyl, 1- or 2-chloroethyl and the like. The aminoalkyl group in $R^3$ includes amino—$C_{1-8}$alkyl groups, for example, aminomethyl, 1-aminoethyl, 2-aminoethyl, and the like. The alkenyl group in $R^3$ includes $C_{2-8}$alkenyl groups, for example, vinyl, allyl, isopropenyl, 1-propenyl, 2-butenyl, 2-pentenyl and the like. The aralkenyl group in $R^3$ includes the above-mentioned alkenyl groups which have been substituted by the above-mentioned aryl group. The aralkyl group in $R^3$ includes $C_{1-8}$alkyl groups such as methyl, ethyl, n-propyl, isopropyl, n-butyl, isobutyl, sec.-butyl, tert.-butyl, pentyl, hexyl, octyl and the like which have been substituted by the above-mentioned aryl group. The aralkadienyl group in $R^3$ includes $C_{4-8}$—alkadienyl groups such as 1,3-butadienyl, 2,4-pentadienyl and the like which have been substituted by the above-mentioned aryl group. The aralkynyl group in $R^3$ includes $C_{2-8}$alkynyl groups such as ethynyl, 1-propynyl, 2-propynyl and the like which have been substituted by the above-mentioned aryl group. The heterocyclic alkenyl group in $R^3$ includes the above-mentioned $C_{2-8}$alkenyl groups which have been substituted by the above-mentioned heterocyclic group. The heterocyclic alkyl group in $R^3$ includes the above-mentioned alkyl groups which have been substituted by the above-mentioned heterocyclic group. The cycloalkyl group in $R^3$ includes $C_{3-8}$cycloalkyl groups such as cyclopropyl, cyclobutyl, cyclopentyl, cyclohexyl, cycloheptyl, cyclooctyl, and the like. The cycloalkenyl group in $R_3$ includes $C_{3-8}$cycloalkenyl groups such as 1-cyclopropenyl, 2-cyclopropenyl, 1-cyclobutenyl, 2-cyclobutenyl, 1-cyclopentenyl, 3-cyclopentenyl, 4-cyclopentenyl, 1-cyclohexenyl, 3-cyclohexenyl, 4-cyclohexenyl, cycloheptenyl, cyclooctenyl and the like. The iminoalkyl group in $R^3$ includes imino—$C_{1-8}$alkyl groups, for example, iminomethyl, 1-iminoethyl, 2-iminoethyl and the like. The acyl group in $R^3$ includes formyl group; alkanoyl groups such as acetyl, propionyl and the like; aroyl groups such as benzoyl, p-nitrobenzoyl and the like; and heterocyclic carbonyl group such as thenoyl, furoyl and the like. The bridged hydrocarbon group in $R^3$ includes $C_{4-15}$bridged hydrocarbons, such as 3,6-methanocyclohexen4-yl, adamantyl and the like.

As the substituents for said $R^2$ and $R^3$ groups, there may be used halogen atoms, for example, fluorine, chlorine, bromine, iodine and the like; alkyl groups such as straight or branched chain $C_{1-10}$alkyl groups, for example, methyl, ethyl, n-propyl, isopropyl, n-butyl, isobutyl, sec.-butyl, tert.-butyl, pentyl, hexyl, heptyl, octyl and the like; aralkyl groups such as phenyl—$C_{1-4}$—alkyl groups and naphthyl—$C_{1-4}$alkyl groups, for example, benzyl, phenethyl, naphthylmethyl, naphthylethyl and the like; hydroxyl group; alkoxy groups such as $C_{1-10}$alkoxy groups, for example, methoxy, ethoxy, n-propoxy, isopropoxy, n-butoxy, isobutoxy, sec.-butoxy, tert-butoxy, pentyloxy, hexyloxy, heptyloxy, octyloxy and the like; alkylthio groups such as $C_{1-10}$alkylthio groups, for example, methylthio, ethylthio, n-propylthio, isopropylthio, n-butylthio, isobutylthio, sec.-butylthio, tert.-butylthio, pentylthio, hexylthio, heptylthio, octylthio and the like; nitro group; cyano group; amino group; alkylamino groups such as $C_{1-8}$alkylamino groups, for example, methylamino, ethylamino, n-propylamino, isopropylamino, n-butylamino, isobutylamino, sec.-butylamino, tert.-butylamino, and the like; di-alkylamino groups such as di—$C_{1-8}$alkylamino groups, for example, dimethylamino, diethylamino, di-n-propylamino, di-n-butylamino and the like; alkenylamino groups such as $C_{2-8}$alkenylamino groups, for example, vinylamino, allylamino and the like; carboxyl group; carbamoyl group; acyl groups such as formyl group, alkanoyl group, for example, acetyl, propionyl and the like, aroyl groups, for example, benzoyl, p-nitrobenzoyl and the like, and heterocyclic carbonyl groups, for example, thenoyl, furoyl and the like; acyloxy groups, for example, acyl—O—groups in which the acyl is the same as mentioned above; acylalkyl groups, for example, the above-mentioned alkyl groups which have been substituted by the above-mentioned acyl group; acylamino groups, for example, acyl—NH—groups in which the acyl is the same as mentioned above; alkoxycarbonyl groups, for example,

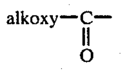

groups in which the alkoxy is the same as mentioned above; aminoalkyl groups, for example, $NH_2$—alkyl groups in which the alkyl is the same as mentioned above; alkylaminoalkyl groups, for example, the above-mentioned alkyl groups which have been substituted by the above-mentioned alkylamino group; dialkylaminoalkyl groups, for example, the above-mentioned alkyl groups which have been substituted by the above-mentioned dialkylamino group; hydroxylalkyl groups, for example, HO—alkyl groups in which the alkyl is the same as mentioned above; hydroxyiminoalkyl groups, for example, HON═alkyl in which the alkyl is the same as mentioned above; alkoxyalkyl groups, for example, the above-mentioned alkyl groups substituted by the above-mentioned alkoxy group; carboxyalkyl groups, for example, HOOC—alkyl groups in which the alkyl is the same as mentioned above; alkoxycarbonylalkyl groups, for example,

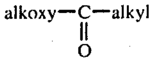

groups in which the alkoxy and the alkyl are the same as mentioned above; sulfoalkyl groups, for example, the above-mentioned alkyl groups substituted by a sulfo group; sulfo group; sulfoxy group; sulfamoyl group; sulfamoylalkyl groups, for example, the above-mentioned alkyl groups which have been substituted by a sulfamoyl group; carbamoylalkyl groups, for example, the above-mentioned alkyl groups which have been substituted by a carbamoyl group; aryl groups, for example, phenyl, naphthyl and the like; arylthio groups, for example, aryl—S—groups in which the aryl is the same as mentioned above; aryloxy groups, for example, aryl—O—groups in which the aryl is the above-mentioned; oxo group; thioxo group; mercapto group; ureido group; hydroxyamino group; hydroxyalkylamino groups, for example, HO-alkyl—NH—groups in which the alkyl is the same as mentioned above; halogenoalkyl groups, such as mono- , di- or tri-halogeno—$C_{1-4}$alkyl groups; for example, chloromethyl, bromomethyl, dichloromethyl, dibromomethyl, trifluoromethyl, dichloroethyl and the like; $C_{2-8}$alkenyl groups, for example, vinyl, allyl, isopropenyl, 1-propenyl, 2-butenyl, 2-pentenyl and the like; $C_{2-8}$alkynyl groups, for example, ethynyl, 1-propynyl, 2-propynyl and the like; alkenylamino groups, for example, alkenyl—NH—groups in which the alkenyl is the same as mentioned above; $C_{3-8}$cycloalkyl groups, for example, cyclopropyl, cyclobutyl, cyclopentyl, cyclohexyl, cycloheptyl and the like; $C_{6-8}$cycloalkadienyl groups, for example, cyclohexadienyl, cycloheptadienyl and the like; $C_{1-4}$alkylenedioxy groups, for example, methylenedioxy, ethylenedioxy, trimethylenedioxy and the like; epoxy group; heterocyclic groups, such as 5-membered, 6-membered and fused ring type heterocyclic groups containing at least one atom selected from N, S and O, for example, thienyl, furyl, pyrrolyl, imidazolyl, pyrazoyl, thiazolyl, isothiazolyl, oxazolyl, isoxazolyl, furazanyl, pyrrolidinyl, pyrrolinyl, imidazolidinyl, imidazolinyl, pyrazolidinyl, pyrazolinyl, oxadiazolyl, thiadiazolyl, triazolyl, tetrazolyl, thiatriazolyl, pyridyl, pyrazinyl, pyrimidinyl, pyridazinyl, piperidinyl, piperazinyl, pyranyl, morpholinyl, pyridine-1-oxide-2-yl, pyridazine-1-oxide-6-yl, quinoline-1-oxide-6-yl, triazinyl, benzothienyl, naphthothienyl, benzofuryl, 2,3-dihydrobenzofuryl, benzothiazolyl, isobenzofuryl, chromenyl, indolidinyl, isoindolyl, indolyl, indazolyl, purinyl, quinolyl, isoquinolyl, 1,2,3,4-tetrahydroquinolyl, 1,2-dihydroquinolyl, phthalazinyl, naphthylidinyl, quinoxalinyl, 1,2,3,4-tetrahydroquinoxalinyl, quinazolinyl, cinnolinyl, pteridinyl, isochromanyl, chromanyl, indolinyl, isoindolinyl, benzoxazolyl, benzomorpholinyl, triazolopyridyl, tetrazolopyridazinyl, tetrazolopyrimidinyl, thiazolopyridazinyl, thiadiazolopyridazinyl, triazolopyridazinyl and the like; and 5-nitrofurfurylideneamino groups and the like. $R^2$ and $R^3$ may have at least one of the above-mentioned substituents. In particular, halogen atoms, alkyl groups, hydroxyl group, amino group, alkoxy groups, alkylamino groups, dialkylamino groups, nitro group, aryl groups and heterocyclic groups are preferred as the substituents.

The above-mentioned substituents for $R^2$ and $R^3$ may have at least one substituent selected from halogen atoms, hydroxyl group, carboxyl group, nitro group, alkyl groups, alkoxy groups, amino group, alkylamino groups, dialkylamino groups, aryl groups, acyl groups and the like, in which as the halogen atoms, alkyl groups, alkoxy groups, alkylamino groups, dialkylamino groups, aryl groups and acyl groups, there may be used those mentioned above as substituents for $R^2$ and $R^3$.

Furthermore, when $R^2$ and $R^3$ of the present compound have hydroxyl, amino or carboxyl, these groups may be protected by known protecting groups. As the protecting group for the hydroxyl group, there may be used all groups which can conventionally be used for the protection of hydroxyl group, specifically including readily removable acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, tert.-butoxycarbonyl, 1,1-dimethylpropoxycarbonyl, isopropoxycarbonyl, diphenylmethoxycarbonyl, 2,2,2-trichloroethoxycarbonyl, 2,2,2-tribromoethoxycarbonyl, 2-furfuryloxycarbonyl, 1-adamantyloxycarbonyl, 1-cyclopropylethoxycarbonyl, 8-quinolyloxycarbonyl, formyl, acetyl, chloroacetyl, trifluoroacetyl and the like, as well as benzyl, benzhydryl, trityl, methoxymethyl, tetrahydrofuryl, tetrahydropyranyl, 2-nitrophenylthio, 2,4-nitrophenylthio, and the like. As the protecting group for the amino group, there may be used all groups which can conventionally be used for the protection of amino group, specifically including readily removable acyl groups such as 2,2,2-trichloroethoxycarbonyl, 2,2,2-tribromoethoxycarbonyl, benzyloxycarbonyl, p-toluenesulfonyl, p-nitrobenzyloxycarbonyl, o-bromobenzyloxycarbonyl, o-nitrophenylsulfenyl, acetyl, (mono-, di- or tri-)chloroacetyl, trifluoroacetyl, formyl, tert.-amyloxycarbonyl, tert.-butoxycarbonyl, p-methoxybenzyloxycarbonyl, 3,4-dimethoxybenxyloxycarbonyl, 4-(phenylazo)benzyloxycarbonyl, 4-(4-methoxyphenylazo)benzyloxycarbonyl, pyridine-1-oxide-2-yl-methoxycarbonyl, 2-furyloxycarbonyl, diphenylmethoxycarbonyl, 1,1-dimethylpropoxycarbonyl, isopropoxycarbonyl, 1-cyclopropylethoxycarbonyl, phthaloyl, succinyl, 1-adamantyloxycarbonyl, 8-quinolyloxycarbonyl and the like, as well as such readily removable groups as trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxocyclohexylidene, 4-nitrofurfurylidene and the like, and other protecting groups for amino group such as di- or trialkylsilyl and the like. As the protecting group for carboxyl group, there may be used all groups which can conventionally be used for the protection of carboxyl group, specifically including such groups as methyl, ethyl, n-propyl, iso-propyl, tert.-butyl, n-butyl, benzyl, diphenylmethyl, trityl, p-nitrobenzyl, p-methoxybenzyl, benzoylmethyl, acetylmethyl, p-nitrobenzoylmethyl, p-bromobenzoylmethyl, p-methanesulfonylbenzoylmethyl, phthalimidomethyl, 2,2,2-trichloroethyl, 1,1-dimethyl-2-propenyl, 1,1-dimethylpropyl, acetoxymethyl, propionyloxymethyl, pivaloyloxymethyl, 3-methyl-3-butynyl, succinimidomethyl, 1-cyclopropylethyl, methylsulfenylmethyl, phenylthiomethyl, dimethylaminomethyl, quinoline-1-oxide-2-yl-methyl, pyridine-1-oxide-2-yl-methyl, bis(p-methoxyphenyl)-methyl and the like; non-metallic compounds such as titanium tetrachloride; and silyl compounds such as dimethylchlorosilane as mentioned in Japanese Patent Application Kokai (Laid-Open) No. 7,073/71, and Dutch Patent Application No. 71 05259 (Laid open).

The salts of the compound represented by the formula [I] include conventionally known salts at basic groups, such as amino group and salts at acidic groups, such as carboxyl group. The salts at basic groups include, for example, salts with mineral acids, such as hydrochloric acid, sulfuric acid and the like, salts with organic carboxylic acids such as oxalic acid, formic acid, trichloroacetic acid and trifluoroacetic acid and the like; salts with sulfonic acids such as methanesulfonic acid, p-toluenesulfonic acid, naphthalenesulfonic acid and the like; and salts with amino acids such as aspartic acid, glutamic acid and the like. The salts at acidic groups include, for example, salts with alkali metals such as sodium, potassium and the like; salts with alkaline earth metals such as calcium, magnesium and the like; ammonium salts, salts with nitrogen-containing organic bases such as procain, dibenzylamine, N-benzyl-$\beta$-phenethylamine, 1-ephenamine, N,N-dibenzylethylenediamine and the like; and salts with other nitrogen-containing organic bases such as triethylamine, trimethylamine, tributylamine, pyridine, N,N-dimethylaniline, N-methylpiperidine, N-methylmorpholine, diethylamine, dicyclohexylamine and the like.

Moreover, when the compounds represented by the formula [I] and their salts have isomers, for example, optical isomers, geometrical isomers, tautomeric isomers and the like, these isomers are all included in the present invention, and all crystal forms and hydrates are also included in the present invention.

The antibacterial activity and acute toxicity of the representative compounds of this invention are as follows:

1. Antibacterial activity

Test method

According to the standard method of the Nippon Chemotherapy Society [Chemotherapy, Vol. 23, pages 1 to 2 (1975)], a bacterial solution obtained by culturing in Heart Infusion broth (manufactured by Eiken Kagaku) at 37° C. for 20 hours was inoculated into a Heart Infusion agar medium (manufactured by Eiken Kagaku) containing a test drug, and subjected to culturing at 37° C. for 20 hours, after which the growth of bacteria was observed to determine the minimum concentration at which the growth of bacteria was inhibited, which is expressed as MIC ($\mu$g/ml). The amount of bacteria inoculated was $10^4$ cells per plate ($10^6$ cells per ml).

* Penicillinase-producing bacteria

** Cephalospolinase-producing bacteria

MIC values of various compounds of this invention represented by the formula [I] in which $R^1$ is hydrogen are shown in Table 1.

TABLE 1

| Compound | | | | | |
|---|---|---|---|---|---|
| R[2] | 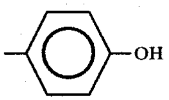 | 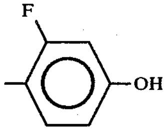 | 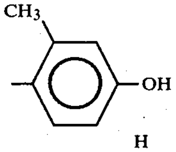 | 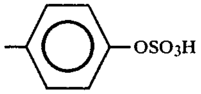 | 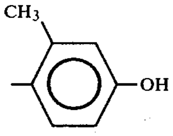 |
| Strain R[3] | 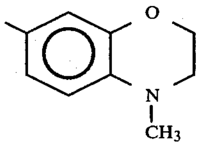 | 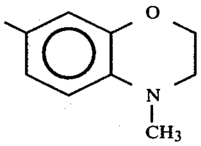 | 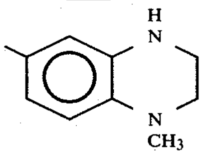 | 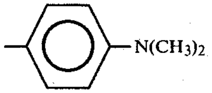 | 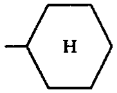 |
| *St. aureus* FDA209P | 0.39 | 0.39 | 0.78 | 0.78 | 0.78 |
| *E. coli* NIHJ JC-2 | 0.39 | 0.39 | 0.39 | 1.56 | 1.56 |
| *E. coli* TK-111 | 0.2 | 0.1 | 0.2 | 0.78 | 0.78 |
| *Kl. pneumoniae* Y-50 | 0.78 | 0.39 | 0.39 | 3.13 | 1.56 |
| *Kl. pneumoniae* Y-41 | 3.13 | 3.13 | 3.13 | 25 | 6.25 |
| *Ent. cloacae* IID977 | 1.56 | 0.78 | 1.56 | 12.5 | 3.13 |
| *Pro. vulgaris* GN3027 | 0.39 | 0.39 | 0.78 | 1.56 | 0.2 |
| *Pro. morganii* T-216 | 1.56 | 1.56 | 3.13 | 12.5 | 6.25 |
| *Ps. aeruginosa* IFO3445 | 12.5 | 6.25 | 25 | 50 | 50 |
| *Ps. aeruginosa* S-68 | 6.25 | 6.25 | 12.5 | 25 | 50 |
| *Pro. mirabilis* T-111 | 3.13 | 3.13 | 3.13 | 25 | 12.5 |
| *Aci. antitratus* A-6 | 0.78 | 0.39 | 1.56 | 3.13 | 0.78 |
| *St. aureus* F-137* | 0.39 | 0.2 | 0.78 | 3.13 | 0.78 |
| *E. coli* TK-3* | 0.78 | 0.78 | 0.78 | 6.25 | 3.13 |
| *E. coli* GN5482** | ≦0.05 | ≦0.05 | 0.1 | 0.2 | 0.1 |
| *Kl. pneumoniae* Y-4* | 3.13 | 3.13 | 6.25 | 25 | 12.5 |
| *Pro. vulgaris* GN76** | 3.13 | 3.13 | 1.56 | 3.13 | 3.13 |
| *Ps. aeruginosa* GN918** | 6.25 | 3.13 | 3.13 | 12.5 | 3.13 |
| *Ps. aeruginosa* GN3379* | 12.5 | 12.5 | 25 | 50 | >100 |

| Compound | | | | | |
|---|---|---|---|---|---|
| R[2] | 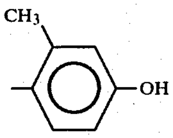 | 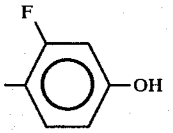 | 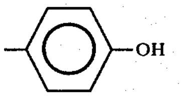 | 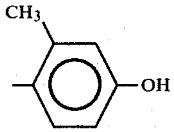 | 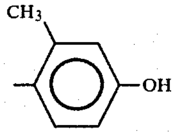 |
| Strain R[3] | 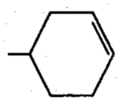 | 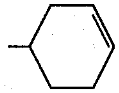 | 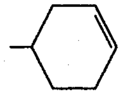 | 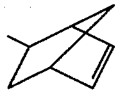 | 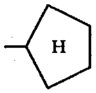 |
| *St. aureus* FDA209P | 0.2 | 0.39 | 1.56 | 3.13 | 0.78 |
| *E. coli* NIHJ JC-2 | 0.39 | 1.56 | 6.25 | 3.13 | 0.78 |
| *E. coli* TK-111 | 0.1 | 0.39 | 1.56 | 1.56 | 0.39 |
| *Kl. pneumoniae* Y-50 | 0.39 | 0.78 | 1.56 | 3.13 | 0.78 |
| *Kl. pneumoniae* Y-41 | 1.56 | 6.25 | 6.25 | 25 | 3.13 |
| *Ent. cloacae* IID977 | 0.78 | 3.13 | 6.25 | 12.5 | 1.56 |

TABLE 1-continued

| | | | | | |
|---|---|---|---|---|---|
| *Pro. vulgaris* GN3027 | ≦0.05 | 0.1 | 0.39 | 0.78 | ≦0.05 |
| *Pro. morganii* T-216 | 1.56 | 3.13 | 3.13 | 12.5 | 3.13 |
| *Ps. aeruginosa* IFO3445 | 6.25 | 12.5 | 12.5 | >100 | 12.5 |
| *Ps. aeruginosa* S-68 | 6.25 | 12.5 | 12.5 | >100 | 12.5 |
| *Pro. mirabilis* T-111 | 1.56 | 12.5 | 12.5 | 25 | 3.13 |
| *Aci. antitratus* A-6 | 0.2 | 3.13 | 6.25 | 6.25 | 0.78 |
| *St. aureus* F-137* | 0.1 | 0.39 | 3.13 | 3.13 | 0.39 |
| *E. coli* TK-3* | 0.78 | 3.13 | 6.25 | 12.5 | 1.56 |
| *E. coli* GN5482** | 0.1 | 0.39 | 0.39 | 1.56 | 0.2 |
| *Kl. pneumoniae* Y-4* | 1.56 | 6.25 | 12.5 | 25 | 6.25 |
| *Pro. vulgaris* GN76** | 0.39 | 0.78 | 1.56 | 6.25 | 0.78 |
| *Ps. aeruginosa* GN918** | 0.78 | 1.56 | 1.56 | 50 | 3.13 |
| *Ps. aeruginosa* GN3379* | 6.25 | 12.5 | 25 | >100 | 25 |
| Compound R² | 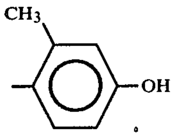 | 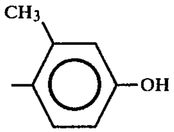 | 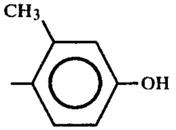 | 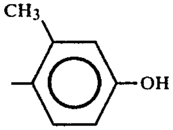 | 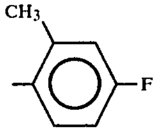 |
| Strain R³ | 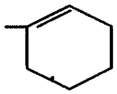 | 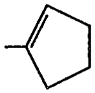 | $-CH{=}CHCH_3$ | $-CH_2CH_2-$ 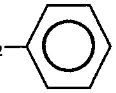 | 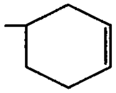 |
| *St. aureus* FDA209P | 0.78 | 0.78 | 6.25 | 0.78 | 3.13 |
| *E. coli* NIHJ JC-2 | 1.56 | 0.78 | 3.13 | 3.13 | 6.25 |
| *E. coli* TK-111 | 0.39 | 0.2 | 1.56 | 0.39 | 1.56 |
| *Kl. pneumoniae* Y-50 | 0.78 | 0.39 | 1.56 | 1.56 | 3.13 |
| *Kl. pneumoniae* Y-41 | 6.25 | 1.56 | 12.5 | 12.5 | 25 |
| *Ent. cloacae* IID977 | 3.13 | 1.56 | 6.25 | 6.25 | 12.5 |
| *Pro. vulgaris* GN3027 | 0.39 | 0.1 | 0.39 | 0.1 | 0.39 |
| *Pro. morganii* T-216 | 3.13 | 1.56 | 3.13 | 3.13 | 12.5 |
| *Ps. aeruginosa* IFO3445 | 25 | 6.25 | 25 | 25 | 100 |
| *Ps. aeruginosa* S-68 | 25 | 6.25 | 12.5 | 12.5 | 50 |
| *Pro. mirabilis* T-111 | 6.25 | 3.13 | 25 | 12.5 | 25 |
| *Aci. antitratus* A-6 | 0.39 | 0.78 | 6.25 | 0.39 | — |
| *St. aureus* F-137* | 0.78 | 0.78 | 12.5 | 0.78 | 3.13 |
| *E. coli* TK-3* | 3.13 | 1.56 | 3.13 | 3.13 | 12.5 |
| *E. coli* GN5482** | 0.2 | 0.1 | 0.39 | 0.2 | 0.78 |
| *Kl. pneumoniae* Y-4* | 12.5 | 6.25 | 25 | 12.5 | 25 |
| *Pro. vulgaris* GN76** | 1.56 | 0.78 | 1.56 | 1.56 | 6.25 |
| *Ps. aeruginosa* GN918** | 12.5 | 3.13 | 6.25 | 3.13 | 12.5 |
| *Ps. aeruginosa* GN3379* | 50 | 25 | 25 | 12.5 | 100 |
| Compound R² | 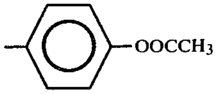 | 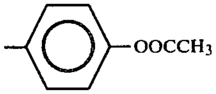 | 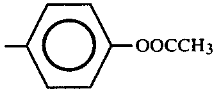 | 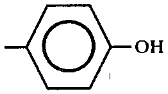 | 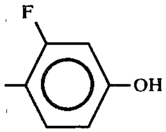 |

TABLE 1-continued

| Strain | R3 | 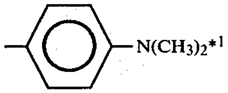 | 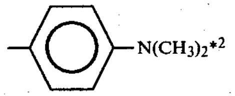 | 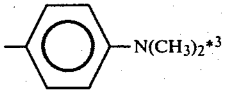 | 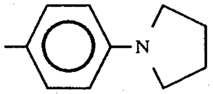 | 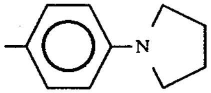 |
|---|---|---|---|---|---|---|
| *St. aureus* FDA209P | | 0.39 | 0.39 | 1.56 | 0.2 | ≦0.05 |
| *E. coli* NIHJ JC-2 | | 0.39 | 0.39 | 3.13 | 0.39 | 0.2 |
| *E. coli* TK-111 | | 0.2 | 0.2 | 0.78 | 0.2 | ≦0.05 |
| *Kl. pneumoniae* Y-50 | | 0.78 | 0.78 | 3.13 | 0.78 | 0.39 |
| *Kl. pneumoniae* Y-41 | | 3.13 | 3.13 | 25 | 1.56 | 1.56 |
| *Ent. cloacae* IID977 | | 1.56 | 1.56 | 6.25 | 0.78 | 0.78 |
| *Pro. vulgaris* GN3027 | | 0.39 | 0.39 | 0.78 | 0.2 | 0.2 |
| *Pro. morganii* T-216 | | 3.13 | 3.13 | 12.5 | 1.56 | 0.78 |
| *Ps. aeruginosa* IFO3445 | | 12.5 | 12.5 | 50 | 6.25 | 6.25 |
| *Ps. aeruginosa* S-68 | | 6.25 | 6.25 | 25 | 3.13 | 3.13 |
| *Pro. mirabilis* T-111 | | 6.25 | 6.25 | 25 | 1.56 | 0.78 |
| *Aci. antitratus* A-6 | | 0.39 | 0.39 | 1.56 | ≦0.05 | ≦0.05 |
| *St. aureus* F-137* | | 0.39 | 0.39 | 1.56 | 0.1 | ≦0.05 |
| *E. coli* TK-3* | | 1.56 | 1.56 | 6.25 | 0.78 | — |
| *E. coli* GN5482** | | ≦0.05 | ≦0.05 | 0.1 | ≦0.05 | ≦0.05 |
| *Kl. pneumoniae* Y-4* | | 6.25 | 6.25 | 25 | 3.13 | 3.13 |
| *Pro. vulgaris* GN76** | | 1.56 | 1.56 | 6.25 | 0.78 | 0.78 |
| *Ps. aeruginosa* GN918** | | 3.13 | 3.13 | 12.5 | 1.56 | 0.78 |
| *Ps. aeruginosa* GN3379* | | 12.5 | 12.5 | 50 | 3.13 | 3.13 |

| Compound | | | | | | |
|---|---|---|---|---|---|---|
| | R2 | 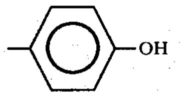 | 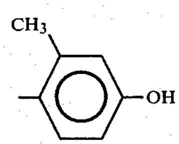 | 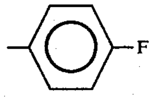 | 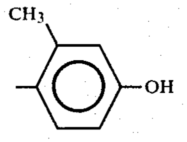 | 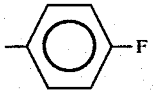 |
| Strain | R3 | 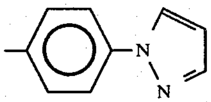 | 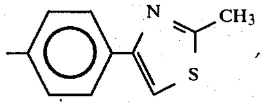 , | 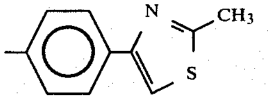 | 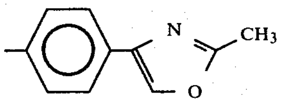 | 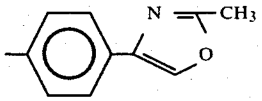 |
| *St. aureus* FDA209P | | 0.39 | ≦0.05 | 0.2 | 0.1 | 0.39 |
| *E. coli* NIHJ JC-2 | | 0.1 | 0.1 | 1.56 | 0.1 | 0.78 |
| *E. coli* TK-111 | | ≦0.05 | ≦0.05 | 0.39 | ≦0.05 | 0.39 |
| *Kl. pneumoniae* Y-50 | | 0.2 | 0.2 | 3.13 | 0.2 | 1.56 |
| *Kl. pneumoniae* Y-41 | | 0.78 | 1.56 | 6.25 | 1.56 | 6.25 |
| *Ent. cloacae* IID977 | | 0.2 | 0.39 | 6.25 | 0.39 | 3.13 |
| *Pro. vulgaris* GN3027 | | 0.39 | 0.39 | 1.56 | 0.39 | 0.39 |
| *Pro. morganii* T-216 | | 1.56 | 1.56 | 3.13 | 3.13 | 6.25 |
| *Ps. aeruginosa* IFO3445 | | 6.25 | 3.13 | 25 | 3.13 | 25 |
| *Ps. aeruginosa* S-68 | | 6.25 | 3.13 | 12.5 | 3.13 | 12.5 |
| *Pro. mirabilis* T-111 | | 3.13 | 0.78 | 6.25 | 1.56 | 6.25 |
| *Aci. antitratus* A-6 | | 0.78 | ≦0.05 | 0.1 | 0.39 | 0.2 |
| *St. aureus* F-137* | | 0.39 | ≦0.05 | 0.2 | 0.1 | 0.39 |
| *E. coli* TK-3* | | 0.2 | 0.39 | 3.13 | 0.2 | 3.13 |
| *E. coli* GN5482** | | ≦0.05 | ≦0.05 | 0.78 | ≦0.05 | 0.2 |

TABLE 1-continued

| | | | | | |
|---|---|---|---|---|---|
| *Kl. pneumoniae* Y-4* | 0.78 | 1.56 | 25 | 3.13 | 12.5 |
| *Pro. vulgaris* GN76** | 1.56 | 0.39 | 3.13 | 0.78 | 3.13 |
| *Ps. aeruginosa* GN918** | 3.13 | 0.39 | 3.13 | 0.78 | 3.13 |
| *Ps. aeruginosa* GN3379* | 6.25 | 6.25 | 25 | 6.25 | 25 |
| Compound | | | | | |
| $R^2$ | 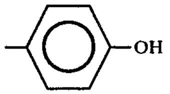 | 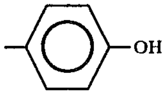 | 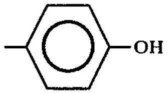 | 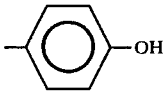 | 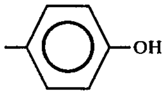 |
| Strain $R^3$ | 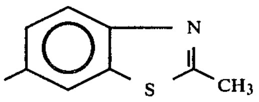 | 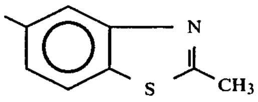 | 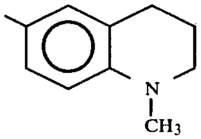 | 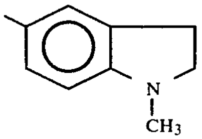 | 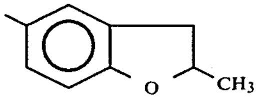 |
| *St. aureus* FDA209P | 0.39 | 0.39 | 0.39 | 0.2 | 1.56 |
| *E. coli* NIHJ JC-2 | 0.39 | 0.39 | 0.39 | 0.2 | 1.56 |
| *E. coli* TK-111 | 0.2 | 0.1 | 0.2 | ≦0.05 | 0.78 |
| *Kl. pneumoniae* Y-50 | 0.39 | 0.78 | 1.56 | 0.39 | 1.56 |
| *Kl. pneumoniae* Y-41 | 3.13 | 3.13 | 3.13 | 1.56 | 6.25 |
| *Ent. cloacae* IID977 | 1.56 | 1.56 | 1.56 | 0.78 | 3.13 |
| *Pro. vulgaris* GN3027 | 0.39 | 0.39 | 0.78 | 0.2 | 0.78 |
| *Pro. morganii* T-216 | 3.13 | 3.13 | 3.13 | 0.78 | 3.13 |
| *Ps. aeruginosa* IFO3445 | 25 | 12.5 | 12.5 | 12.5 | 50 |
| *Ps. aeruginosa* S-68 | 12.5 | 6.25 | 6.25 | 6.25 | 25 |
| *Pro. mirabilis* T-111 | 3.13 | 3.13 | 3.13 | 3.13 | 12.5 |
| *Aci. antitratus* A-6 | — | — | 0.39 | 0.39 | 3.13 |
| *St. aureus* F-137* | 0.39 | 0.78 | 0.2 | 0.1 | 3.13 |
| *E. coli* TK-3* | 0.78 | 0.78 | 1.56 | 0.39 | 3.13 |
| *E. coli* GN5482** | ≦0.05 | ≦0.05 | ≦0.05 | ≦0.05 | 1.56 |
| *Kl. pneumoniae* Y-4* | 3.13 | 3.13 | 6.25 | 1.56 | 12.5 |
| *Pro. vulgaris* GN76** | 0.78 | 1.56 | 1.56 | 0.39 | 3.13 |
| *Ps. aeruginosa* GN918** | 1.56 | 1.56 | 3.13 | 1.56 | 12.5 |
| *Ps. aeruginosa* GN3379* | 12.5 | 6.25 | 12.5 | 6.25 | 25 |
| Compound | | | | | |
| $R^2$ | 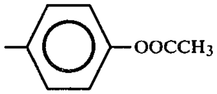 | 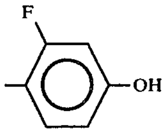 | 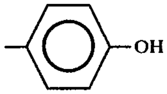 | 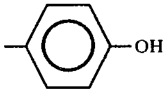 | 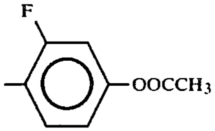 |
| Strain $R^3$ | 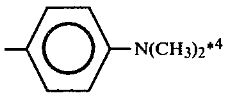 | 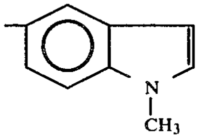 | 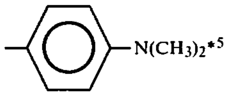 | 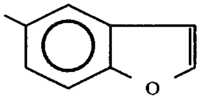 | 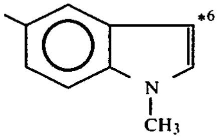 |
| *St. aureus* FDA209P | 0.2 | 0.05 | 0.39 | 0.2 | ≦0.05 |

TABLE 1-continued

| | | | | | |
|---|---|---|---|---|---|
| *E. coli* NIHJ JC-2 | 0.2 | ≦0.05 | 0.39 | 0.39 | 0.1 |
| *E. coli* TK-111 | 0.1 | ≦0.05 | 0.2 | 0.2 | ≦0.05 |
| *Kl. pneumoniae* Y-50 | 0.39 | 0.2 | 0.78 | 0.39 | 0.39 |
| *Kl. pneumoniae* Y-41 | 3.13 | 0.39 | 3.13 | 1.56 | 3.13 |
| *Ent. cloacae* IID977 | 0.78 | 0.39 | 1.56 | 0.78 | 0.78 |
| *Pro. vulgaris* GN3027 | 0.2 | ≦0.05 | 0.39 | ≦0.05 | 0.1 |
| *Pro. morganii* T-216 | 1.56 | 0.39 | 1.56 | 0.78 | 3.13 |
| *Ps. aeruginosa* IFO3445 | 12.5 | 1.56 | 6.25 | 12.5 | 6.25 |
| *Ps. aeruginosa* S-68 | 6.25 | 1.56 | 3.13 | 6.25 | 6.25 |
| *Pro. mirabilis* T-111 | 3.13 | 0.39 | 3.13 | 3.13 | 1.56 |
| *Aci. antitratus* A-6 | 0.2 | ≦0.05 | — | 0.78 | 0.39 |
| *St. aureus* F-137* | 0.2 | ≦0.05 | 0.39 | 0.39 | ≦0.05 |
| *E. coli* TK-3* | 0.78 | 0.2 | 1.56 | — | 0.39 |
| *E. coli* GN5482** | ≦0.05 | ≦0.05 | ≦0.05 | ≦0.05 | ≦0.05 |
| *Kl. pneumoniae* Y-4* | 3.13 | 0.78 | 3.13 | 3.13 | 3.13 |
| *Pro. vulgaris* GN76** | 1.56 | 0.39 | 3.13 | 0.78 | 0.78 |
| *Ps. aeruginosa* GN918** | 1.56 | 0.78 | 3.13 | 1.56 | 1.56 |
| *Ps. aeruginosa* GN3379* | 6.25 | 3.13 | 6.25 | 6.25 | 12.5 |
| Compound | | | | | |
| $R^2$ | 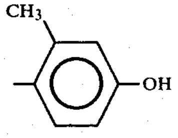 | 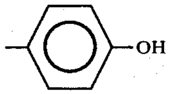 | 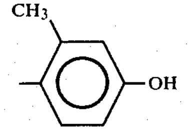 | 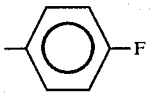 | 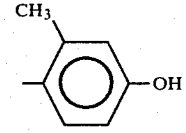 |
| Strain $R^3$ | 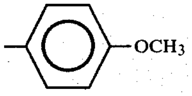 | 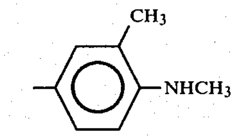 | 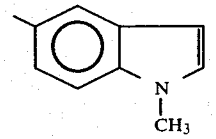 | 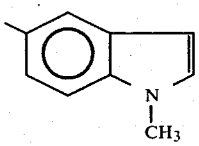 | 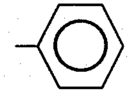 |
| *St. aureus* FDA209P | 0.1 | 0.39 | ≦0.05 | 0.39 | 0.2 |
| *E. coli* NIHJ JC-2 | 0.1 | 0.39 | ≦0.05 | 0.39 | 0.2 |
| *E. coli* TK-111 | 0.05 | 0.1 | 0.05 | 0.1 | 0.1 |
| *Kl. pneumoniae* Y-50 | 0.1 | 0.39 | 0.2 | 0.78 | 0.1 |
| *Kl. pneumoniae* Y-41 | 0.78 | 1.56 | 0.78 | 3.13 | 0.78 |
| *Ent. cloacae* IID977 | 0.39 | 0.78 | 0.39 | 1.56 | 0.39 |
| *Pro. vulgaris* GN3027 | ≦0.05 | 0.39 | 0.1 | 0.2 | ≦0.05 |
| *Pro. morganii* T-216 | 1.56 | 1.56 | 0.78 | 1.56 | 0.39 |
| *Ps. aeruginosa* IFO3445 | 3.13 | 3.13 | 3.13 | 12.5 | 6.25 |
| *Ps. aeruginosa* S-68 | 3.13 | 3.13 | 3.13 | 12.5 | 3.13 |
| *Pro. mirabilis* T-111 | 1.56 | 3.13 | 0.78 | 3.13 | 0.78 |
| *Aci. antitratus* A-6 | 0.2 | 0.78 | ≦0.05 | 0.1 | 0.78 |
| *St. aureus* F-137* | 0.1 | 0.39 | ≦0.05 | 0.39 | 0.2 |
| *E. coli* TK-3* | 0.2 | 0.39 | 0.2 | 1.56 | 0.39 |
| *E. coli* GN5482** | ≦0.05 | ≦0.05 | ≦0.05 | ≦0.05 | ≦0.05 |
| *Kl. pneumoniae* Y-4* | 0.78 | 1.56 | 0.78 | 3.13 | 1.56 |
| *Pro. vulgaris* GN76** | 0.39 | 0.78 | 0.39 | 0.78 | 0.2 |
| *Ps. aeruginosa* GN918** | 1.56 | 0.78 | 0.39 | 0.78 | 1.56 |
| *Ps. aeruginosa* GN3379* | 12.5 | 6.25 | 6.25 | 25 | 12.5 |

Compound

TABLE 1-continued

| Strain | | | | | |
|---|---|---|---|---|---|
| R² | 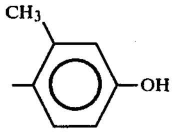 | 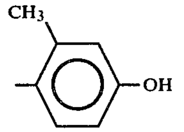 | 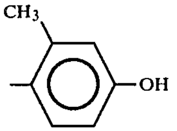 | 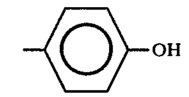 | 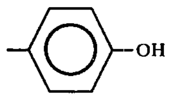 |
| R³ | 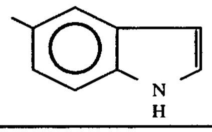 | 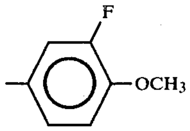 | 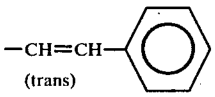 (trans) | 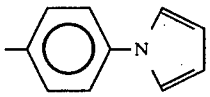 | 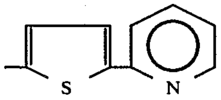 |
| *St. aureus* FDA209P | 0.1 | 0.1 | 0.1 | 0.1 | 0.2 |
| *E. coli* NIHJ JC-2 | 0.39 | 0.39 | 0.39 | 0.1 | 0.39 |
| *E. coli* TK-111 | 0.1 | ≦0.05 | 0.2 | ≦0.05 | ≦0.05 |
| *Kl. pneumoniae* Y-50 | 0.2 | 0.78 | 0.39 | 0.39 | 0.78 |
| *Kl. pneumoniae* Y-41 | 0.78 | 1.56 | 3.13 | 1.56 | 3.13 |
| *Ent. cloacae* IID977 | 0.78 | 0.39 | 1.56 | 0.78 | 1.56 |
| *Pro. vulgaris* GN3027 | 0.2 | 0.1 | 0.1 | 0.2 | 0.1 |
| *Pro. morganii* T-216 | 1.56 | 1.56 | 1.56 | 1.56 | 1.56 |
| *Ps. aeruginosa* IFO3445 | 6.25 | 12.5 | 25 | 3.13 | 3.13 |
| *Ps. aeruginosa* S-68 | 6.25 | 6.25 | 3.13 | 3.13 | 3.13 |
| *Pro. mirabilis* T-111 | 1.56 | 1.56 | 3.13 | 1.56 | 3.13 |
| *Aci. antitratus* A-6 | 3.13 | 0.39 | 0.1 | 0.1 | 0.78 |
| *St. aureus* F-137* | 0.1 | 0.1 | 0.2 | 0.1 | 0.2 |
| *E. coli* TK-3* | 0.39 | 0.39 | 0.39 | 0.39 | 0.78 |
| *E. coli* GN5482** | ≦0.05 | ≦0.05 | ≦0.05 | ≦0.05 | ≦0.05 |
| *Kl. pneumoniae* Y-4* | 1.56 | 1.56 | 3.13 | 1.56 | 3.13 |
| *Pro. vulgaris* GN76** | 0.78 | 0.39 | 0.39 | 0.78 | 0.78 |
| *Ps. aeruginosa* GN918** | 3.13 | 1.56 | 1.56 | 1.56 | 1.56 |
| *Ps. aeruginosa* GN3379* | 25 | 12.5 | 6.25 | 3.13 | 3.13 |

| Strain / Compound | | | | | |
|---|---|---|---|---|---|
| R² | 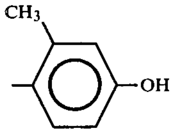 | 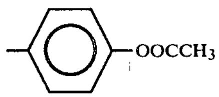 | 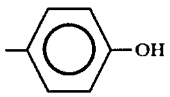 | 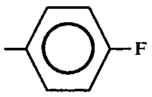 | 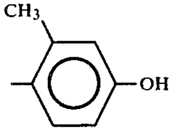 |
| R³ | 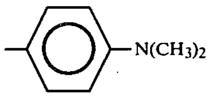 | 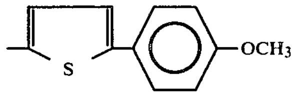 | 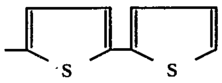 | 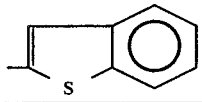 | 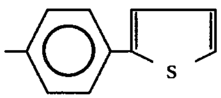 |
| *St. aureus* FDA209P | ≦0.05 | 0.1 | ≦0.05 | 0.78 | ≦0.05 |
| *E. coli* NIHJ JC-2 | 0.1 | 0.39 | 0.2 | 3.13 | 0.1 |
| *E. coli* TK-111 | ≦0.05 | 0.2 | 0.1 | 0.78 | ≦0.05 |
| *Kl. pneumoniae* Y-50 | 0.2 | 1.56 | 0.39 | 3.13 | 0.39 |
| *Kl. pneumoniae* Y-41 | 0.78 | 3.13 | 0.78 | 6.25 | 0.78 |
| *Ent. cloacae* IID977 | 0.39 | 3.13 | 0.39 | 3.13 | 0.39 |
| *Pro. vulgaris* GN3027 | 0.1 | 0.39 | 0.05 | 0.39 | ≦0.05 |
| *Pro. morganii* T-216 | 0.78 | 1.56 | 0.78 | 3.13 | 0.39 |

TABLE 1-continued

| | | | | | |
|---|---|---|---|---|---|
| *Ps. aeruginosa* IFO3445 | 3.13 | 3.13 | 1.56 | 12.5 | 6.25 |
| *Ps. aeruginosa* S-68 | 3.13 | 3.13 | 0.78 | 6.25 | 1.56 |
| *Pro. mirabilis* T-111 | 0.78 | 3.13 | 0.78 | 3.13 | 0.39 |
| *Aci. antitratus* A-6 | 0.1 | 0.2 | 0.2 | — | — |
| *St. aureus* F-137* | ≦0.05 | 0.1 | ≦0.05 | 0.39 | ≦0.05 |
| *E. coli* TK-3* | 0.2 | 1.56 | 0.39 | 3.13 | 0.39 |
| *E. coli* GN5482** | ≦0.05 | ≦0.1 | ≦0.05 | 0.39 | ≦0.05 |
| *Kl. pneumoniae* Y-4* | 0.78 | 3.13 | 1.56 | 12.5 | 0.78 |
| *Pro. vulgaris* GN76** | 0.39 | 0.78 | 0.2 | 1.56 | 0.2 |
| *Ps. aeruginosa* GN918** | 1.56 | 0.78 | 0.2 | 1.56 | 0.78 |
| *Ps. aeruginosa* GN3379* | 3.13 | 3.13 | 0.78 | 12.5 | 3.13 |

| Compound | | | | | |
|---|---|---|---|---|---|
| $R^2$ | 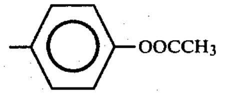 | 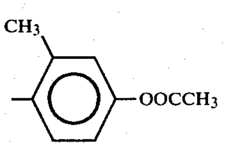 | 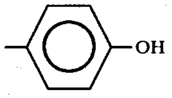 | 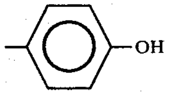 | 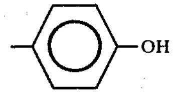 |
| Strain $R^3$ | 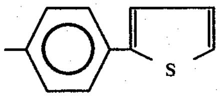 | 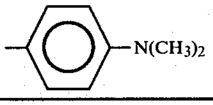 | 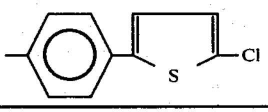 | 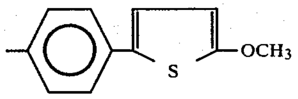 | 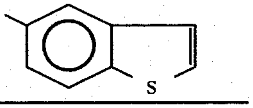 |
| *St. aureus* FDA209P | ≦0.05 | ≦0.05 | ≦0.05 | ≦0.05 | 0.2 |
| *E. coli* NIHJ JC-2 | 0.2 | 0.2 | 0.2 | 0.39 | 0.2 |
| *E. coli* TK-111 | ≦0.05 | ≦0.05 | 0.1 | 0.1 | ≦0.05 |
| *Kl. pneumoniae* Y-50 | 0.39 | 0.39 | 0.39 | 0.78 | 0.2 |
| *Kl. pneumoniae* Y-41 | 0.78 | 1.56 | 1.56 | 1.56 | 0.78 |
| *Ent. cloacae* IID977 | 0.39 | 0.78 | 0.78 | 0.78 | 0.78 |
| *Pro. vulgaris* GN3027 | ≦0.05 | 0.39 | ≦0.1 | 0.2 | ≦0.05 |
| *Pro. morganii* T-216 | 0.39 | 1.56 | 0.78 | 0.39 | 0.39 |
| *Ps. aeruginosa* IFO3445 | 1.56 | 6.25 | 3.13 | 6.25 | 1.56 |
| *Ps. aeruginosa* S-68 | 1.56 | 3.13 | 3.13 | 3.13 | 3.13 |
| *Pro. mirabilis* T-111 | 0.39 | 0.78 | 1.56 | 0.78 | 0.78 |
| *Aci. antitratus* A-6 | ≦0.05 | ≦0.05 | 0.1 | 0.1 | 0.1 |
| *St. aureus* F-137* | ≦0.05 | ≦0.05 | ≦0.05 | ≦0.05 | 0.39 |
| *E. coli* TK-3* | 0.39 | 0.39 | 0.78 | 0.39 | 0.39 |
| *E. coli* GN5482** | ≦0.05 | ≦0.05 | ≦0.05 | ≦0.05 | ≦0.05 |
| *Kl. pneumoniae* Y-4* | 1.56 | 1.56 | 1.56 | 1.56 | 0.78 |
| *Pro. vulgaris* GN76** | 0.39 | 0.39 | 0.39 | 0.39 | 0.2 |
| *Ps. aeruginosa* GN918** | 1.56 | 1.56 | 0.78 | 0.78 | 0.39 |
| *Ps. aeruginosa* GN3379* | 3.13 | 6.25 | 3.13 | 3.13 | 1.56 |

| Compound | | | | | |
|---|---|---|---|---|---|
| $R^2$ | 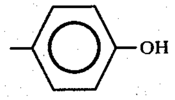 | 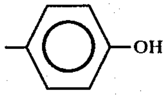 | 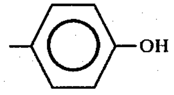 | 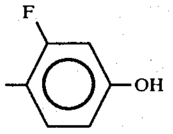 | 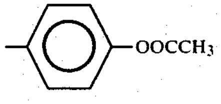 |

TABLE 1-continued

| Strain | R³ | 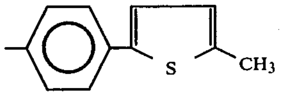 | 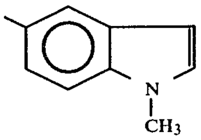 | 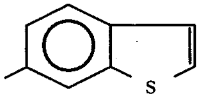 | 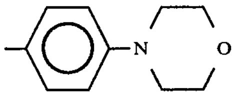 | 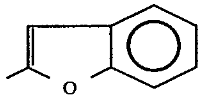 |
|---|---|---|---|---|---|---|
| *St. aureus* FDA209P | | ≦0.05 | ≦0.05 | 0.1 | 0.78 | 0.39 |
| *E. coli* NIHJ JC-2 | | 0.2 | 0.1 | 0.2 | 1.56 | 1.56 |
| *E. coli* TK-111 | | 0.1 | ≦0.05 | ≦0.05 | 0.39 | 0.78 |
| *Kl. pneumoniae* Y-50 | | 0.78 | 0.2 | 0.39 | 1.56 | 0.78 |
| *Kl. pneumoniae* Y-41 | | 1.56 | 0.78 | 0.78 | 12.5 | 6.25 |
| *Ent. cloacae* IID977 | | 0.78 | 0.39 | 0.39 | 6.25 | 3.13 |
| *Pro. vulgaris* GN3027 | | 0.1 | 0.1 | ≦0.05 | 1.56 | 0.39 |
| *Pro. morganii* T-216 | | 0.78 | 0.39 | 0.39 | 12.5 | 3.13 |
| *Ps. aeruginosa* IFO3445 | | 6.25 | 3.13 | 1.56 | 100 | 6.25 |
| *Ps. aeruginosa* S-68 | | 3.13 | 3.13 | 1.56 | 25 | 6.25 |
| *Pro. mirabilis* T-111 | | 0.39 | 0.78 | 1.56 | 12.5 | 6.25 |
| *Aci. antitratus* A-6 | | ≦0.05 | 0.1 | — | 6.25 | 0.78 |
| *St. aureus* F-137* | | ≦0.05 | ≦0.05 | 0.1 | 0.78 | 0.39 |
| *E. coli* TK-3* | | 0.39 | 0.39 | 0.39 | 3.13 | 3.13 |
| *E. coli* GN5482** | | ≦0.05 | ≦0.05 | ≦0.05 | 0.39 | 0.2 |
| *Kl. pneumoniae* Y-4* | | 1.56 | 0.78 | 1.56 | 25 | 12.5 |
| *Pro. vulgaris* GN76** | | 0.39 | 0.39 | 0.39 | 6.25 | 1.56 |
| *Ps. aeruginosa* GN918** | | 1.56 | 0.78 | 0.78 | 12.5 | — |
| *Ps. aeruginosa* GN3379* | | 6.25 | 3.13 | 3.13 | 50 | 6.25 |

| Compound | | | | | | |
|---|---|---|---|---|---|---|
| | R² | 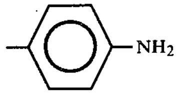 | 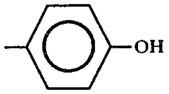 | 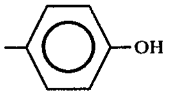 | 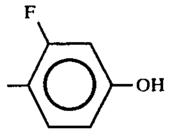 | 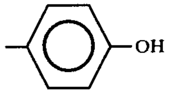 |
| Strain | R³ | 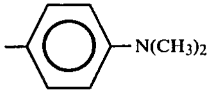 | 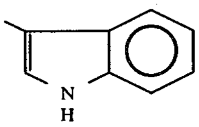 | 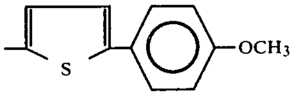 | 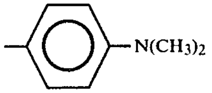 | 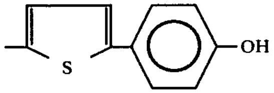 |
| *St. aureus* FDA209P | | 3.13 | 12.5 | 0.1 | ≦0.05 | 0.1 |
| *E. coli* NIHJ JC-2 | | 0.78 | 3.13 | 0.39 | 0.1 | 0.39 |
| *E. coli* TK-111 | | 0.2 | 3.13 | 0.1 | ≦0.05 | ≦0.05 |
| *Kl. pneumoniae* Y-50 | | 0.78 | 3.13 | 0.78 | 0.2 | 0.78 |
| *Kl. pneumoniae* Y-41 | | 6.25 | 25 | 1.56 | 3.13 | 3.13 |
| *Ent. cloacae* IID977 | | 1.56 | 12.5 | 0.78 | 0.2 | 1.56 |
| *Pro. vulgaris* GN3027 | | 0.39 | 1.56 | 0.2 | ≦0.05 | 0.39 |
| *Pro. morganii* T-216 | | 3.13 | 12.5 | 0.78 | 0.78 | 1.56 |
| *Ps. aeruginosa* IFO3445 | | 25 | 25 | 3.13 | 1.56 | 3.13 |
| *Ps. aeruginosa* S-68 | | 12.5 | 100 | 1.56 | 0.78 | 6.25 |
| *Pro. mirabilis* T-111 | | 6.25 | 100 | 1.56 | 0.78 | 6.25 |
| *Aci. antitratus* A-6 | | 0.39 | >100 | 0.39 | 0.1 | 0.78 |

TABLE 1-continued

| Strain | | | | | |
|---|---|---|---|---|---|
| *St. aureus* F-137* | 1.56 | 50 | 0.1 | ≦0.05 | 0.2 |
| *E. coli* TK-3* | 1.56 | 6.25 | 0.78 | 0.2 | 0.78 |
| *E. coli* GN5482** | 0.1 | 0.39 | ≦0.05 | ≦0.05 | ≦0.05 |
| *Kl. pneumoniae* Y-4* | 6.25 | 50 | 3.13 | 0.78 | 6.25 |
| *Pro. vulgaris* GN76** | 1.56 | 6.25 | 0.39 | 0.2 | 0.78 |
| *Ps. aeruginosa* GN918** | — | — | — | — | — |
| *Ps. aeruginosa* GN3379* | 6.25 | 50 | 6.25 | 3.13 | 3.13 |

| Compound | | | | | |
|---|---|---|---|---|---|
| $R^2$ | 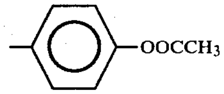 | 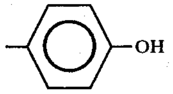 | 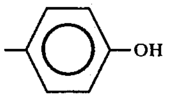 | 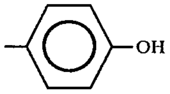 | 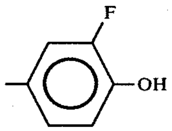 |
| Strain / $R^3$ | 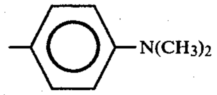 | 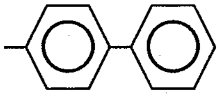 | 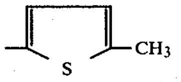 | 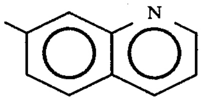 | 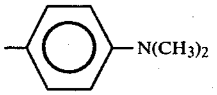 |
| *St. aureus* FDA209P | 0.1 | ≦0.05 | 0.2 | 1.56 | 0.39 |
| *E. coli* NIHJ JC-2 | 0.2 | 0.39 | 0.2 | 0.78 | 0.39 |
| *E. coli* TK-111 | ≦0.05 | 0.1 | ≦0.05 | 0.39 | 0.1 |
| *Kl. pneumoniae* Y-50 | 0.39 | 0.39 | 0.2 | 1.56 | 0.39 |
| *Kl. pneumoniae* Y-41 | 1.56 | 12.5 | 0.78 | 6.25 | 3.13 |
| *Ent. cloacae* IID977 | 1.56 | 3.13 | 0.78 | 3.13 | 1.56 |
| *Pro. vulgaris* GN3027 | 0.1 | 0.2 | ≦0.05 | 0.39 | 0.2 |
| *Pro. morganii* T-216 | 0.78 | 1.56 | 0.39 | 6.25 | 1.56 |
| *Ps. aeruginosa* IFO3445 | 3.13 | 25 | 3.13 | 25 | 3.13 |
| *Ps. aeruginosa* S-68 | 3.13 | 12.5 | 3.13 | 12.5 | 1.56 |
| *Pro. mirabilis* T-111 | 3.13 | 3.13 | 3.13 | 25 | 3.13 |
| *Aci. antitratus* A-6 | 0.2 | 0.39 | 0.39 | 25 | 0.39 |
| *St. aureus* F-137* | 0.1 | ≦0.05 | 0.2 | 1.56 | 0.39 |
| *E. coli* TK-3* | 0.39 | 0.78 | 0.2 | 0.39 | 0.78 |
| *E. coli* GN5482** | ≦0.05 | ≦0.05 | ≦0.05 | ≦0.05 | ≦0.05 |
| *Kl. pneumoniae* Y-4* | 3.13 | 12.5 | 1.56 | 12.5 | 3.13 |
| *Pro. vulgaris* GN76** | 0.39 | 0.78 | 0.2 | 3.13 | 0.78 |
| *Ps. aeruginosa* GN918** | 0.78 | 1.56 | 0.78 | 3.13 | 12.5 |
| *Ps. aeruginosa* GN3379* | 3.13 | 100 | 3.13 | 12.5 | 3.13 |

| Compound | | | | | |
|---|---|---|---|---|---|
| $R^2$ | 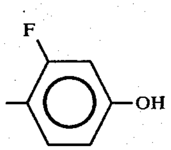 | 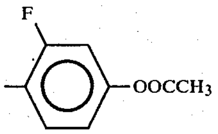 | 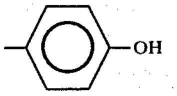 | 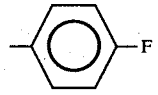 | 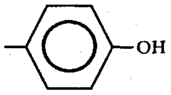 |
| Strain / $R^3$ | 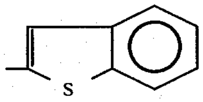 | 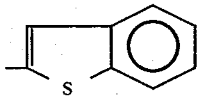 | 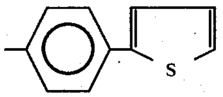 | 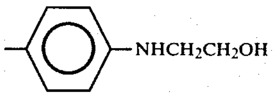 | 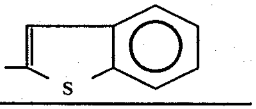 |
| *St. aureus* FDA209P | ≦0.05 | 0.1 | ≦0.05 | 6.25 | ≦0.05 |

TABLE 1-continued

| | | | | | |
|---|---|---|---|---|---|
| *E. coli* NIHJ JC-2 | 0.2 | 0.39 | 0.1 | 3.13 | 0.2 |
| *E. coli* TK-111 | ≦0.05 | ≦0.05 | ≦0.05 | 1.56 | ≦0.05 |
| *Kl. pneumoniae* Y-50 | 0.2 | 0.39 | 0.2 | 3.13 | 0.2 |
| *Kl. pneumoniae* Y-41 | 1.56 | 3.13 | 1.56 | 12.5 | 0.78 |
| *Ent. cloacae* IID977 | 0.39 | 0.78 | 0.39 | 6.25 | 0.39 |
| *Pro. vulgaris* GN3027 | ≦0.05 | 0.1 | ≦0.05 | 0.78 | ≦0.05 |
| *Pro. morganii* T-216 | 0.78 | 1.56 | 0.39 | 6.25 | 0.39 |
| *Ps. aeruginosa* IFO3445 | 1.56 | 3.13 | 1.56 | 50 | 3.13 |
| *Ps. aeruginosa* S-68 | 1.56 | 1.56 | 3.13 | 12.5 | 0.78 |
| *Pro. mirabilis* T-111 | 0.78 | 1.56 | 0.39 | 50 | 0.78 |
| *Aci. antitratus* A-6 | 0.1 | 0.2 | 0.1 | 12.5 | 0.2 |
| *St. aureus* F-137* | ≦0.05 | ≦0.05 | ≦0.05 | 6.25 | ≦0.05 |
| *E. coli* TK-3* | 0.39 | 0.39 | 0.39 | 6.25 | 0.39 |
| *E. coli* GN5482** | ≦0.05 | ≦0.05 | ≦0.05 | 0.39 | ≦0.05 |
| *Kl. pneumoniae* Y-4* | 1.56 | 3.13 | 0.78 | 25 | 0.78 |
| *Pro. vulgaris* GN76** | 0.2 | 0.39 | 0.2 | 3.13 | 0.2 |
| *Ps. aeruginosa* GN918** | 3.13 | 6.25 | 6.25 | 50 | 3.13 |
| *Ps. aeruginosa* GN3379* | 1.56 | 3.13 | 3.13 | 25 | 3.13 |

| Compound | | | | |
|---|---|---|---|---|
| $R^2$ | 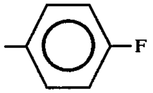 | 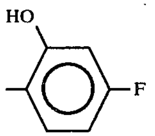 | 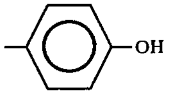 | 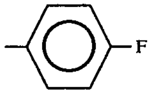 |
| Strain $R^3$ | 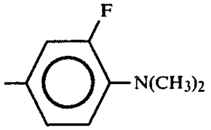 | 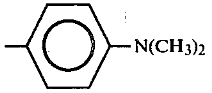 | 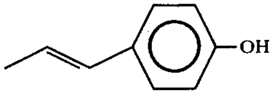 | 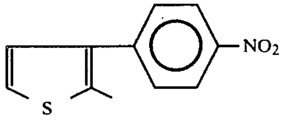 |
| *St. aureus* FDA209P | 1.56 | 0.2 | 0.78 | 0.28 |
| *E. coli* NIHJ JC-2 | 3.13 | 0.78 | 6.25 | 1.56 |
| *E. coli* TK-111 | 0.78 | 1.56 | 0.78 | 0.2 |
| *Kl. pneumoniae* Y-50 | 3.13 | 1.56 | 6.25 | 1.56 |
| *Kl. pneumoniae* Y-41 | 12.5 | 6.25 | 25 | 6.25 |
| *Ent. cloacae* IID977 | 6.25 | 1.56 | 25 | 3.13 |
| *Pro. vulgaris* GN3027 | 0.78 | 0.39 | 0.78 | 0.39 |
| *Pro. morganii* T-216 | 12.5 | 3.13 | 6.25 | 1.56 |
| *Ps. aeruginosa* IFO3445 | 50 | 12.5 | 50 | 12.5 |
| *Ps. aeruginosa* S-68 | 12.5 | 12.5 | 25 | 12.5 |
| *Pro. mirabilis* T-111 | 25 | 6.25 | 25 | 6.25 |
| *Aci. antitratus* A-6 | 1.56 | 0.78 | 6.25 | 0.78 |
| *St. aureus* F-137* | 1.56 | 0.2 | 0.78 | 0.1 |
| *E. coli* TK-3* | 6.25 | 1.56 | 6.25 | 3.13 |
| *E. coli* GN5482** | 0.39 | ≦0.05 | 0.2 | 0.2 |
| *Kl. pneumoniae* Y-4* | 25 | 6.25 | 25 | 6.25 |
| *Pro. vulgaris* GN76** | 3.13 | 1.56 | 6.25 | 3.13 |
| *Ps. aeruginosa* GN918** | 50 | 50 | 25 | 12.5 |
| *Ps. aeruginosa* GN3379* | 50 | 25 | 25 | 25 |

Compound

TABLE 1-continued

| Strain | | | | | |
|---|---|---|---|---|---|
| R² | 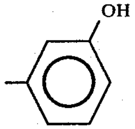 | 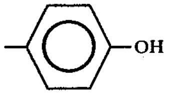 | 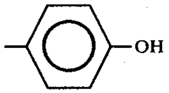 | 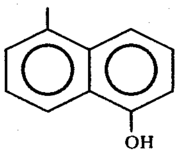 | 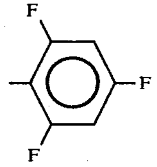 |
| R³ | 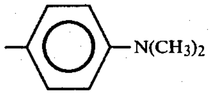 | 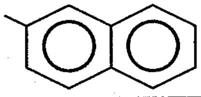 | 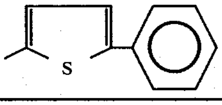 | 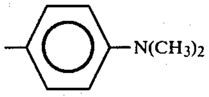 | 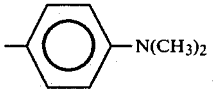 |
| *St. aureus* FDA209P | 0.2 | ≦0.05 | ≦0.05 | 0.1 | 0.78 |
| *E. coli* NIHJ JC-2 | 0.39 | 0.2 | 0.39 | 0.39 | 1.56 |
| *E. coli* TK-111 | 0.1 | ≦0.05 | ≦0.05 | ≦0.05 | 0.78 |
| *Kl. pneumoniae* Y-50 | 0.39 | 0.39 | 0.78 | 0.78 | 3.13 |
| *Kl. pneumoniae* Y-41 | 1.56 | 1.56 | 3.13 | 6.25 | 12.5 |
| *Ent. cloacae* IID977 | 0.78 | 0.39 | 1.56 | 1.56 | 6.25 |
| *Pro. vulgaris* GN3027 | 0.2 | 0.1 | ≦0.05 | 1.56 | 0.39 |
| *Pro. morganii* T-216 | 1.56 | 0.39 | 0.78 | 3.13 | 6.25 |
| *Ps. aeruginosa* IFO3445 | 12.5 | 6.25 | 3.13 | 12.5 | 100 |
| *Ps. aeruginosa* S-68 | 6.25 | 1.56 | 3.13 | 12.5 | 50 |
| *Pro. mirabilis* T-111 | 3.13 | 0.78 | 0.78 | 3.13 | 12.5 |
| *Aci. antitratus* A-6 | 0.39 | 0.2 | 0.2 | 0.39 | 0.78 |
| *St. aureus* F-137* | 0.2 | ≦0.05 | ≦0.05 | ≦0.05 | 0.78 |
| *E. coli* TK-3* | 0.39 | 0.39 | 0.78 | 1.56 | 1.56 |
| *E. coli* GN5482** | ≦0.05 | ≦0.05 | ≦0.05 | ≦0.05 | 0.39 |
| *Kl. pneumoniae* Y-4* | 3.13 | 1.56 | 1.56 | 6.25 | 12.5 |
| *Pro. vulgaris* GN76** | 0.78 | 0.39 | 0.39 | 1.56 | 1.56 |
| *Ps. aeruginosa* GN918** | 12.5 | 6.25 | 1.56 | 6.25 | 50 |
| *Ps. aeruginosa* GN3379* | 6.25 | 3.13 | 3.13 | >100 | 50 |

| Compound | | | | | |
|---|---|---|---|---|---|
| R² | 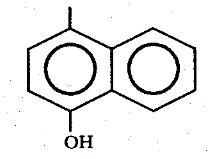 | 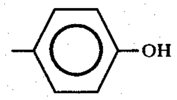 | 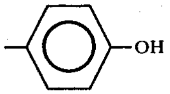 | 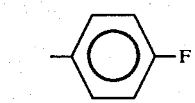 | 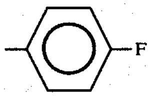 |
| Strain / R³ | 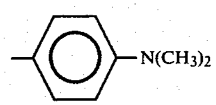 | 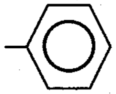 | 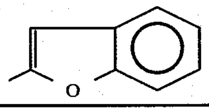 | 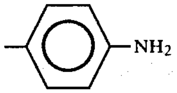 | 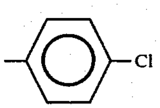 |
| *St. aureus* FDA209P | 0.78 | 0.78 | 0.2 | 3.13 | 6.25 |
| *E. coli* NIHJ JC-2 | 3.13 | 0.78 | 0.78 | 0.78 | 3.13 |
| *E. coli* TK-111 | 0.39 | 0.39 | 0.39 | 0.39 | 1.56 |
| *Kl. pneumoniae* Y-50 | 1.56 | 0.39 | 0.39 | 0.39 | 3.13 |
| *Kl. pneumoniae* Y-41 | 12.5 | 6.25 | 3.13 | 3.13 | 12.5 |
| *Ent. cloacae* IID977 | 3.13 | 1.56 | 1.56 | 1.56 | 6.25 |

TABLE 1-continued

| | | | | | |
|---|---|---|---|---|---|
| *Pro. vulgaris* GN3027 | 3.13 | 0.1 | 0.1 | 0.2 | 0.39 |
| *Pro. morganii* T-216 | 12.5 | 0.78 | 1.56 | 1.56 | 6.25 |
| *Ps. aeruginosa* IFO3445 | 50 | 6.25 | 6.25 | 6.15 | >100 |
| *Ps. aeruginosa* S-68 | 50 | 6.25 | 1.56 | 12.5 | 50 |
| *Pro. mirabilis* T-111 | 12.5 | 3.13 | 3.13 | 6.25 | 12.5 |
| *Aci. antitratus* A-6 | 0.78 | 3.13 | 0.78 | 3.13 | 3.13 |
| *St. aureus* F-137* | 0.39 | 1.56 | 0.39 | 3.13 | 6.25 |
| *E. coli* TK-3* | 3.13 | 1.56 | 0.78 | 0.78 | 6.25 |
| *E. coli* GN5482** | 0.1 | 0.1 | ≦0.05 | 0.2 | 0.39 |
| *Kl. pneumoniae* Y-4* | 12.5 | 6.25 | 6.25 | 6.25 | 25 |
| *Pro. vulgaris* GN76** | 3.13 | 0.39 | 0.39 | 0.78 | 3.13 |
| *Ps. aeruginosa* GN918** | 50 | 12.5 | 6.25 | 3.13 | 100 |
| *Ps. aeruginosa* GN3379* | >100 | 12.5 | 3.13 | 25 | 50 |
| Compound | | | | | |
| $R^2$ | 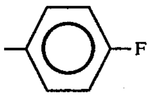 | 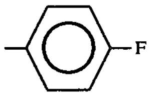 | 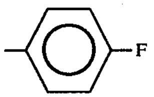 | 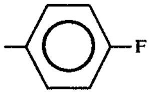 | 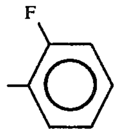 |
| Strain $R^3$ | 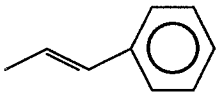 | 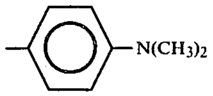 | 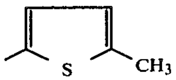 | 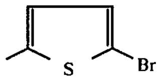 | 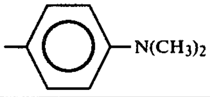 |
| *St. aureus* FDA209P | 3.13 | 0.78 | 3.13 | 1.56 | 1.56 |
| *E. coli* NIHJ JC-2 | 3.13 | 0.78 | 1.56 | 3.13 | 1.56 |
| *E. coli* TK-111 | 1.56 | 0.39 | 0.78 | 1.56 | 0.78 |
| *Kl. pneumoniae* Y-50 | 6.25 | 1.56 | 3.13 | 3.13 | 3.13 |
| *Kl. pneumoniae* Y-41 | 12.5 | 6.25 | 6.25 | 12.5 | 6.25 |
| *Ent. cloacae* IID977 | 12.5 | 3.13 | 3.13 | 12.5 | 6.25 |
| *Pro. vulgaris* GN3027 | 0.78 | 0.39 | 0.2 | 0.39 | 0.78 |
| *Pro. morganii* T-216 | 12.5 | 3.13 | 3.13 | 6.25 | 6.25 |
| *Ps. aeruginosa* IFO3445 | 50 | 25 | 50 | 50 | >100 |
| *Ps. aeruginosa* S-68 | 25 | 12.5 | 25 | 25 | 25 |
| *Pro. mirabilis* T-111 | 12.5 | 6.25 | 6.25 | 12.5 | 25 |
| *Aci. antitratus* A-6 | 1.56 | 0.39 | 1.56 | 1.56 | 1.56 |
| *St. aureus* F-137* | 3.13 | 0.78 | 3.13 | 3.13 | 1.56 |
| *E. coli* TK-3* | 12.5 | 3.13 | 3.13 | 6.25 | 3.13 |
| *E. coli* GN5482** | 0.39 | 0.2 | 0.2 | 0.39 | 0.39 |
| *Kl. pneumoniae* Y-4* | 25 | 12.5 | 12.5 | 25 | 25 |
| *Pro. vulgaris* GN76** | 3.13 | 1.56 | 1.56 | 3.13 | 3.13 |
| *Ps. aeruginosa* GN918** | 50 | 12.5 | 50 | 100 | >100 |
| *Ps. aeruginosa* GN3379* | 25 | 12.5 | 25 | 25 | >100 |
| Compound | | | | | |
| $R^2$ | 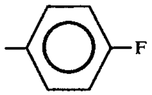 | 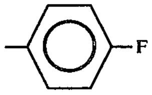 | 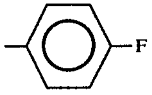 | 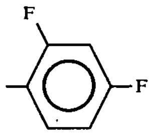 | 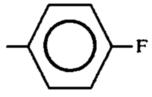 |

TABLE 1-continued

| Strain \ R³ | 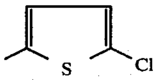 | 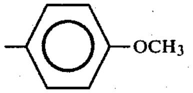 | 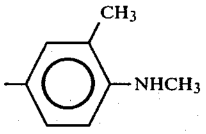 | 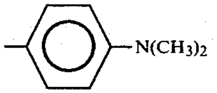 | 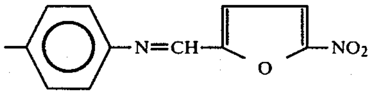 |
|---|---|---|---|---|---|
| *St. aureus* FDA209P | 3.13 | 3.13 | 1.56 | 0.2 | 6.25 |
| *E. coli* NIHJ JC-2 | 3.13 | 1.56 | 1.56 | 0.78 | 1.56 |
| *E. coli* TK-111 | 1.56 | 0.78 | 0.39 | 0.2 | 0.78 |
| *Kl. pneumoniae* Y-50 | 3.13 | 3.13 | 1.56 | 0.78 | 1.56 |
| *Kl. pneumoniae* Y-41 | 12.5 | 12.5 | 6.25 | 6.25 | 6.25 |
| *Ent. cloacae* IID977 | 12.5 | 6.25 | 6.25 | 3.13 | 6.25 |
| *Pro. vulgaris* GN3027 | 0.39 | 0.39 | 0.78 | 0.2 | 0.39 |
| *Pro. morganii* T-216 | 6.25 | 6.25 | 6.25 | 3.13 | 3.13 |
| *Ps. aeruginosa* IFO3445 | 50 | 25 | 50 | 12.5 | 25 |
| *Ps. aeruginosa* S-68 | 25 | 25 | 12.5 | 12.5 | 25 |
| *Pro. mirabilis* T-111 | 12.5 | 12.5 | 12.5 | 3.13 | 12.5 |
| *Aci. antitratus* A-6 | 1.56 | 1.56 | 0.78 | 0.39 | 3.13 |
| *St. aureus* F-137* | 3.13 | 3.13 | 0.78 | 0.1 | 6.25 |
| *E. coli* TK-3* | 6.25 | 3.13 | 3.13 | 3.13 | 3.13 |
| *E. coli* GN5482** | 0.39 | 0.2 | 0.2 | 0.1 | 0.39 |
| *Kl. pneumoniae* Y-4* | 25 | 12.5 | 12.5 | 6.25 | 25 |
| *Pro. vulgaris* GN76** | 3.13 | 3.13 | 3.13 | 0.78 | 1.56 |
| *Ps. aeruginosa* GN918** | 100 | 50 | 50 | 12.5 | 25 |
| *Ps. aeruginosa* GN3379* | 25 | 25 | 25 | 25 | 50 |

| Compound R² / Strain R³ | 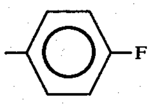 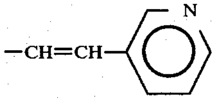 | 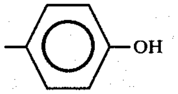 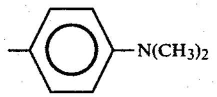 | 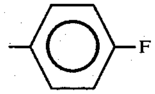 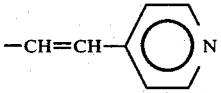 | 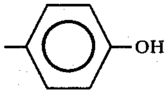 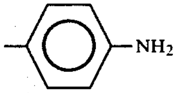 |
|---|---|---|---|---|
| *St. aureus* FDA209P | 3.13 | 0.2 | 12.5 | 3.13 |
| *E. coli* NIHJ JC-2 | 1.56 | 0.2 | 12.5 | 3.13 |
| *E. coli* TK-111 | 0.78 | 0.05 | 0.39 | 0.78 |
| *Kl. pneumoniae* Y-50 | 0.78 | 0.2 | 0.78 | 3.13 |
| *Kl. pneumoniae* Y-41 | 6.25 | 0.78 | 6.25 | 12.5 |
| *Ent. cloacae* IID977 | 3.13 | 0.39 | 3.13 | 12.5 |
| *Pro. vulgaris* GN3027 | 0.39 | 0.1 | 0.2 | 0.39 |
| *Pro. morganii* T-216 | 6.25 | 0.78 | 6.25 | 3.13 |
| *Ps. aeruginosa* IFO3445 | 25 | 3.13 | 50 | 25 |
| *Ps. aeruginosa* S-68 | 12.5 | 3.13 | 12.5 | 25 |
| *Pro. mirabilis* T-111 | 12.5 | 1.56 | 12.5 | 25 |
| *Aci. antitratus* A-6 | 3.13 | 0.39 | 12.5 | 25 |
| *St. aureus* F-137* | 3.13 | 0.1 | 12.5 | 6.25 |
| *E. coli* TK-3* | 3.13 | 0.39 | 1.56 | 3.13 |
| *E. coli* GN5482** | 0.2 | 0.05 | 0.2 | 0.1 |
| *Kl. pneumoniae* Y-4* | 6.25 | 1.56 | 6.25 | 12.5 |

TABLE 1-continued

| | | | | |
|---|---|---|---|---|
| *Pro. vulgaris* GN76** | 1.56 | 0.39 | 0.78 | 1.56 |
| *Ps. aeruginosa* GN918** | 12.5 | 1.50 | 25 | 25 |
| *Ps. aeruginosa* GN3379* | 25 | 3.13 | 25 | 25 |

Note:
*1 DL-glutamic acid salt of 2-dimethylaminoethyl ester
*2 L-aspartic acid salt of 2-dimethylaminoethyl ester
*3 2,3-Dihydroxy-n-propyl ester
*4 2-Dimethylaminoethyl ester
*5 Methoxymethyl ester
*6 2-Dimethylaminoethyl ester 2. Acute toxicity test The $LD_{50}$ values of the representative compounds of this invention when administered intravenously to mice (ICR strain, male, 18-24 g) are shown in Table 2.

TABLE 2

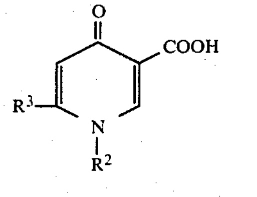

| $R^3$ | $R^2$ | $LD_{50}$ (mg/kg) |
|---|---|---|
| 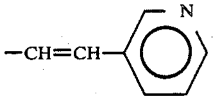 | 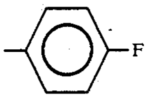 | >200 |
| 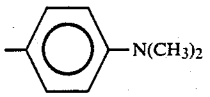 | 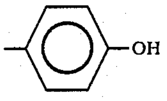 | >200 |
| 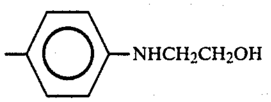 | 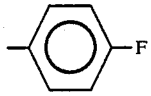 | >200 |
| 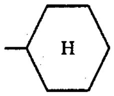 | 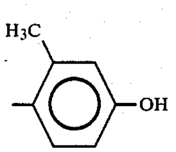 | >200 |

Next, the process for producing the compound of this invention is explained below.

The compound of this invention can be produced in the manner known per se, and a representative production process is explained in detail below.

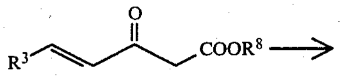

[II]

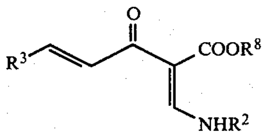

[III]

-continued

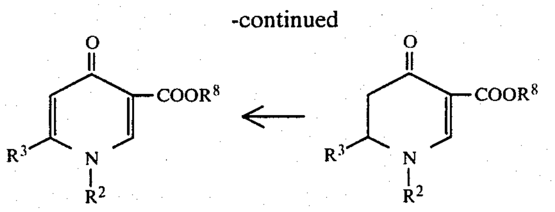

[Ib] [IV]

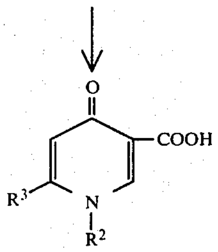

[Ia]

In the above formulas, $R^2$ and $R^3$ have the same meanings as defined above, and $R^8$ represents a carboxyl-protecting group as explained for $R^1$.

The compound represented by the formula [II] can be produced by a conventional method, for example, the Wittig reaction using a corresponding $R^3CHO$ as the starting material. This compound is reacted with N,N-dimethylformamidodimethylacetal or N,N-dimethylformamidodiethylacetal, and thereafter, the reaction product is reacted with $R^2NH_2$ to obtain a compound represented by the formula [III]. The solvent which are used in this reaction may be any solvent inert to the reaction, for example, an aromatic hydrocarbon such as benzene, toluene, xylene or the like; an ether such as dioxane, tetrahydrofuran, anisole, diethyleneglycol dimethyl ether, dimethyl Cellosolve or the like; a halogenated hydrocarbon, such as methylene chloride, chloroform, dichloroethane or the like; an amide such as N,N-dimethylformamide, N,N-dimethylacetamide or the like; or a sulfoxide such as dimethylsulfoxide or the like. The amount of the acetal used is preferably 1 mole or more, more preferably 1.0 to 1.2 moles, per mole of the compound represented by the formula [II], and this reaction is usually completed at a temperature of 0° C. to 80° C. in a period of 10 minutes to 10 hours. In order to subsequently react the product with $R^2NH_2$, the same solvent as mentioned above is used, and the amine is used in an amount of one mole per mole of the compound represented by the formula [II]. The reaction is conducted at a temperature of 0° C. to 100° C. for a period of 30 minutes to 10 hours.

As an alternative method, there is a method which comprises reacting the compound represented by the formula [II] with ethyl orthoformate or methyl orthoformate in acetic anhydride, and thereafter, reacting the product with $R^2NH_2$ to obtain the compound represented by the formula [III]. In this case, the orthoformic acid ester is used in an amount of one mole or more, preferably 1.0 to 1.2 moles, per mole of the compound represented by the formula [II] and the reaction is conducted at a temperature of 20° C. to 100° C. for a period of 5 minutes to 10 hours. Subsequently, the reaction product is reacted with $R^2NH_2$ in a proportion of one mole or more, preferably 1.0 to 1.2 moles, per mole of the compound represented by the formula [II], in the presence of the above-mentioned solvent or in the absence of any solvent, to obtain the compound represented by the formula [III].

The compound represented by the formula [IV] is produced by subjecting the compound represented by the formula [III] to ring-closure reaction. This reaction is conducted in the presence or absence of a solvent such as an amide, for example, N,N-dimethylformamide, N,N-dimethylacetamide or the like, a sulfoxide, for example, dimethylsulfoxide or the like; or a phosphoric acid ester, for example, ethyl polyphosphate or the like, and is preferably completed at a temperature of 50° C. to 150° C. for a period of 1 hour to 10 hours.

Further, the compound represented by the formula [IB] is produced by reacting the compound represented by the formula [IV] with a dehydrogenating agent. As this dehydrogenating agent, there may be used all dehydrogenating agents which can conventionally be used, preferably 2,3-dichloro-5,6-dicyano-p-benzoquinone, 2,3,5,6-tetrachloro-p-benzoquinone, 3,4,5,6-tetrachloro-o-benzoquinone or the like, and this dehydrogenating agent may be used in a proportion of one mole or more, preferably 1.0 to 1.2 moles, per mole of the compound represented by the formula [IV]. This reaction is usually conducted in a solvent, and preferable examples of the solvent are aromatic hydrocarbons, such as benzene, toluene, xylene and the like; and ethers such as dioxane, tetrahydrofuran, anisole, diethylene glycol dimethyl ether, dimethyl Cellosolve and the like. Said reaction is completed at a temperature of 0° C. to 100° C. in a period of 1 minute to 10 hours.

The compound thus obtained is hydrolyzed by a conventional method, for example, hydrolyzed at a temperature of 0° C. to 100° C. for a period of 5 minutes to 10 hours in the presence of an alkali or an acid, thereby obtaining the compound represented by the formula [Ia].

In producing the compounds represented by the formula [Ia] or [Ib] via the above-mentioned reaction route, the compound represented by the formula [III] and/or the compound represented by the formula [IV] can be subjected to the subsequent reaction without being isolated.

When the compounds represented by the formula [II], [III], [IV] and [Ib] have active groups, for example, hydroxyl group, amino group, carboxyl group or the like in other sites than the reactive sites, the active groups are previously protected by a protecting group in a conventional manner, and the protecting group is removed after the completion of the reaction in a conventional manner to produce the above compounds.

The compounds thus produced may be, if desired, subjected to a reaction known per se, such as halogenation, esterification, amidation, ureidation, alkylation, alkenylation, alkylidenation, acylation, hydroxylation, iminomethylation, reduction or the like, to derive other compounds therefrom, and hence, have uses as intermediates.

When the compound of this invention is used as a medicine the compound is formed into tablet, capsule, powder, syrup, granule, suppository, ointment, injection or the like in a conventional manner using a proper carrier which is usually used in the formation of a preparation. The administration method, dose and administration time may be varied depending upon symptoms of patients, and usually, the compound may be administered to an adult orally or parenterally (administration by injection or administration to rectal region) in a dose of 0.1 to 100 mg/Kg/day in terms of the compound represented by the formula [I] at one time or in several portions.

This invention is further explained in more detail below referring to Referential Examples, Examples and Preparation Examples.

REFERENTIAL EXAMPLE 1

In 20 ml of methanol were dissolved 1.6 g of benzo[b]thiophene-2-aldehyde and 5.1 g of [2-methoxy-3-(methoxycarbonyl)allyl]triphenylphosphonium bromide, and to this solution was added dropwise 2.1 g of a 28% by weight solution of sodium methoxide in methanol with stirring at room temperature over 10 minutes. This mixture was further reacted at the same temperature for 20 minutes, and the solvent was then removed by distillation under reduced pressure. To the residue was added 20 ml of water, and the resulting mixture was extracted with 20 ml of chloroform. The extract was dried with anhydrous magnesium sulfate and the solvent was removed by distillation under reduced pressure. The residue was purified by a column chromatography (Wako Silica Gel C-200; eluent: benzene/n-hexane (3:1 by volume) mixture) to obtain an oily substance. This oily substance was dissolved in 12 ml of dioxane, and to the resulting solution was added 12 ml of 0.1N sulfuric acid. The resulting mixture was subjected to reaction at 100° C. for 1.5 hours. This reaction mixture was then cooled to room temperature and 20 ml of water was added thereto, after which the precipitated crystals were collected by filtration. These crystals were washed with water and then dried to obtain 1.1 g of methyl 5-(2-benzo-[b]thienyl)-3-oxo-4-pentenoate having a melting point of 105°-107° C.

IR (KBr) $cm^{-1}$: $\nu_{C=O}$ 1625.

The compounds shown in Table 3 were obtained in the same manner.

TABLE 3

| | $R^3CH{=}CHCOCH_2COOCH_3$ | |
|---|---|---|
| $R^3$ | $R^3$ | $R^3$ |
| 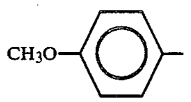 | 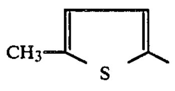 | 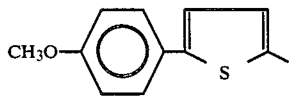 |
| 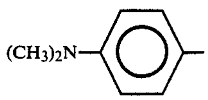 | 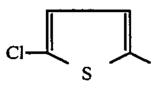 | 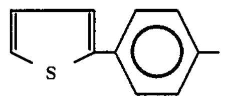 |

TABLE 3-continued
$R^3CH{=}CHCOCH_2COOCH_3$
| $R^3$ | $R^3$ | $R^3$ |
|---|---|---|
| 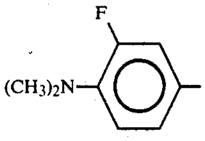 | 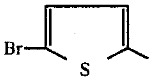 | 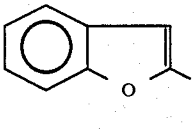 |
| 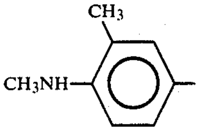 | 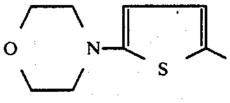 | 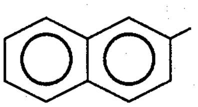 |
| 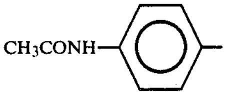 | 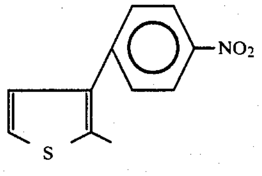 | 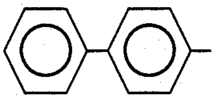 |
| 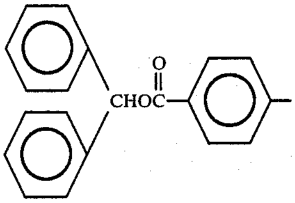 | 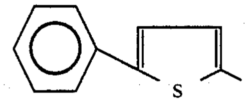 | 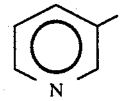 |
| 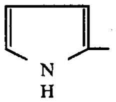 | 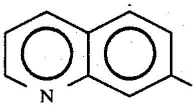 | 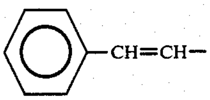 |
| 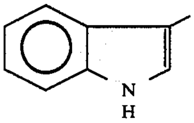 | 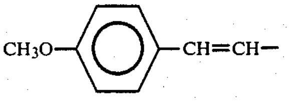 | 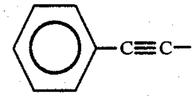 |
| 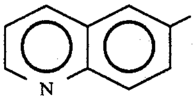 | 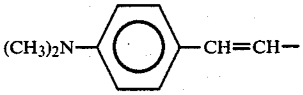 | 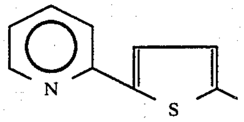 |
| 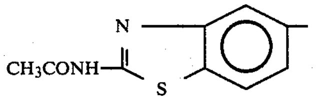 | 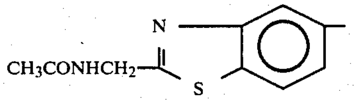 | 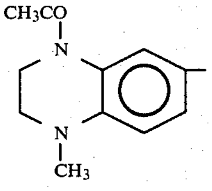 |
| 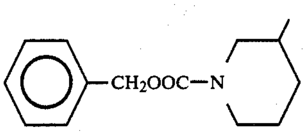 | 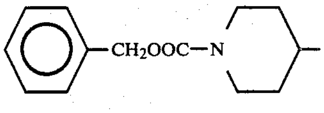 | 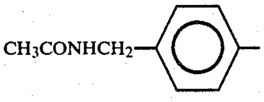 |
| 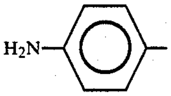 | 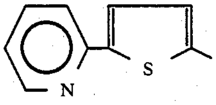 | 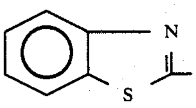 |

TABLE 3-continued
$R^3CH{=}CHCOCH_2COOCH_3$
| $R^3$ | $R^3$ | $R^3$ |
|---|---|---|
| 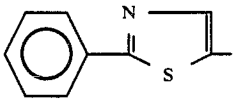 | 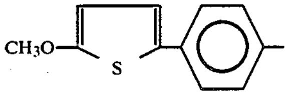 | 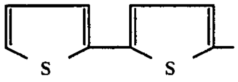 |
| 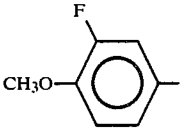 | 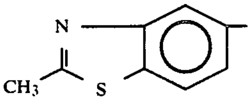 | 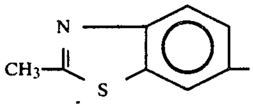 |
| 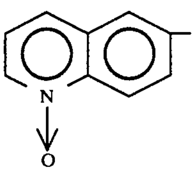 | 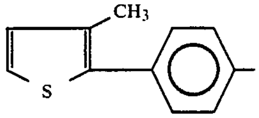 | 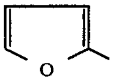 |
| 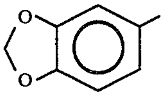 | 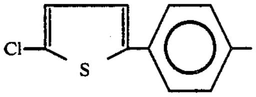 | 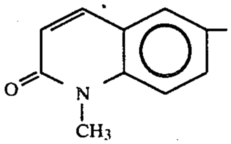 |
| 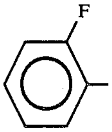 | 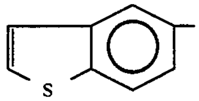 | 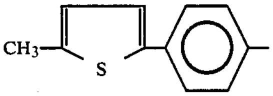 |
| 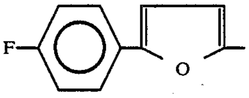 | 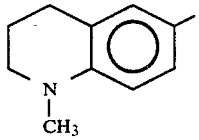 | 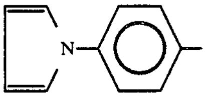 |
| 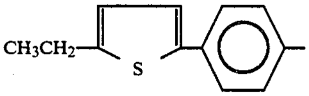 | 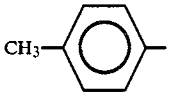 | 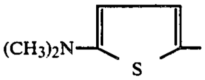 |
| 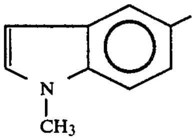 | 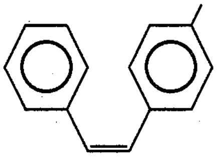 | 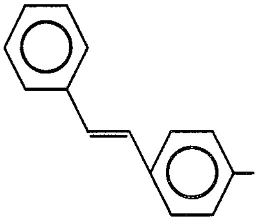 |
| 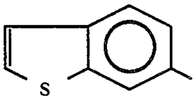 | 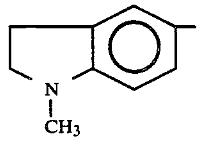 | 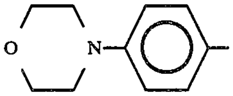 |
| 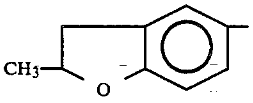 | 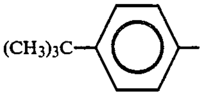 | 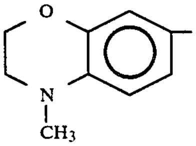 |

TABLE 3-continued
| $R^3CH{=}CHCOCH_2COOCH_3$ | | |
|---|---|---|
| $R^3$ | $R^3$ | $R^3$ |
| 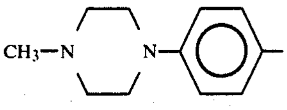 | 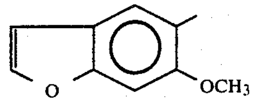 | 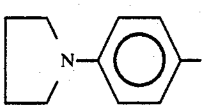 |
| 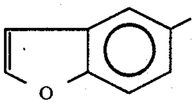 | 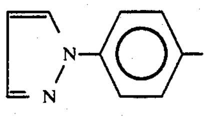 | 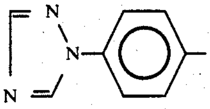 |
| 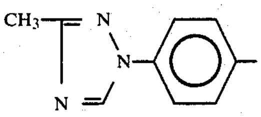 | 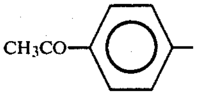 | 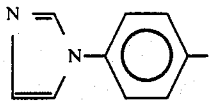 |
| 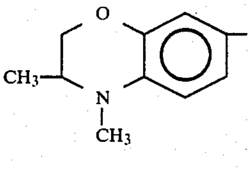 | 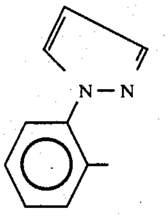 | 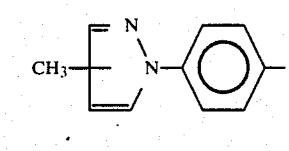 |
| 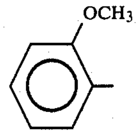 | 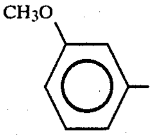 | 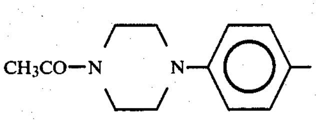 |
| 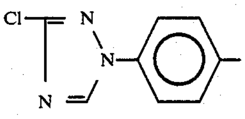 | 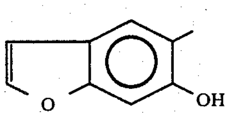 | 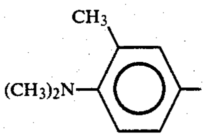 |
| 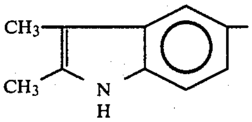 | 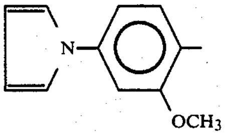 | 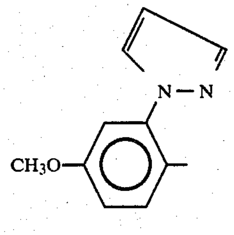 |
| 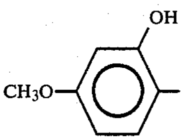 | 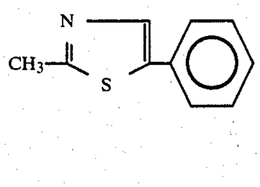 | 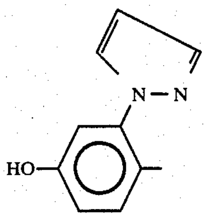 |
| 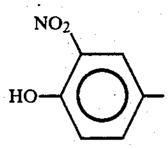 | 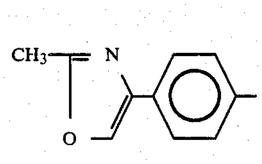 | 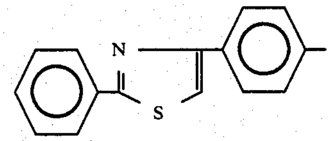 |

TABLE 3-continued

| R³ | R³ | R³ |
|---|---|---|
| | $R^3CH{=}CHCOCH_2COOCH_3$ | |
| 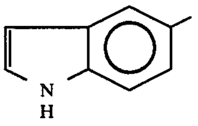 | 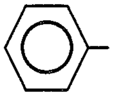 | 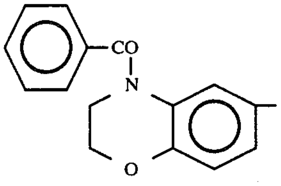 |
| 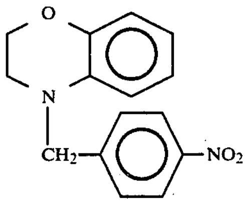 | $(CH_3)_2NCH_2$— 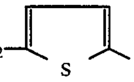 | |

REFERENTIAL EXAMPLE 2

In 100 ml of methanol was dissolved 25.7 g of [2-methoxy-3-(methoxycarbonyl)allyl]triphenylphosphonium bromide, and to this solution was added dropwise 10.5 g of a 28% by weight solution of sodium methoxide in methanol with stirring at room temperature over 10 minutes. To the mixed solution was then further added 5 g of 1,2,3,6-tetrahydrobenzaldehyde at room temperature and the resulting mixture was subjected to reaction at the same temperature for 2 hours. After completion of the reaction, the solvent was removed by distillation under reduced pressure, and to the residue was added 50 ml of water. The resulting mixture was extracted with 50 ml of chloroform. The extract was dried with anhydrous magnesium sulfate, and the solvent was then removed by distillation under reduced pressure. The residue was purified by a column chromatography (Wako Silica Gel C-200; eluent: benzene/n-haxane (3:1 by volume) mixture) to obtain an oily substance. This oily substance was dissolved in 100 ml of dioxane, and to the solution was then added 100 ml of 0.1N sulfuric acid. The resulting mixture was subjected to reaction at 100° C. for 1.5 hours. The solvent was then removed by distillation under reduced pressure, and to the residue was added 100 ml of chloroform. The resulting mixture was washed with 100 ml of water. The organic layer was separated, and dried with anhydrous magnesium sulfate and then the solvent was removed by distillation under reduced pressure. The residue was purified by a column chromatography (Wako Silica Gel C-200; eluent: benzene/n-hexane (3:1 by volume) mixture) to obtain 7.5 g of oily methyl 5-(cyclohexen-4-yl)-3-oxo-4-pentenoate.

IR (neat) $cm^{-1}$: $\nu_{C=O}$ 1740

The compounds shown in Table 4 were obtained in the same manner.

TABLE 4

| R³ | R³ | R³ |
|---|---|---|
| | $R^3CH{=}CHCOCH_2COOCH_3$ | |
| 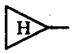 | 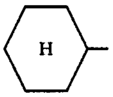 | 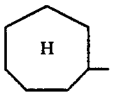 |
| 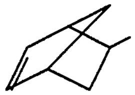 | 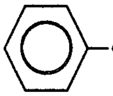—$CH_2CH_2$— | 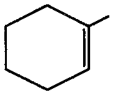 |
| 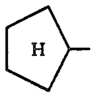 | $H_3CCH{=}CH$—(trans) | 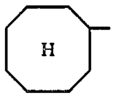 |
| 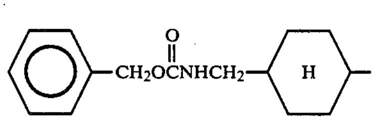 | 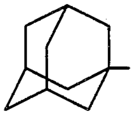 | $ClCH_2CH_2$— |

TABLE 4-continued

| $R^3CH{=}CHCOCH_2COOCH_3$ | | |
|---|---|---|
| $R^3$ | $R^3$ | $R^3$ |
| 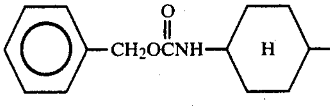 | 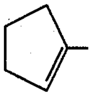 | 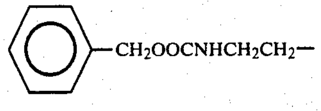 |
| 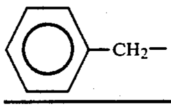 | 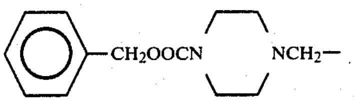 | 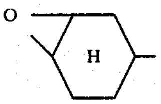 |

EXAMPLE 1

(1) In 10 ml of benzene was dissolved 2.0 g of methyl 5-(4-chlorophenyl)-3-oxo-4-pentenoate, and to this solution was added 1.2 g of N,N-dimethylformamidodimethylacetal. The resulting mixture was subjected to reaction at 70° C. for 1.5 hours. The reaction mixture was cooled to room temperature, and 1.12 g of p-fluoroaniline was then added thereto, after which the resulting mixture was further subjected to reaction for 1.5 hours. After completion of the reaction, 10 ml of diethyl ether was added to the reaction mixture, and the precipitated crystals were collected by filtration, and washed with 10 ml of diethyl ether to obtain 2.2 g of methyl 5-(4-chlorophenyl)-2-(4-fluorophenylaminomethylene)-3-oxo-4-pentenoate having a melting point of 166°-168° C.

IR (KBr) $cm^{-1}$: $\nu_{C=O}$ 1700.

The compounds shown in Table 5 were obtained in the same manner.

TABLE 5

$R^3CH{=}CHCOC({=}CHNHR^2)COOCH_3$

| $R^3$ | $R^2$ | m.p. (°C.) | IR (KBr) $cm^{-1}$: $\nu_{C=O}$ |
|---|---|---|---|
| 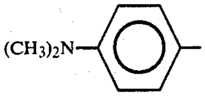 | 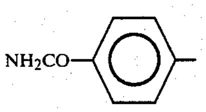 | 133-136 | 1680 |
| 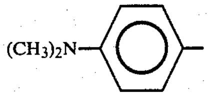 | 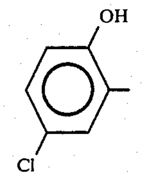 | 235-236 | 1685 |
| 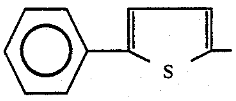 | 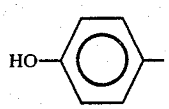 | 214-217 | 1705 |
| 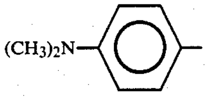 | 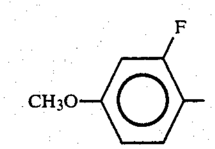 | 160-165 | 1690 |
| 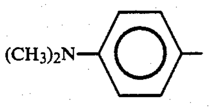 | 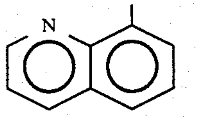 | 193-195 | 1690 |
| 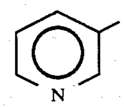 | 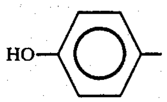 | 185-187 | 1690 |

TABLE 5-continued $R^3CH{=}CHCOC({COOCH_3}){=}CHNHR^2$

| $R^3$ | $R^2$ | m.p. (°C.) | IR (KBr) $cm^{-1}$: $\nu_{C=O}$ |
|---|---|---|---|
| 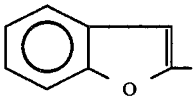 | 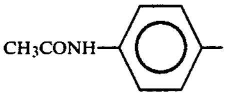 | 201-203 | 1700, 1660 |
| 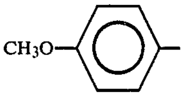 | 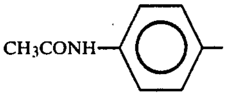 | 194-195 | 1685 |
| 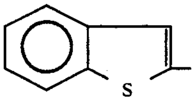 | 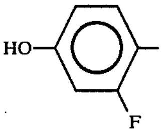 | 196-197 | 1690, 1665 |
| 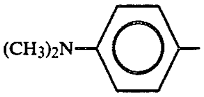 | 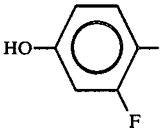 | 170-172 | 1690, 1660 |

(2) In 15 ml of N,N-dimethylformamide was dissolved 2.0 g of methyl 5-(4-chlorophenyl)-2-(4-fluorophenylaminomethylene)-3-oxo-4-pentenoate, and they were reacted at 140° C. for 4 hours. After completion of the reaction, the solvent was removed by distillation under reduced pressure, and the residue was purified by a column chromatography (Wako Silica Gel C-200; eluent: benzene/ethyl acetate (3:1 by volume) mixture) to obtain 1.1 g of oily methyl 6-(4-chlorophenyl)-1-(4-fluorophenyl)-4-oxo-1,4,5,6-tetrahydronicotinate.

IR (neat) $cm^{-1}$: $\nu_{C=O}$ 1725

NMR ($CDCl_3$) δ values: 2.5-3.5 (2H, m, $C_5$—H), 3.80 (3H, s, —$COOCH_3$), 5.30 (1H, m, $C_6$—H), 7.0-7.5 (8H, m,

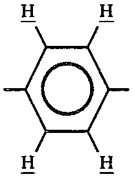 × 2), 8.65 (1H, s, $C_2$—H)

The compounds shown in Table 6 were obtained in the same manner.

TABLE 6

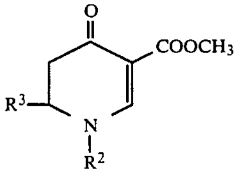

| $R^3$ | $R^2$ | m.p. (°C.) | IR (KBr) $cm^{-1}$: $\nu_{C=O}$ |
|---|---|---|---|
| 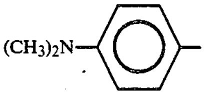 | 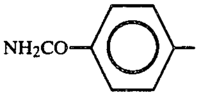 | 145-148 | 1720, 1660 |
| 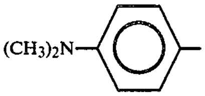 | 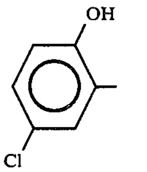 | 202-205 | 1730, 1700 |

TABLE 6-continued

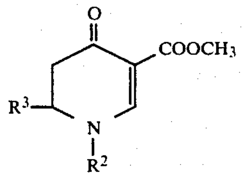

| $R^3$ | $R^2$ | m.p. (°C.) | IR (KBr) $cm^{-1}$: $\nu_{C=O}$ |
|---|---|---|---|
| 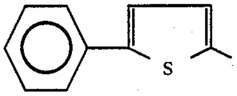 | 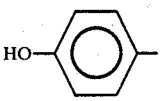 | 210-212 | 1720 |
| 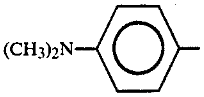 | 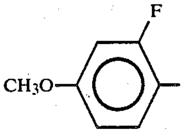 | Oily substance | 1720 [neat] |
| 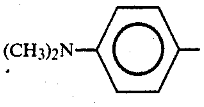 | 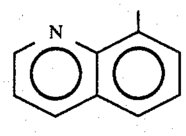 | — | 1690 |
| 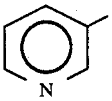 | 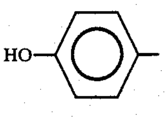 | 102-110 (decomp.) | 1725, 1710 |
| 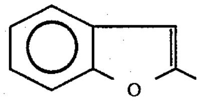 | 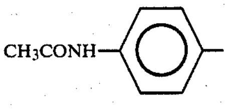 | 128-131 | 1710, 1665 |
| 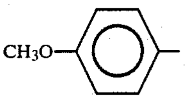 | 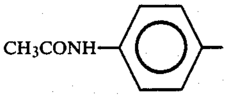 | 128-131 | 1720, 1710 1660 |
| 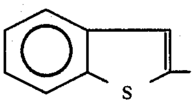 | 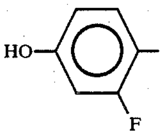 | — | 1720, 1710 |
| 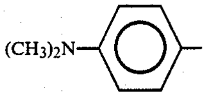 | 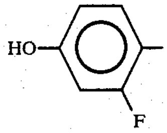 | — | 1715 |

(3) In 20 ml of benzene was dissolved 1.0 g of methyl 6-(4-chlorophenyl)-1-(4-fluorophenyl)-4-oxo-1,4,5,6-tetrahydronicotinate, and to the resulting solution was added a mixed solution of 0.7 g of 2,3-dichloro-5,6-dicyano-p-benzoquinone and 5 ml of benzene at 80° C., after which they were reacted at the same temperature for 30 minutes. After completion of the reaction, the solvent was removed from the reaction mixture by distillation under reduced pressure, and the residue was suspended in 30 ml of chloroform and 30 ml of water This suspension was adjusted to a pH of 7.5 with sodium hydrogencarbonate, and the organic layer was then separated and washed successively with 30 ml of water and 30 ml of a saturated aqueous solution of sodium chloride, and then dried with anhydrous magnesium sulfate. The solvent was removed by distillation under reduced pressure to obtain 0.85 g of methyl 6-(4-chlorophenyl)-1-(4-fluorophenyl)-4-oxo-1,4-dihydronicotinate having a melting point of 250°-254° C.

IR (KBr) $cm^{-1}$: $\nu_{C=O}$ 1735.

The compounds shown in Table 7 were obtained in the same manner.

TABLE 7
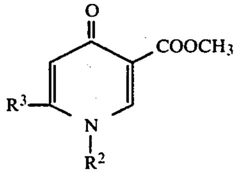
| $R^3$ | $R^2$ | m.p. (°C.) | IR (KBr) $cm^{-1}$: $\nu_{C=O}$ |
|---|---|---|---|
| 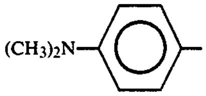 | 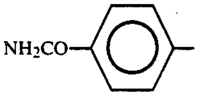 | 153-155 | 1725, 1670 |
| 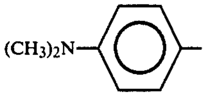 | 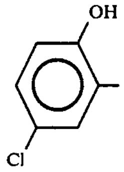 | 192-196 | 1730, 1710 |
| 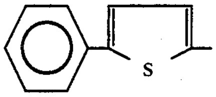 | 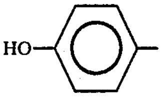 | >250 | 1700 |
| 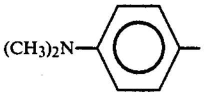 | 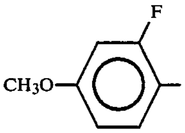 | 108-110 | 1730, 1700 |
| 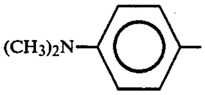 | 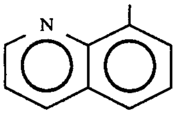 | — | 1725, 1700 |
| 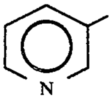 | 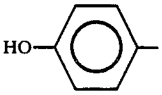 | >250 | 1730, 1690 |
| 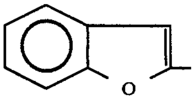 | 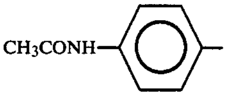 | >250 | 1710, 1680 |
| 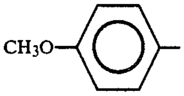 | 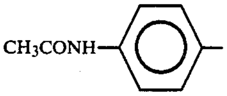 | 189-191 | 1730, 1700, 1670 |
| 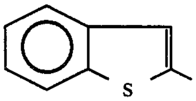 | 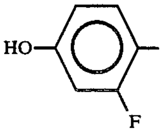 | >250 | 1730, 1700 |
| 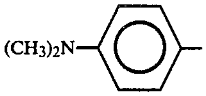 | 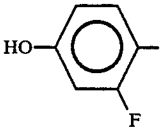 | >250 | 1725, 1705 |

(4) In a mixed solvent of 5 ml of methanol and 5 ml of 1N aqueous sodium hydroxide solution was dissolved 0.5 g of methyl 6-(4-chlorophenyl)-1-(4-fluorophenyl)-4-oxo-1,4-dihydronicotinate, and they were reacted at room temperature for 30 minutes. After completion of the reaction, the reaction mixture was adjusted to a pH of 5.5 with acetic acid, and the precipitated crystals were collected by filtration, washed with 10 ml of water and dried to obtain 0.4 g of 6-(4-chlorophenyl)-1-(4-fluorophenyl)-4-oxo-1,4-dihydronicotinic acid having a melting point of 199°-204° C.

IR (KBr) $cm^{-1}$: $\nu_{C=O}$ 1725.

The compounds shown in Table 8 were obtained in the same manner.

TABLE 8

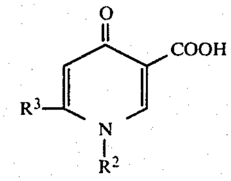

| $R^3$ | $R^2$ | m.p. (°C.) | IR (KBr) $cm^{-1}$: $\nu_{C=O}$ |
|---|---|---|---|
| 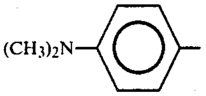 | 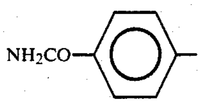 | 278-280 | 1720, 1680 1665 |
| 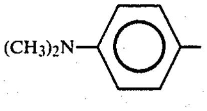 | 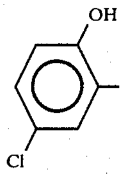 | >250 | 1720 |
| 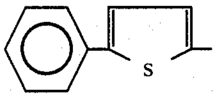 | 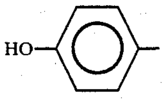 | >250 | 1750 |
| 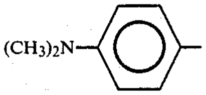 | 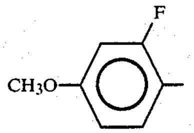 | 173-180 | 1720 |
| 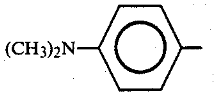 | 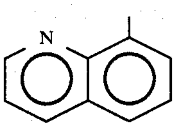 | 268-271 | 1720, 1700 |
| 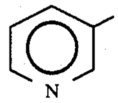 | 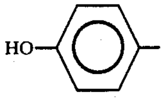 | >250 | 1715 |
| 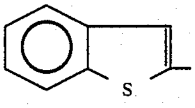 | 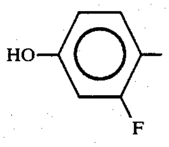 | >250 | 1720 |
| 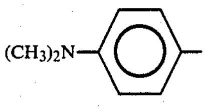 | 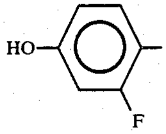 | >250 | 1720 |

EXAMPLE 2

(1) In 25 ml of methylene chloride were dissolved 3.1 g of 2-naphthaldehyde and 9.4 g of [2-methoxy-3-(methoxycarbonyl)allyl]triphenylphosphonium bromide, followed by addition thereto of 19 ml of a 50% by weight aqueous sodium hydroxide solution with stirring at room temperature, and the mixture was subjected to reaction at the same temperature for 20 minutes. After completion of the reaction, the methylene chloride layer was separated from the reaction mixture and washed with water. It was then dried with anhydrous sodium sulfate, and the solvent was removed by distillation under reduced pressure. To the residue was added 30 ml of diethyl ether, and the insolubles were removed by filtration, after which the filtrate was concentrated to obtain an oily substance. This oily substance was dissolved in a mixed solvent of 45 ml of dioxane and 40 ml of 0.1N sulfuric acid, and the solution was refluxed for 30 minutes. Then the reaction mixture was cooled to room temperature, extracted with 100 ml of ethyl acetate and the extract was dried with anhydrous sodium sulfate. The solvent was removed by distillation under reduced pressure, and the formed crystals were suspended in 50 ml of benzene, and to the suspension was added 2.4 g of N,N-dimethylformamidodimethylacetal, and the resulting mixture was subjected to reaction at 60° C. for 30 minutes. The reaction mixture was cooled to room temperature, and 2.2 g of p-aminophenol was added thereto. The mixture was subjected to reaction at the same temperature for 2 hours. The precipitated crystals were collected by filtration, washed with 5 ml of benzene and dried to obtain 1.7 g of methyl 2-(4-hydroxyphenylaminomethylene)-5-(2-naphthyl)-3-oxo-4-pentenoate having a melting point of 191°-192.5° C.

IR (KBr) $cm^{-1}$: $\nu_{C=O}$ 1710.

The compounds shown in Table 9 were obtained in the same manner.

TABLE 9

$R^3CH{=}CHCOC{=}CHNHR^2$
$\qquad\qquad\quad|$
$\qquad\qquad COOCH_3$

| $R^3$ | $R^2$ | m.p. (°C.) | IR (KBr) $cm^{-1}$: $\nu_{C=O}$ |
|---|---|---|---|
| 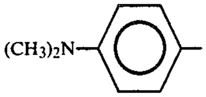 | 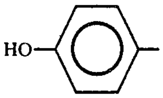 | 172-175 | 1685 |
| 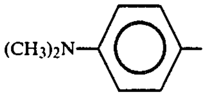 | 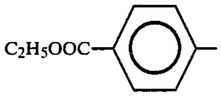 | 153-159 | 1720, 1705 |
| 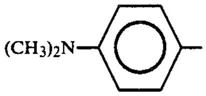 | 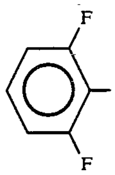 | 146-148 | 1700 |
| 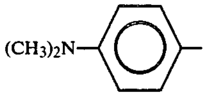 | 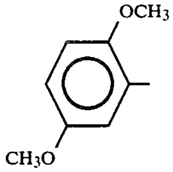 | 157-159 | 1700, 1685 |
| 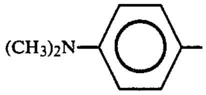 | 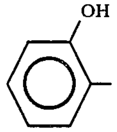 | 199-201 | 1685 |
| 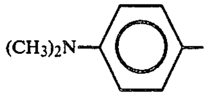 | 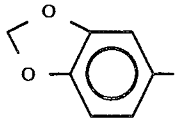 | 195-196 | 1700 |
| 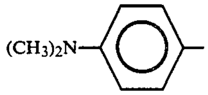 | 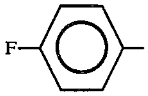 | 131-133 | 1685 |

TABLE 9-continued
$R^3CH{=}CHCOC{=}CHNHR^2$
$\quad\quad\quad\quad\quad\quad|$
$\quad\quad\quad\quad\quad COOCH_3$
| $R^3$ | $R^2$ | m.p. (°C.) | IR (KBr) $cm^{-1}$: $\nu_{C=O}$ |
|---|---|---|---|
| 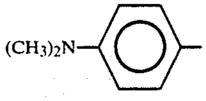 | 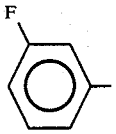 | 141–143 | 1705 |
| 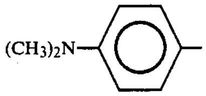 | 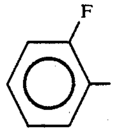 | 141–142 | 1690 |
| 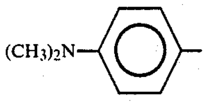 | 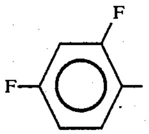 | 167–168 | 1700 |
| 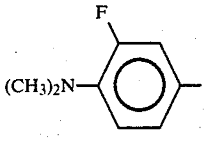 | 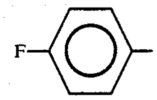 | 118–120 | 1690 |
| 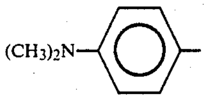 | 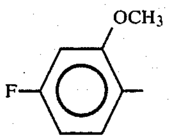 | 156–158 | 1685 |
| 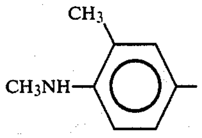 | 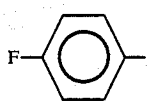 | 134–135 | 1675 |
| 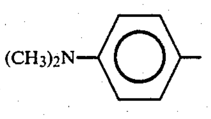 | 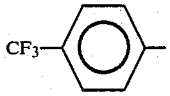 | 173–175 | 1705 |
| 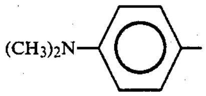 | 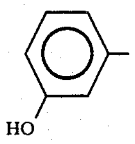 | 156–158 | 1670 |
| 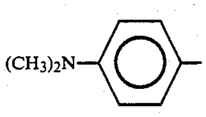 | 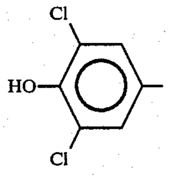 | 189–191 | 1685 |
| 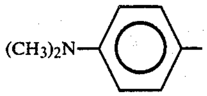 | 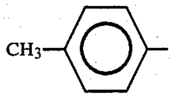 | 153–154 | 1695 |

TABLE 9-continued
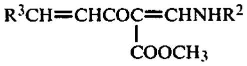
| $R^3$ | $R^2$ | m.p. (°C.) | IR (KBr) $cm^{-1}$: $\nu_{C=O}$ |
|---|---|---|---|
| 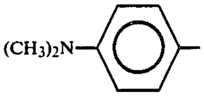 | 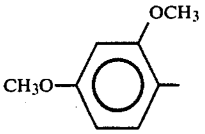 | 154–156 | 1680 |
| 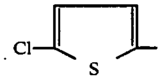 | 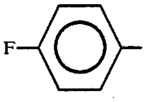 | 152–153 | 1700 |
| 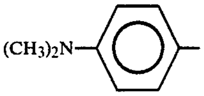 | 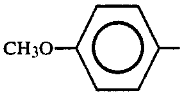 | 154–157 | 1690 |
| 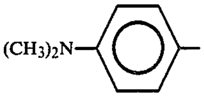 | 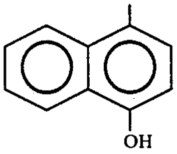 | 188–190 | 1700 |
| 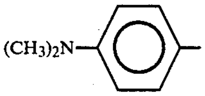 | 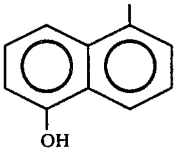 | 234–236 | 1695 |
| 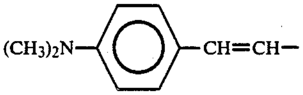 | 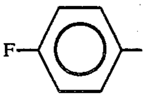 | 166–168 | 1710, 1695 |
| 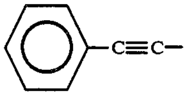 | 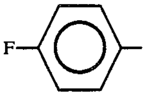 | 149–151 | 2190($\nu_{C \equiv C}$), 1705 |
| 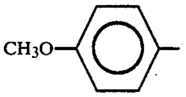 | 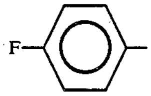 | 128–131 | 1730 |
| 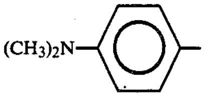 | 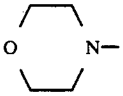 | 153–155 | 1690 |
| 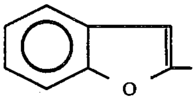 | 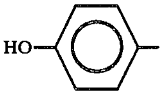 | 220–222 | 1710 |
| 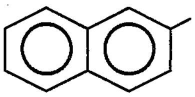 | 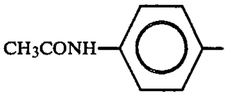 | 178–182 | 3320($\nu_{NH}$), 1710, 1695, 1670 |

TABLE 9-continued
$R^3CH{=}CHCOC{=}CHNHR^2$
$\quad\quad\quad\quad\quad\quad\quad | $
$\quad\quad\quad\quad\quad\quad COOCH_3$
| $R^3$ | $R^2$ | m.p. (°C.) | IR (KBr) $cm^{-1}$: $\nu_{C=O}$ |
|---|---|---|---|
| 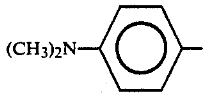 | 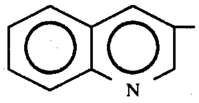 | 212–214 | 1690 |
| 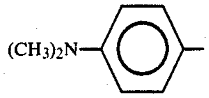 | 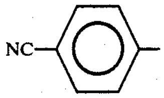 | 140–143 | 2220($\nu_{CN}$), 1685 |
| 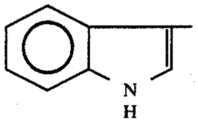 | 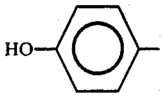 | 217–222 | 1680 |
| 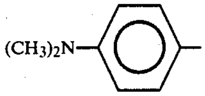 | 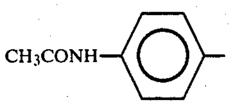 | 197–199 | 3300($\nu_{NH}$), 1685, 1630 |
| 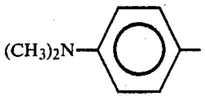 | 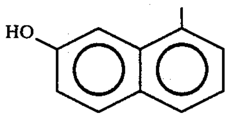 | 192–194 | 1665 |
| 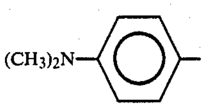 | 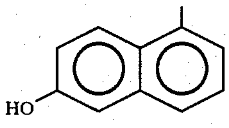 | 204–205 | 1675 |
| 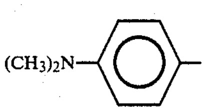 | 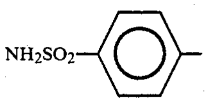 | 180–185 | 1705, 1675 |
| 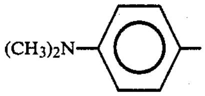 | 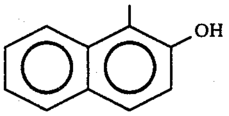 | 206–207 | 1690 |
| 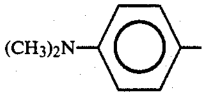 | 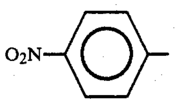 | 134–136 | 1700, 1685 |
| 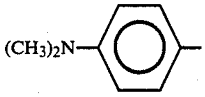 | 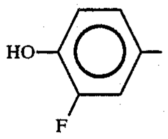 | 179–182 | 1685 |
| 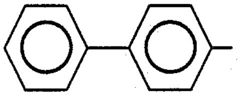 | 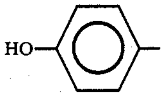 | 180–184 | 1710 |

TABLE 9-continued $R^3CH=CHCOC=CHNHR^2$
$COOCH_3$

| $R^3$ | $R^2$ | m.p. (°C.) | IR (KBr) $cm^{-1}$: $\nu_{C=O}$ |
|---|---|---|---|
| 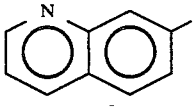 | 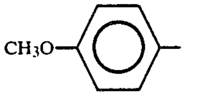 | 151.5-152.5 | 1700 |
| 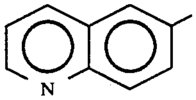 | 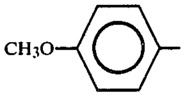 | 157-158 | 1710 |
| 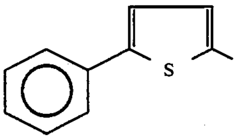 | 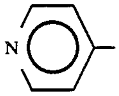 | 154-156 | 1700 |
| 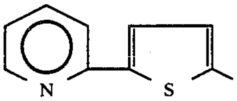 | 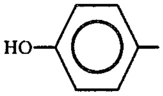 | 220-223 | 1700 |
| 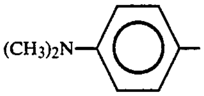 | 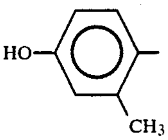 | 163-167 | 1655 |
| 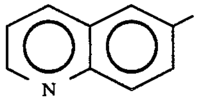 | 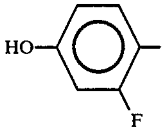 | 231-234 | 1695 |
| 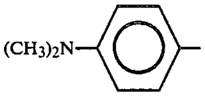 | 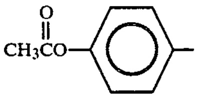 | 188-191 | 1705, 1665 |

(2) In 12 ml of N,N-dimethylformamide was dissolved 1.7 g of methyl 2-(4-hydroxyphenylaminomethylene)-5-(2-naphthyl)-3-oxo-4-pentenoate, and they were reacted at 140° C. for 2 hours. After completion of the reaction, the solvent was removed by distillation under reduced pressure, and the residue was purified by a column chromatography (Wako Silica Gel C-200; eluent: chloroform/methanol (19:1 by volume) mixture). The purified oily substance was dissolved in 15 ml of dioxane and the resulting solution was heated to 80° C. To this solution was added dropwise at 80° C. a solution formed by dissolving 1.1 g of 2,3,5,6-tetrachloro-p-benzoquinone in 15 ml of dioxane. After this addition was completed, the solvent was removed by distillation under reduced pressure, and to the residue was added 20 ml of a chloroform/methanol (5:1 by volume) mixed solvent. The crystals thus formed were collected by filtration, washed with 5 ml of the same mixed solvent as mentioned above, and then dried to obtain 0.75 g of methyl 1-(4-hydroxyphenyl)-6-(2-naphthyl)-4-oxo-1,4-dihydronicotinate having a melting point of 280° C. or more.

IR (KBr) $cm^{-1}$: $\nu_{C=O}$ 1730, 1710.

The compounds shown in Table 10 were obtained in the same manner.

TABLE 10
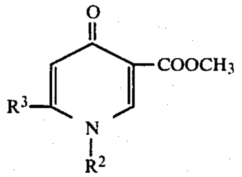
| $R^3$ | $R^2$ | m.p. (°C.) | IR (KBr) $cm^{-1}$: $\nu_{C=O}$ |
|---|---|---|---|
| 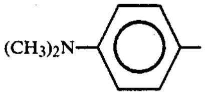 | 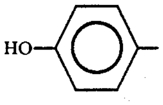 | >280 | 1725, 1700 |
| 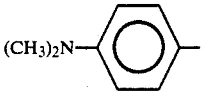 | 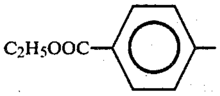 | 205–209 | 1740, 1720, 1700 |
| 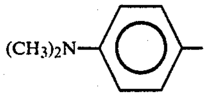 | 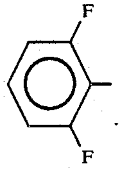 | 228–231 | 1705 |
| 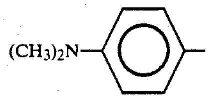 | 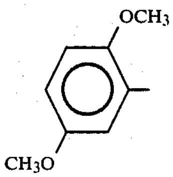 | 241–243 | 1730, 1700 |
| 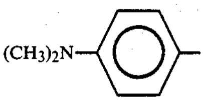 | 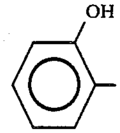 | 272–274 | 1730, 1700 |
| 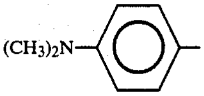 | 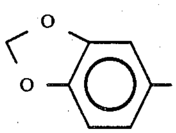 | 281.5–283.5 | 1735, 1700 |
| 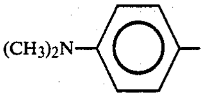 | 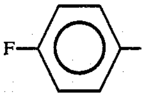 | 248–249 | 1730, 1720 |
| 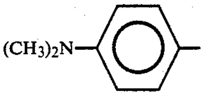 | 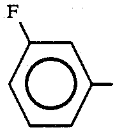 | 275–276 | 1735, 1700 |
| 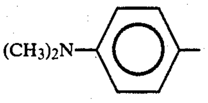 | 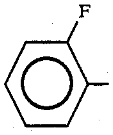 | 216–217 | 1730, 1700 |

TABLE 10-continued
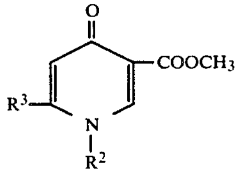
| $R^3$ | $R^2$ | m.p. (°C.) | IR (KBr) $cm^{-1}$: $\nu_{C=O}$ |
|---|---|---|---|
| 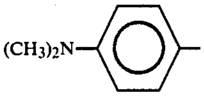 | 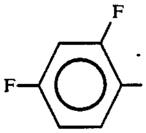 | 147-148 | 1725, 1700 |
| 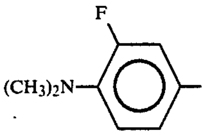 | 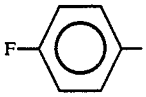 | 275-277 | 1730, 1710 |
| 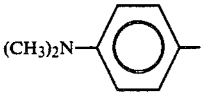 | 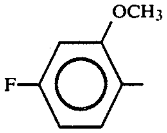 | 168-170 | 1730, 1700 |
| 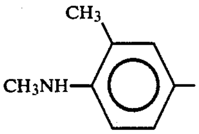 | 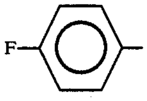 | 236-238 | 1730, 1700 |
| 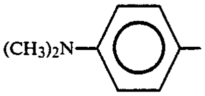 | 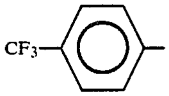 | >280 | 1735 |
| 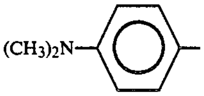 | 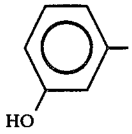 | >280 | 1725, 1705 |
| 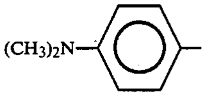 | 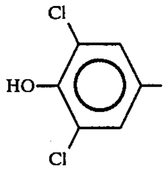 | >280 | 1730, 1700 |
| 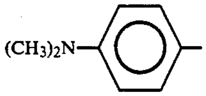 | 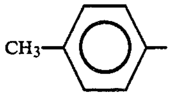 | 249-250 | 1730, 1700 |
| 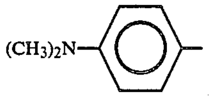 | 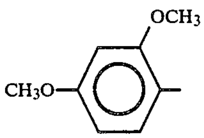 | 221-222 | 1725 |
| 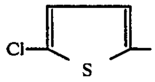 | 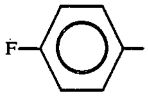 | 246-248 | 1735 |

TABLE 10-continued
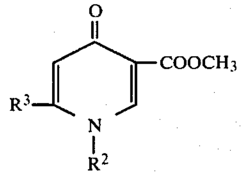
| $R^3$ | $R^2$ | m.p. (°C.) | IR (KBr) $cm^{-1}$: $\nu_{C=O}$ |
|---|---|---|---|
| 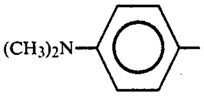 | 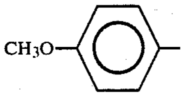 | 232–234 | 1735, 1700 |
| 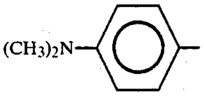 | 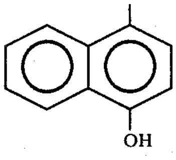 | 228–238 | 1730, 1700 |
| 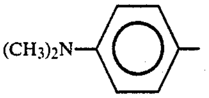 | 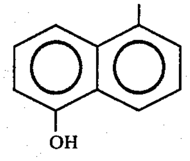 | >250 | 1730, 1705 |
| 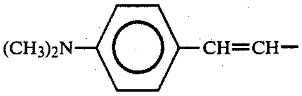 | 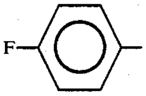 | NMR($d_6$-DMSO)δ values:<br>2.95 (6H, s,<br>$-N(C\underline{H_3})_2$), 3.74 (3H,<br>s, $-COO\underline{CH_3}$), 6.10 (1H,<br>d, J=16 Hz,<br>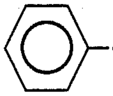 $-C\underline{H}=CH-$), 6.54–7.90 (9H, m,<br>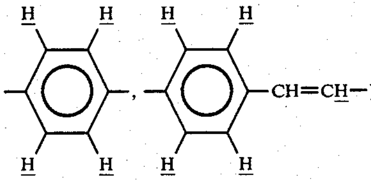 $-CH=C\underline{H}-$),<br>6.76 (1H, s, $C_5-H$),<br>8.20 (1H, s, $C_2-H$) | |
| 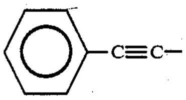 | 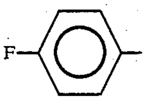 | 156–160 | 2220($\nu_{C\equiv C}$), 1730 |
| 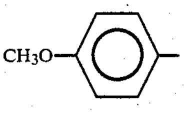 | 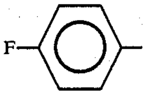 | >250 | 1730 |
| 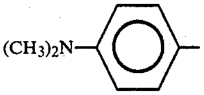 | 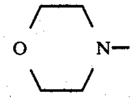 | >260 | 1735, 1720 |
| 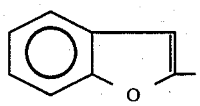 | 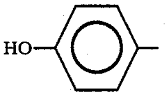 | >250 | 1690 |

TABLE 10-continued
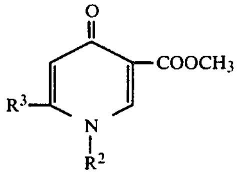
| $R^3$ | $R^2$ | m.p. (°C.) | IR (KBr) $cm^{-1}$: $\nu_{C=O}$ |
|---|---|---|---|
| 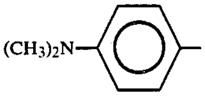 | 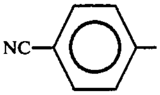 | 226-228 | 2230($\nu_{CN}$), 1735, 1700 |
| 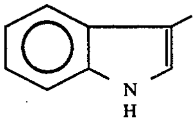 | 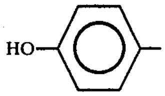 | >250 | 1715 |
| 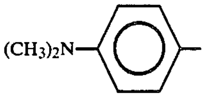 | 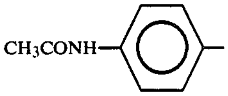 | 279-280 | 1715, 1685 |
| 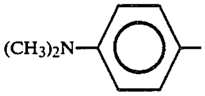 | 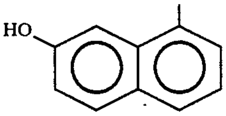 | >280 | 1725, 1700 |
| 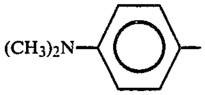 | 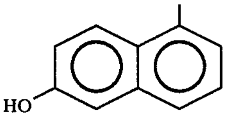 | >280 | 1720, 1700 |
| 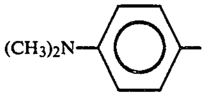 | 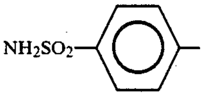 | 180-181 | 1730, 1700 |
| 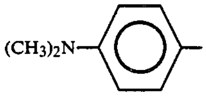 | 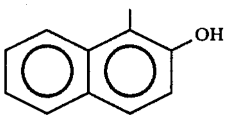 | 198-206 | 1725, 1700 |
| 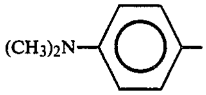 | 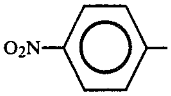 | 213-217 | 1730, 1700 |
| 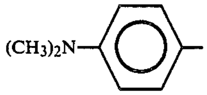 | 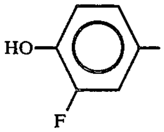 | >280 | 1725, 1700 |
| 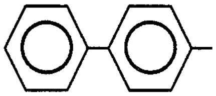 | 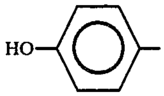 | >280 | 1725, 1700 |

TABLE 10-continued

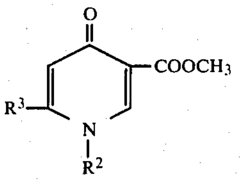

| $R^3$ | $R^2$ | m.p. (°C.) | IR (KBr) $cm^{-1}$: $\nu_{C=O}$ |
|---|---|---|---|
| 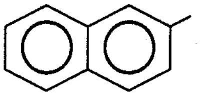 | 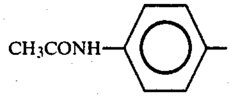 | 167-170 | 1725, 1680 |
| 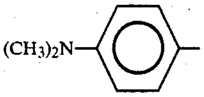 | 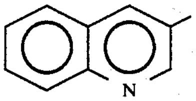 | >280 | 1735, 1700 |
| 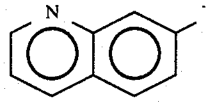 | 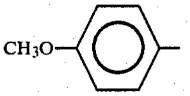 | 263-265 | 1735, 1705 |
| 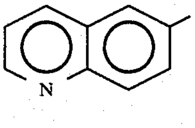 | 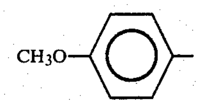 | 205.5-206.5 | 1730, 1700 |
| 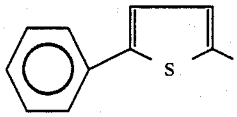 | 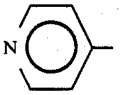 | 233-235 | 1730, 1700 |
| 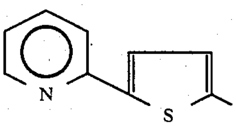 | 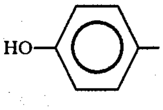 | >250 | 1700 |
| 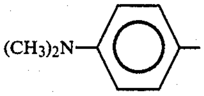 | 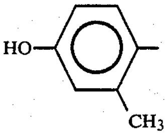 | 246-248 | 1730, 1700 |
| 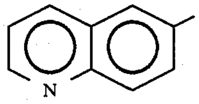 | 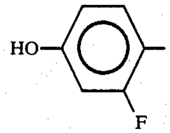 | >250 | 1730, 1710 |
| 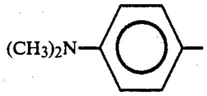 | 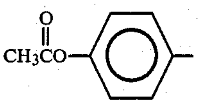 | 236-238 | 1730, 1680 |

EXAMPLE 3

(1) To 2.5 g of methyl 5-(4-acetaminophenyl)-3-oxo-4-pentenoate were added 2.0 g of acetic anhydride and 1.4 g of ethyl orthoformate, and they were reacted at 80° C. for one hour. The resulting ethyl acetate was removed by distillation under reduced pressure, and the residue was dissolved in 15 ml of benzene, and to the resulting solution was added 1.1 g of p-fluoroaniline and they were reacted at room temperature for one hour. After completion of the reaction, the precipitated crystals were collected by filtration, washed with 10 ml of benzene and then dried to obtain 2.9 g of methyl 2-(4-fluorophenylaminomethylene)-5-(4-acetaminophenyl)-

3-oxo-4-pentenoate having a melting point of 161°-164° C.
IR (KBr) $cm^{-1}$: $\nu_{C=O}$ 1705, 1660.
The compounds shown in Table 11 were obtained in the same manner.
TABLE 11
$R^3CH{=}CHCOC{=}CHNHR^2$
|
$COOCH_3$
| $R^3$ | $R^2$ | m.p. (°C.) | IR (KBr) $cm^{-1}$: $\nu_{C=O}$ |
|---|---|---|---|
| 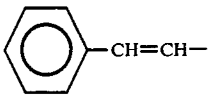 | 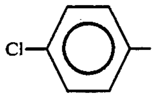 | 180-181 | 1700 |
| 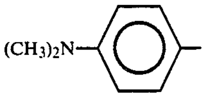 | 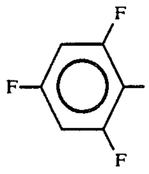 | 161-163 | 1705 |
| 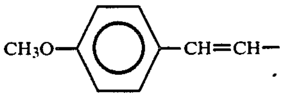 | 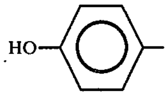 | — | 1725, 1700 |
| 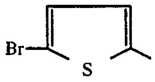 | 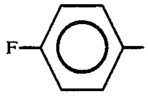 | 155-157 | 1703 |
| 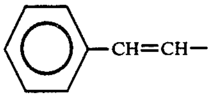 | 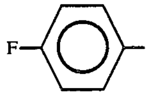 | 178-179.5 | 1690 |
| 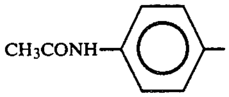 | 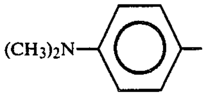 | — | 3300($\nu$NH) 1690, 1660 [neat] |
| 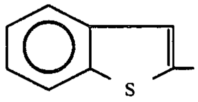 | 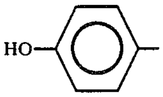 | 180-182 | 1625 |
| 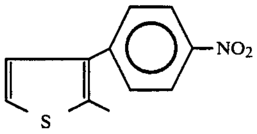 | 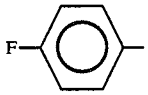 | 204-206 | 1703 |
| 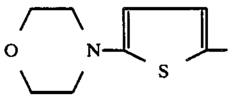 | 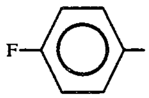 | 153-156 | 1690 |
| 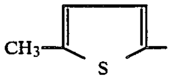 | 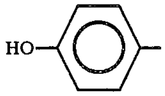 | 197-199 | 1700 |
| 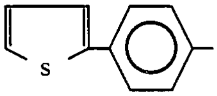 | 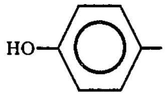 | 183-186 | 1700 |

TABLE 11-continued

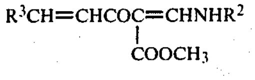

| $R^3$ | $R^2$ | m.p. (°C.) | IR (KBr) $cm^{-1}$: $\nu_{C=O}$ |
|---|---|---|---|
| 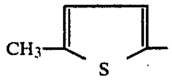 | 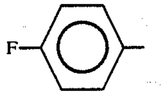 | 122-125 | 1690 |

(2) In 25 ml of N,N-dimethylformamide was dissolved 2.9 g of methyl 2-(4-fluorophenylaminomethylene)-5-(4-acetaminophenyl)-3-oxo-4-pentenoate, and they are reacted at 140° C. for 2 hours. After completion of the reaction, the solvent was removed by distillation under reduced pressure and the residue was purified by a column chromatography (Wako Silica Gel C-200; eluent: chloroform) to obtain an oily substance. This oily sugstance was dissolved in 30 ml of benzene, followed by dropwise addition thereto of a solution of 2.06 g of 2,3,5,6-tetrachloro-p-benzoquinone in 18 ml of benzene at 80° C. After completion of this dropwise addition, the reaction mixture was cooled to room temperature, and the precipitated crystals were collected by filtration and washed with 30 ml of benzene. These crystals were then dissolved in a mixed solution of 20 ml of methanol and 20 ml of a 1N aqueous sodium hydroxide solution, and they were reacted at room temperature for 30 minutes. The reaction solution was adjusted to a pH of 6.0 with acetic acid and the precipitated crystals were collected by filtration, washed with water and dried to obtain 2.3 g of 6-(4-acetaminophenyl)-1-(4-fluorophenyl)-4-oxo-1,4-dihydronicotinic acid having a melting point of 249°-250° C.

IR (KBr) $cm^{-1}$: $\nu_{C=O}$ 1720.

The compounds shown in Table 12 were obtained in the same manner.

TABLE 12

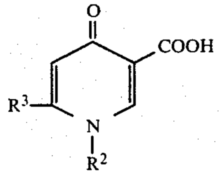

| $R^3$ | $R^2$ | m.p. (°C.) | IR (KBr) $cm^{-1}$: $\nu_{C=O}$ |
|---|---|---|---|
| 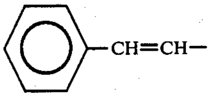 | 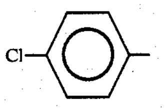 | 240-242 | 1725, 1710 |
| 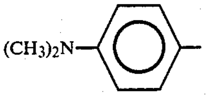 | 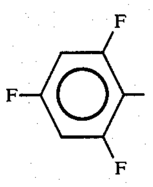 | 218-221 | 1730 |
| 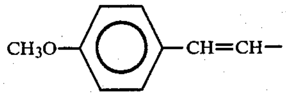 | 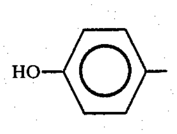 | — | 1720, 1700 |
| 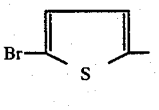 | 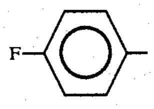 | 204-206 | 1700 |
| 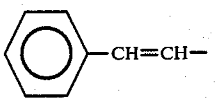 | 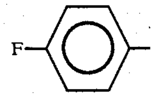 | >250 | 1725, 1705 |
| 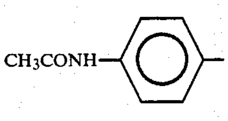 | 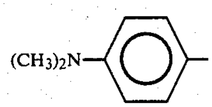 | 165-168 | 1730, 1685 |

TABLE 12-continued

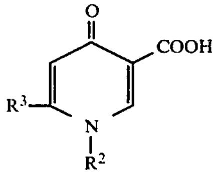

| $R^3$ | $R^2$ | m.p. (°C.) | IR (KBr) $cm^{-1}$: $\nu_{C=O}$ |
|---|---|---|---|
| 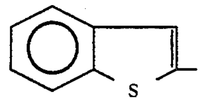 | 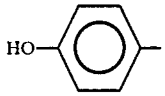 | >250 | 1720 |
| 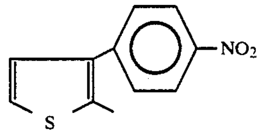 | 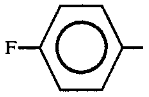 | >250 | 1720 |
| 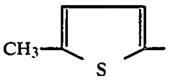 | 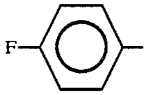 | 182-184 | 1715 |
| 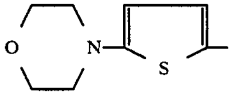 | 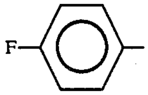 | >250 | 1720, 1710 |
| 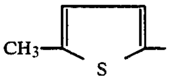 | 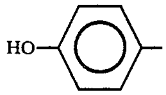 | >250 | 1715 |
| 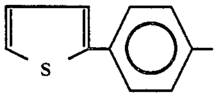 | 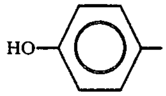 | >250 | 1720 |

EXAMPLE 4

In 10 ml of N,N-dimethylformamide was dissolved 2.0 g of methyl 5-(3-methyl-4-dimethylaminophenyl)-3-oxo-4-pentenoate, and 1.1 g of N,N-dimethylformamidodimethylacetal was added to the resulting solution, after which they were reacted at 70° C. for 1.5 hours. To the reaction mixture was then added 1.0 g of p-fluoroaniline at 70° C., and they were reacted at 80° C. for 2 hours and further at 140° C. for 3 hours. After completion of the reaction, the reaction mixture was cooled to room temperature and the solvent was removed by distillation under reduced pressure. The residue was purified by a column chromatography (Wako Silica Gel C-200; eluent: chloroform) to obtain an oily substance. This oily substance was dissolved in 30 ml of dioxane, and to this solution was added dropwise a solution of 2.1 g of 2,3-dichloro-5,6-dicyano-p-benzoquinone in 10 ml of benzene at 80° C. Thereafter, the mixture was subjected to reaction at the same temperature for 30 minutes and the solvent was removed by distillation under reduced pressure. The residue was suspended in 50 ml of chloroform and 50 ml of water, and after adjusting this suspension to a pH 7.5 with sodium hydrogencarbonate, the organic layer was separated, washed successively with 10 ml of water and 20 ml of a saturated aqueous solution of sodium chloride and then dried with anhydrous magnesium sulfate. The solvent was removed by distillation under reduced pressure to obtain 1.8 g of methyl 1-(4-fluorophenyl)-6-(3-methyl-4-dimethylaminophenyl)-4-oxo-1,4-dihydronicotinate having a melting point of 217°-220° C.

IR (KBr) $cm^{-1}$: $\nu_{C=O}$ 1725, 1705.

The compounds shown in Table 13 were obtained in the same manner.

TABLE 13
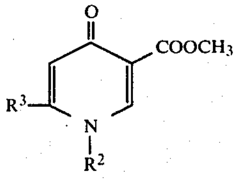
| $R^3$ | $R^2$ | m.p. (°C.) | IR(KBr) $cm^{-1}$: $\nu_{C=O}$ |
|---|---|---|---|
| 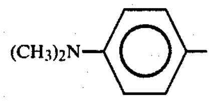 | 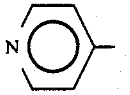 | >260 | 1735, 1720 |
| 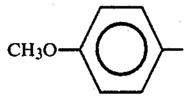 | 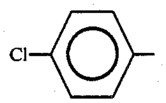 | >250 | 1730 |
| 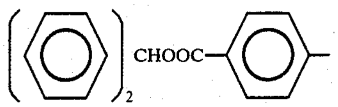 | 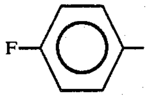 | 195-197 | 1720, 1700 |
| 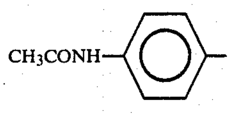 | 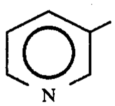 | 167-171 | 1730, 1680 |
| 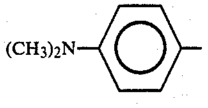 | 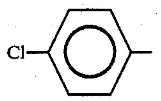 | 156-166 | 1710, 1685 |
| 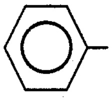 | 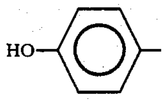 | >250 | 1690 |
| 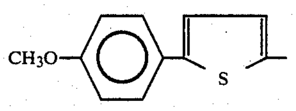 | 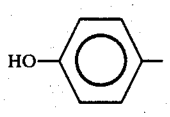 | >250 | 1705 |
| 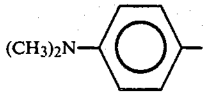 | 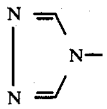 | 251-254 | 1720, 1700 |
| 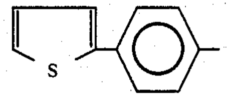 | 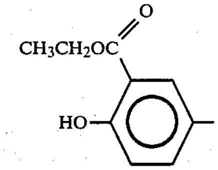 | 126-129 | 1735, 1695, 1675 |
| 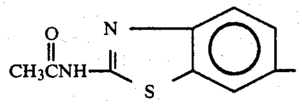 | 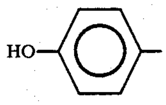 | >250 | 1720, 1690 |
| 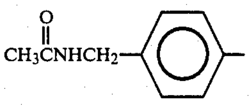 | 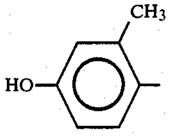 | 266-268 | 1725 |

TABLE 13-continued
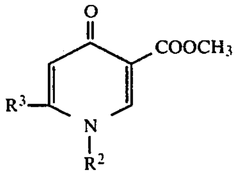
| $R^3$ | $R^2$ | m.p. (°C.) | IR(KBr) $cm^{-1}$: $\nu_{C=O}$ |
|---|---|---|---|
| 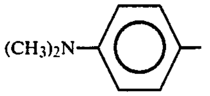 | 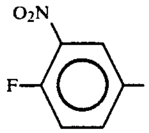 | >250 | 1735, 1700 |
| 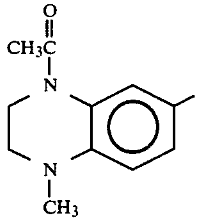 | 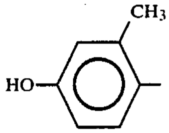 | >250 | 1730, 1700 |
| 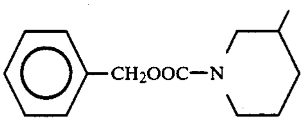 | 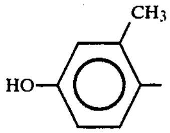 | 136-137.5 | 1730, 1710, 1695 |
| 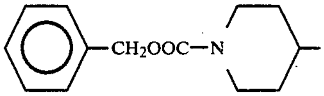 | 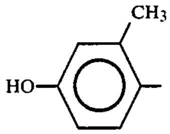 | 125-127 | 1735, 1705, 1695 |
| 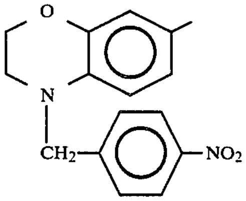 | 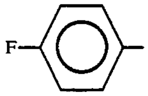 | — | 1725, 1700 |
EXAMPLE 5
(1) In the same manner as in Example 1-(4), the corresponding methyl esters were hydrolyzed to obtain the compounds shown in Table 14.
TABLE 14
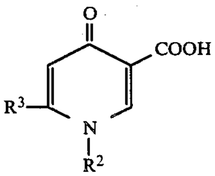
| $R^3$ | $R^2$ | m.p. (°C.) | IR (KBr) $cm^{-1}$: $\nu_{C=O}$ |
|---|---|---|---|
| 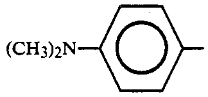 | 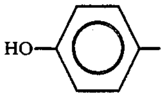 | >280 | 1725, 1700 |

TABLE 14-continued
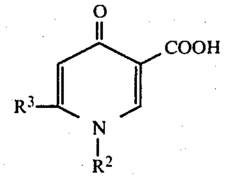
| R3 | R2 | m.p. (°C.) | IR (KBr) $cm^{-1}$: $\nu_{C=O}$ |
|---|---|---|---|
| 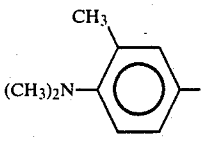 | 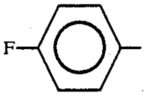 | 212–214 | 1720, 1700 |
| 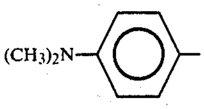 | 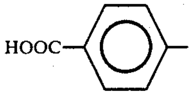 | 228.5–231 | 1710, 1690 |
| 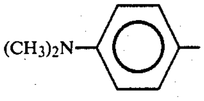 | 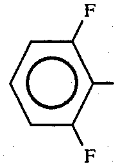 | 230–231 | 1720, 1700 |
| 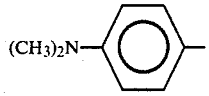 | 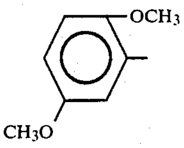 | 238–240 | 1720, 1700 |
| 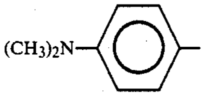 | 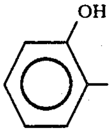 | >280 | 1725, 1705 |
| 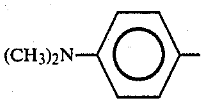 | 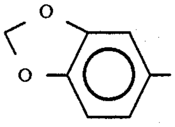 | 226–228 | 1720, 1700 |
| 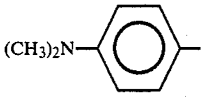 | 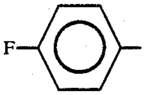 | 230–231 | 1720, 1700 |
| 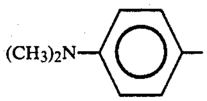 | 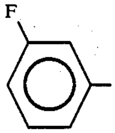 | 243–245 | 1720, 1700 |
| 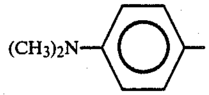 | 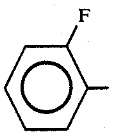 | 217–218 | 1720, 1700 |

TABLE 14-continued
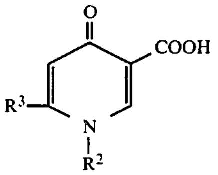
| $R^3$ | $R^2$ | m.p. (°C.) | IR (KBr) cm$^{-1}$: $\nu_{C=O}$ |
|---|---|---|---|
| 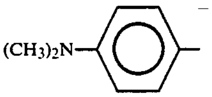 | 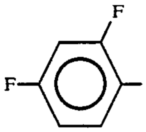 | 197–199 | 1725, 1700 |
| 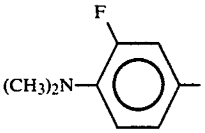 | 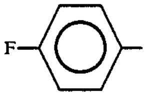 | 255–257 | 1720, 1705 |
| 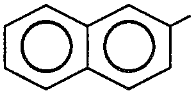 | 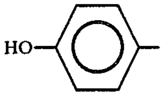 | >260 | 1745, 1715 |
| 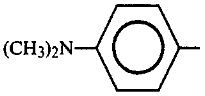 | 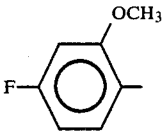 | 192–195 | 1725, 1700 |
| 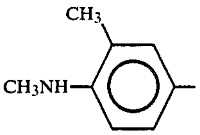 | 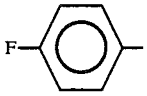 | 166–167 | 3420, ($\nu_{NH}$), 1725, 1705 |
| 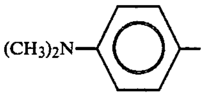 | 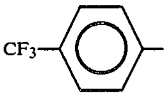 | 180–182 | 1725, 1700 |
| 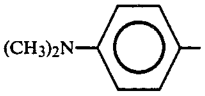 | 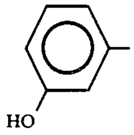 | 252–255 | 1725, 1705 |
| 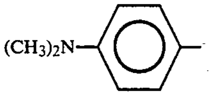 | 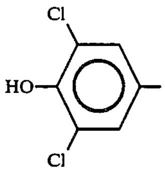 | >290 | 1725, 1705 |
| 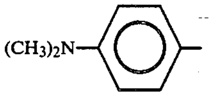 | 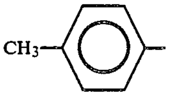 | 201–203 | 1715 |
| 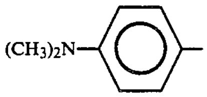 | 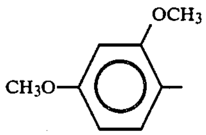 | 181–185.5 | 1720, 1700 |

TABLE 14-continued
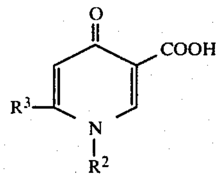
| $R^3$ | $R^2$ | m.p. (°C.) | IR (KBr) cm$^{-1}$: $\nu_{C=O}$ |
|---|---|---|---|
| 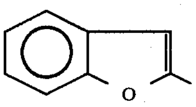 | 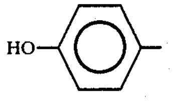 | >250 | 1730 |
| 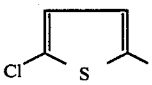 | 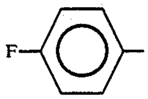 | 169-171 | 1725, 1700 |
| 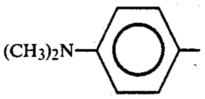 | 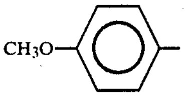 | 224-225 | 1715 |
| 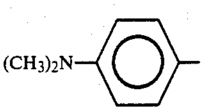 | 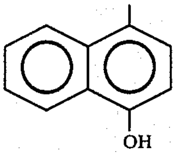 | >250 | 1730, 1710 |
| 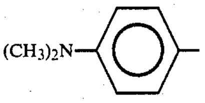 | 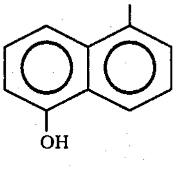 | >250 | 1725 |
| 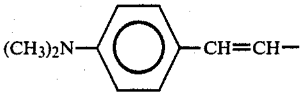 | 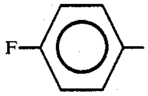 | >230 | 1725, 1705 |
| 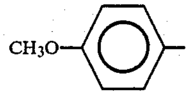 | 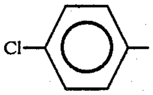 | >260 | 1710 |
| 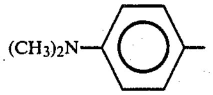 | 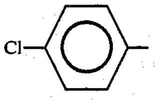 | 223-225 | 1705 |
| 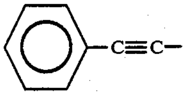 | 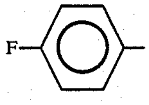 | 242-246 | 2220 ($\nu_{C \equiv C}$), 1710 |
| 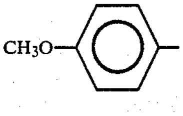 | 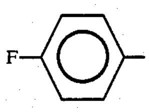 | 202-203 | 1695 |
| 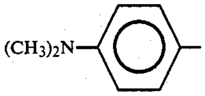 | 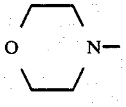 | >260 | 1725, 1700 |

TABLE 14-continued
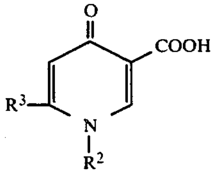
| $R^3$ | $R^2$ | m.p. (°C.) | IR (KBr) $cm^{-1}$: $\nu_{C=O}$ |
|---|---|---|---|
| 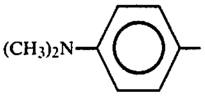 | 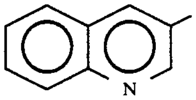 | 207–209 | 1720, 1700 |
| 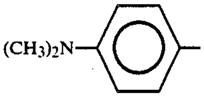 | 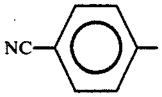 | 273–275 | 2225 ($\nu_{CN}$), 1725, 1700 |
| 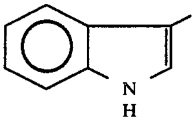 | 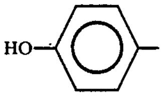 | 196–201 | 1710 |
| 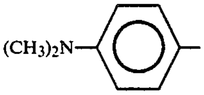 | 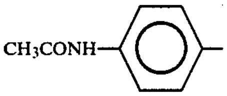 | 272–273 | 3270 ($\nu_{CN}$), 1720, 1705, 1685 |
| 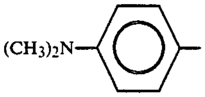 | 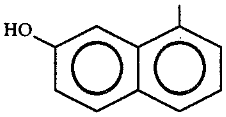 | 180–182 | 1725, 1700 |
| 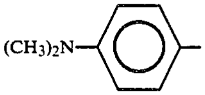 | 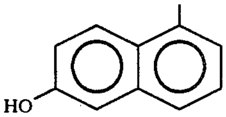 | >280 | 1725, 1710 |
| 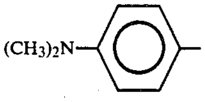 | 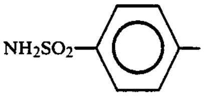 | 255–257 | 1720, 1700 |
| 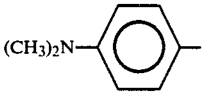 | 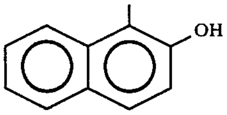 | >250 | 1710 |
| 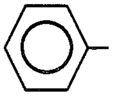 | 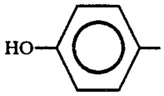 | 274–276 | 3250 ($\nu_{OH}$), 1740 |
| 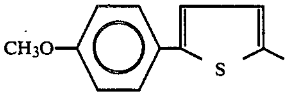 | 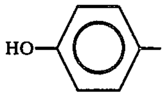 | >250 | 1750 |
| 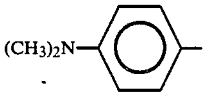 | 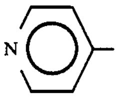 | >260 | 1710 |

TABLE 14-continued
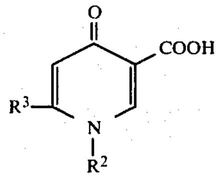
| $R^3$ | $R^2$ | m.p. (°C.) | IR (KBr) $cm^{-1}$: $\nu_{C=O}$ |
|---|---|---|---|
| 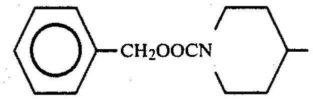 | 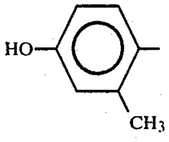 | 123-129 | 1730, 1710, 1690 |
| 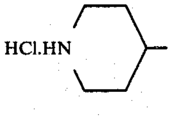 | 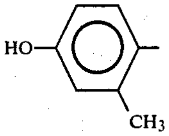 | 242-250 | 1720 |
| 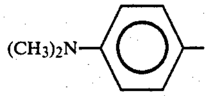 | 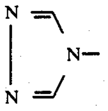 | >280 | 1690 |
| 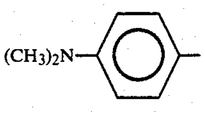 | 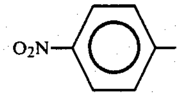 | >280 | 1725, 1710 |
| 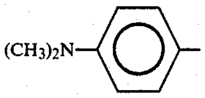 | 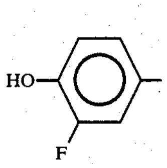 | >280 | 1730, 1700 |
| 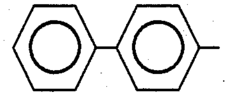 | 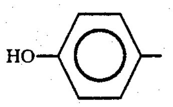 | >280 | 1730, 1700 |
| 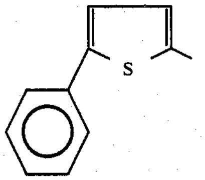 | 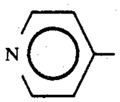 | >250 | 1720, 1700 |
| 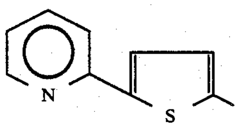 | 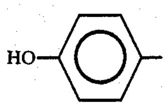 | >250 | 1705 |
| 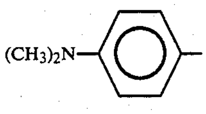 | 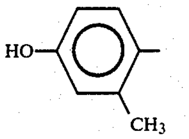 | >280 | 1725, 1700 |

TABLE 14-continued

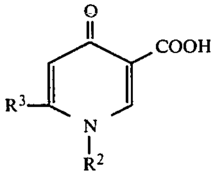

| $R^3$ | $R^2$ | m.p. (°C.) | IR (KBr) $cm^{-1}$: $\nu_{C=O}$ |
|---|---|---|---|
| 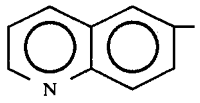 | 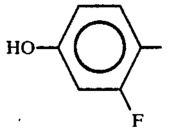 | 196–198 | 1715, 1700 |
| 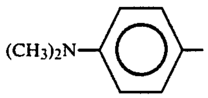 | 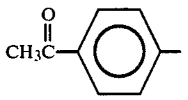 | 253–255 | 1720, 1680 |

(2) Methyl 1-[4-(3-ethyloxycarbonyl-4-hydroxy)-phenyl]-6-{4-(thiophen-2-yl)phenyl}-4-oxo-1,4-dihydronicotinate was hydrolyzed in the same manner as in Example 1-(4) to obtain the compound shown in Table 15.

TABLE 15

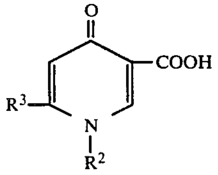

| $R^3$ | $R^2$ | m.p. (°C.) | IR(KBr) $cm^{-1}$: $\nu_{C=O}$ |
|---|---|---|---|
| 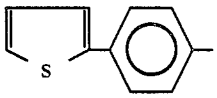 | 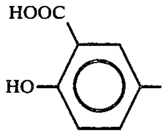 | >280 | 1725, 1710 |

EXAMPLE 6

In 10 ml of chloroform was dissolved 1 g of 1-(4-fluorophenyl)-6-(4-dimethylaminophenyl)-4-oxo-1,4-dihydronicotinic acid, and to the resulting solution were then added 0.32 g of triethylamine and 0.76 g of pivaloyloxyethyl iodide at room temperature, after which the resulting mixture was subjected to reaction at the same temperature for 2 hours. After completion of the reaction, the reaction mixture was washed successively with 20 ml of a 0.1N aqueous sodium hydroxide solution and 20 ml of water and dried with anhydrous magnesium sulfate. Then, the solvent was removed by distillation under reduced pressure, and to the residue was added 20 ml of a diethyl ether/n-hexane (1:1 by volume) mixed solvent, after which insolubles were removed by filtration to obtain 0.6 g of 1-pivaloyloxyethyl 1-(4-fluorophenyl)-6-(4-dimethylaminophenyl)-4-oxo-1,4-dihydronicotinate having a melting point of 117°-120° C.

IR (KBr) $cm^{-1}$: $\nu_{C=O}$ 1745, 1720.

The compounds shown in Table 16 were obtained in the same manner.

TABLE 16

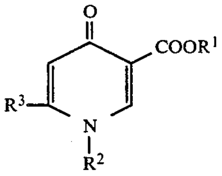

| $R^3$ | $R^2$ | $R^1$ | m.p. (°C.) | IR(KBr) $cm^{-1}$: $\nu_{C=O}$ |
|---|---|---|---|---|
| 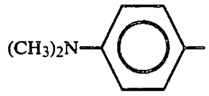 | 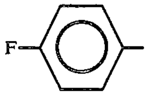 | 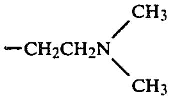 | 186–188 | 1725, 1700 |

TABLE 16-continued

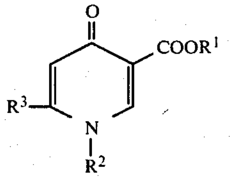

| $R^3$ | $R^2$ | $R^1$ | m.p. (°C.) | IR(KBr) $cm^{-1}$: $\nu_{C=O}$ |
|---|---|---|---|---|
| 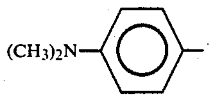 | 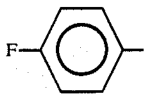 | 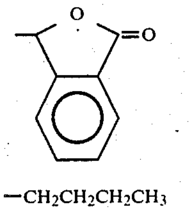 | 220-223 | 1785, 1730, 1700 |
| 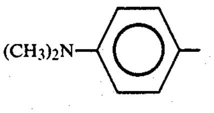 | 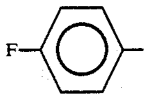 | $-CH_2CH_2CH_2CH_3$ | 170-174 | 1730, 1695 |
| 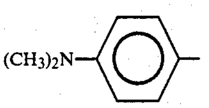 | 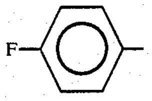 | $-CH_2CH_2CH_3$ | 181-183 | 1720, 1700 |
| 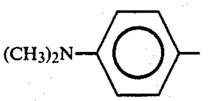 | 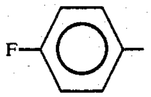 | $-CH_2CH_3$ | 222-225 | 1725, 1695 |

EXAMPLE 7

In a mixed solvent of 2.5 ml of anisole and 2.5 ml of trifluoroacetic acid was dissolved 0.25 g of methyl 6-(4-diphenylmethyloxycarbonylphenyl)-1-(4-fluorophenyl)-4-oxo-1,4-dihydronicotinate, and they were reacted at room temperature for 1.5 hours. After completion of the reaction, the solvent was removed by distillation under reduced pressure, and the residue was dissolved in a mixed solvent of 2.5 ml of ethanol and 2.5 ml of a 1N aqueous sodium hydroxide solution, and the resulting solution was subjected to reaction at room temperature for 3 hours. After completion of the reaction, 20 ml of water and 20 ml of benzene were added to the reaction mixture and the aqueous layer was separated. The aqueous solution thus obtained was adjusted to a pH of 5.5 with acetic acid and the precipitated crystals were collected by filtration, to obtain 0.10 g of 6-(4-carboxyphenyl)-1-(4-fluorophenyl)-4-oxo-1,4-dihydronicotinic acid having a melting point of 280° C. or more.

IR (KBr) $cm^{-1}$: $\nu_{C=O}$ 1720, 1710

NMR ($d_6$-DMSO) δ value: 6.97 (1H, s, $C_5$—H), 7.34 (2H, d, J=8 Hz,

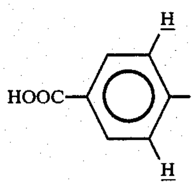

), 7.16-7.79 (4H, m,

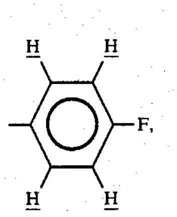

, 7.94 (2H, d, J=8 Hz,

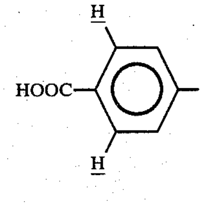

), 8.73 (1H, s, $C_2$—H)

EXAMPLE 8

In a mixed solvent of 3 ml of methanol and 3 ml of 10% by weight aqueous sodium hydroxide solution was dissolved 0.5 g of 6-(4-acetaminophenyl)-1-(4-fluorophenyl)-4-oxo-1,4-dihydronicotinic acid, and the resulting solution was subjected to reaction at 60° C. for 4 hours. After completion of the reaction, the reaction mixture was cooled to room temperature and adjusted to a pH of 6.0 with acetic acid. The precipitated crystals were collected by filtration, washed with water and dried to obtain 0.36 g of 6-(4-aminophenyl)-1-(4-fluorophenyl)-4-oxo-1,4-dihydronicotinic acid having a melting point of 262°-266° C.

IR (KBr) $cm^{-1}$: $\nu_{C=O}$ 1715.

A corresponding acetamino form was hydrolyzed in the same manner, to obtain the compound shown in Table 17.

TABLE 17

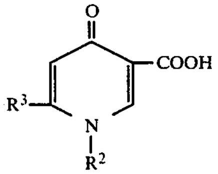

| $R^3$ | $R^2$ | m.p. (°C.) | IR(KBr) $cm^{-1}$: $\nu_{C=O}$ |
|---|---|---|---|
| 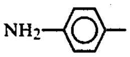 | 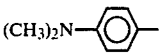 | 265 (decomp.) | 1710 |

EXAMPLE 9

In 7 ml of 47% by weight hydrobromic acid was suspended 0.2 g of 1-(4-fluorophenyl)-6-(4-methoxyphenyl)-4-oxo-1,4-dihydronicotinic acid was suspended, and the suspension was refluxed for 2 hours. After completion of the reaction, the reaction mixture was cooled to room temperature, diluted with 10 ml of water, adjusted to a pH of 12 with a 20% by weight aqueous sodium hydroxide solution, and washed with 20 ml of chloroform. This aqueous solution was then adjusted to a pH of 6.0 with acetic acid and the precipitated crystals were collected by filtration, and washed with water to obtain 0.15 g of 1-(4-fluorophenyl)-6-(4-hydroxyphenyl)-4-oxo-1,4-dihydronicotinic acid having a melting point of 185°-193° C.

IR (KBr) $cm^{-1}$: $\nu_{C=O}$ 1705.

The compounds shown in Table 18 were obtained in the same manner.

TABLE 18

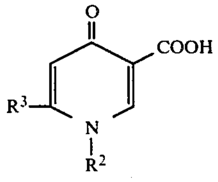

| $R^3$ | $R^2$ | m.p. (°C.) | IR(KBr) $cm^{-1}$: $\nu_{C=O}$ |
|---|---|---|---|
| 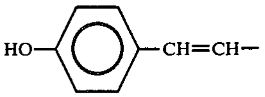 | 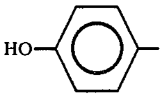 | >200 | 1730, 1705 |
| 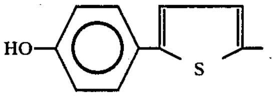 | 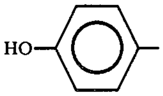 | >250 | 1700 |
| 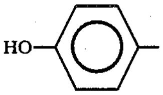 | 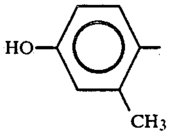 | >250 | 1720, 1705 |
| 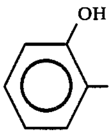 | 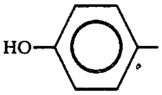 | 270-271 | 1720 |
| 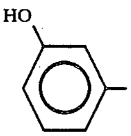 | 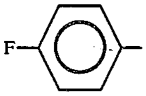 | >250 | 1720, 1700 |
| 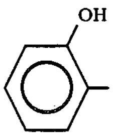 | 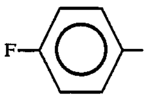 | 144-145 | 1720 |

TABLE 18-continued

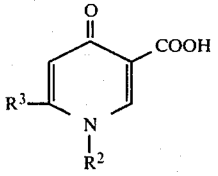

| $R^3$ | $R^2$ | m.p. (°C.) | IR(KBr) $cm^{-1}$: $\nu_{C=O}$ |
|---|---|---|---|
| 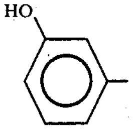 | 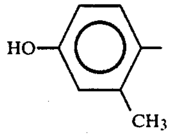 | 157-160 | 1715 |
| 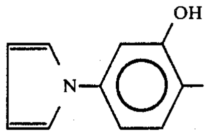 | 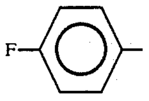 | 173-175 | 1730 |
| 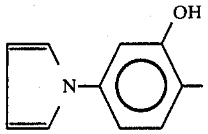 | 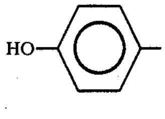 | >250 | 1710, 1700 |

EXAMPLE 10

In 10 ml of ethanol were suspended 0.3 g of 6-(4-aminophenyl)-1-(4-fluorophenyl)-4-oxo-1,4-dihydronicotinic acid and 0.15 g of 5-nitrofurfural, and the suspension was subjected to reaction at 80° C. for 2 hours. After completion of the reaction, the reaction mixture was cooled to room temperature and the insolubles were removed by filtration. The solvent was removed by distillation under reduced pressure. Then, 10 ml of diethyl ether was added to the residue, and the insolubles were collected by filtration to obtain 0.13 g of 1-(4-fluorophenyl)-6-[4-{(5-nitrofurfurylidene)amino}-phenyl]-4-oxo-1,4-dihydronicotinic acid having a melting point of 129°-131° C.

IR (KBr) $cm^{-1}$: $\nu_{C=O}$ 1720, $\nu_{NO_2}$ 1350

EXAMPLE 11

In 50 ml of methanol was suspended 6.5 g of 6-(4-aminophenyl)-1-(4-fluorophenyl)-4-oxo-1,4-dihydronicotinic acid, and the suspension was cooled to 5° C., after which 3.9 g of thionyl chloride was added dropwise thereto over 10 minutes. After completion of the dropwise addition, the resulting mixture was refluxed for 6 hours, and then cooled to room temperature, after which the solvent was removed by distillation under reduced pressure. To the residue were added 30 ml of water and 30 ml of chloroform, and the resulting mixture was adjusted to a pH of 7 with sodium hydrogencarbonate, after which the aqueous layer was separated, washed with 30 ml of a saturated aqueous solution of sodium chloride, and then dried with anhydrous magnesium sulfate. The solvent was removed by distillation under reduced pressure. The resulting crystalline substance was washed with 50 ml of diethyl ether to obtain 6.7 g of methyl 6-(4-aminophenyl)-1-(4-fluorophenyl)-4-oxo-1,4-dihydronicotinate having a melting point of 250° C. or more.

IR (KBr) $cm^{-1}$: $\nu_{C=O}$ 1720.

NMR (d-TFA) δ values: 3.75 (3H, s, $-COOC\underline{H}_3$), 4.15 (2H, bs, $-N\underline{H}_2$), 6.20-7.61 (9H, m,

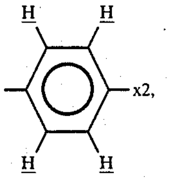

$C_5$—H), 8.35 (1H, s, $C_2$—H)

EXAMPLE 12

In a mixed solvent of 5 ml of acetic acid and 4 ml of water was dissolved 0.7 g of methyl 6-(4-aminophenyl)-1-(4-fluorophenyl)-4-oxo-1,4-dihydronicotinate, and to this solution was added dropwise a solution of 0.3 g of sodium cyanate in 3 ml of water at room temperature over 5 minutes, after which the mixture was subjected to reaction at the same temperature for 2 hours. After completion of the reaction, 10 ml of water was added to the reaction mixture and the precipitated crystals were collected by filtration. These crystals were suspended in a mixed solution of 5 ml of methanol and 5 ml of a 1N aqueous sodium hydroxide solution, and the suspension was stirred at room temperature for 30 minutes. The homogenized solution was adjusted to a pH of 6.0 with acetic acid and the precipitated crystals were collected by filtration, washed with water and dried to obtain 0.5 g of 1-(4-fluorophenyl-4-oxo-6-(4-ureidophenyl)-1,4-dihydronicotinic acid having a melting point of 185°-190° C. (decomp.).

IR (KBr) $cm^{-1}$: $\nu_{C=O}$ 1720.

EXAMPLE 13

In 5 ml of N,N-dimethylformamide was dissolved 0.35 g of methyl 6-(4-aminophenyl)-1-(4-fluorophenyl)-4-oxo-1,4-dihydronicotinate, and 1 g of 2-bromoethanol and 0.3 g of triethylamine were added to the solution, after which the resulting mixture was refluxed for 2 hours. After completion of the reaction, the reaction mixture was cooled to room temperature, and 10 ml of water was then added thereto, after which the resulting mixture was extracted with 10 ml of chloroform. The extract was washed with 10 ml of a saturated aqueous solution of sodium chloride and dried with anhydrous magnesium sulfate. Then, the solvent was removed by distillation under reduced pressure and the residue was purified by a column chormatography (Wako Silica Gel C-200; eluent: chloroform) to obtain an oily substance. This oily substance was dissolved in a mixture of 2 ml of methanol and 3 ml of a 1N aqueous sodium hydroxide solution, and they were reacted at room temperature for 30 minutes. After completion of the reaction, the reaction mixture was adjusted to a pH of 6.0 with acetic acid, and the precipitated crystals were collected by filtration, washed with water and dried to obtain 0.15 g of 1-(4-fluorophenyl)-6-[4-N-(2-hydroxyethyl)aminophenyl]-4-oxo-1,4-dihydronicotinic acid having a melting point of 226°-228° C.

IR (KBr) $cm^{-1}$: $\nu_{C=O}$ 1720

EXAMPLE 14

In 5 ml of N,N-dimethylformamide was dissolved 0.5 g of methyl 6-(4-aminophenyl)-1-(4-fluorophenyl)-4-oxo-1,4-dihydronicotinate, and 0.23 g of allyl chloride and 0.3 g of triethylamine were added thereto, and the resulting mixture was refluxed for 3 hours. After completion of the reaction, the reaction mixture was cooled, and 10 ml of water was added thereto, after which the resulting mixture was extracted with 10 ml of chloroform. The extract was washed with 10 ml of a saturated aqueous solution of sodium chloride and dried with anhydrous magnesium sulfate. The solvent was then removed by distillation under reduced pressure, and the residue was purified by a column chromatograpy (Wako Silica Gel C-200; eluant: chloroform) to obtain an oily substance. This oily substance was dissolved in a mixture of 2 ml of methanol and 3 ml of a 1N aqueous sodium hydroxide solution, and they were reacted at room temperature for 30 minutes. After completion of the reaction, the reaction mixture was adjusted to a pH of 6.0 with acetic acid, and the precipitated crystals were collected by filtration, washed with water, and dried to obtain 0.32 g of 6-(4-N-allylaminophenyl)-1-(4-fluorophenyl)-4-oxo-1,4-dihydronicotinic acid having a melting point of 183°-185° C.

IR (KBr) $cm^{-1}$: $\nu_{C=O}$ 1720.

EXAMPLE 15

In 10 ml of 47% by weight hydrobromic acid was suspended 0.3 g of 1-(2-fluoro-4-methoxyphenyl)-6-(4-dimethylaminophenyl)-4-oxo-1,4-dihydronicotinic acid, and the suspension was refluxed for 2 hours. After completion of the reaction, the reaction mixture was cooled to room temperature and diluted with 10 ml of water. The resulting solution was then adjusted to a pH of 12 with 20% by weight aqueous sodium hydroxide solution and washed with 20 ml of chloroform. The aqueous layer was adjusted to a pH of 6.0 with acetic acid, and the precipitated crystals were collected by filtration, washed with 10 ml of water, and dried to obtain 0.17 g of 1-(2-fluoro-4-hydroxyphenyl)-6-(4-dimethylaminophenyl)-4-oxo-1,4-dihydronicotinic acid having a melting point of 250° C. or more.

IR (KBr) $cm^{-1}$: $\nu_{C=O}$ 1720.

NMR ($d_6$-DMSO) $\delta$ values: 2.97 (6H, s, $-N(C\underline{H}_3)_2$), 6.52-7.35 (8H, m,

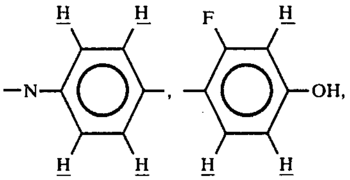

$C_5$—H), 8.60 (1H, s, $C_2$—H), 10.45 (1H, bs,

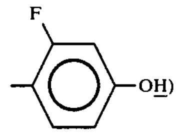

The compounds shown in Table 19 were obtained in the same manner.

TABLE 19

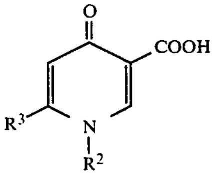

| $R^3$ | $R^2$ | m.p. (°C.) | IR (KBr) $cm^{-1}$: $\nu_{C=O}$ |
|---|---|---|---|
| 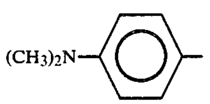 | 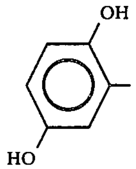 | 251-254 | 1720, 1700 |
| 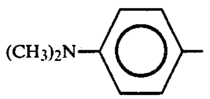 | 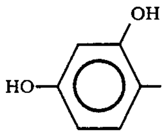 | >280 | 1710 |
| 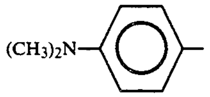 | 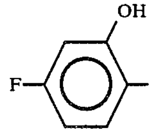 | >280 | 1720 |
| 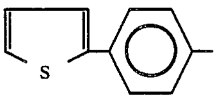 | 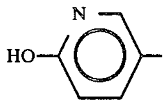 | >250 | 1720 |

EXAMPLE 16

In a mixed solvent of 10 ml of ethanol and 10 ml of a 10% by weight aqueous sodium hydroxide solution was dissolved 0.5 g of methyl 1-(4-acetaminophenyl)-6-(2-naphthyl)-4-oxo-1,4-dihydronicotinate, and the solution was refluxed for 3 hours. After completion of the reaction, the reaction mixture was cooled to room temperature, and diluted with 20 ml of water. This solution was then adjusted to a pH of 5.5 with acetic acid, and the precipitated crystals were collected by filtration, washed with water, and dried to obtain 0.38 g of 1-(4-aminophenyl)-6-(2-naphthyl)-4-oxo-1,4-dihydronicotinic acid having a melting point of 148°-151° C.

IR (KBr) $cm^{-1}$: $\nu_{NH}$ 3470, 3360; $\nu_{C=O}$ 1715, 1700.

The compounds shown in Table 20 were obtained in the same manner.

TABLE 20

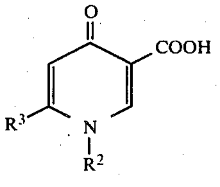

| $R^3$ | $R^2$ | m.p. (°C.) | IR (KBr) $cm^{-1}$: $\nu_{C=O}$ |
|---|---|---|---|
| 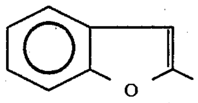 | 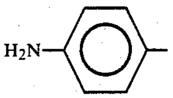 | >250 | 1720, 1700 |
| 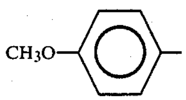 | 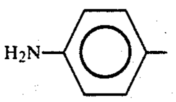 | 237-239 | 1720, 1700 |

TABLE 20-continued

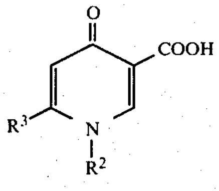

| $R^3$ | $R^2$ | m.p. (°C.) | IR (KBr) $cm^{-1}$: $\nu_{C=O}$ |
|---|---|---|---|
| 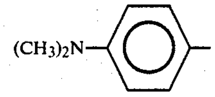 | 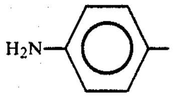 | 147-151 | 1710, 1700 |

EXAMPLE 17

With 1 g of 6-(4-dimethylaminophenyl)-1-(4-hydroxyphenyl)-4-oxo-1,4-dihydronicotinic acid was mixed 10 ml of acetic anhydride and the resulting mixture was subjected to reaction at 130° C. for 2 hours. After completion of the reaction, the reaction mixture was cooled to room temperature and introduced into 150 ml of water. After stirring the mixture for 1 hour, 150 ml of ethyl acetate was added to the mixture, and the organic layer was separated, washed with 100 ml of water and then with 50 ml of a saturated aqueous solution of sodium chloride, and dried with anhydrous magnesium sulfate. The solvent was removed by distillation under reduced pressure, and to the residue was added 20 ml of diethyl ether, and the resulting mixture was filtered to obtain 0.75 g of 1-(4-acetyloxyphenyl)-6-(4-dimethylaminophenyl)-4-oxo-1,4-dihydronicotinic acid having a melting point of 128°-131° C.

IR (KBr) $cm^{-1}$: $\nu_{C=O}$ 1760, 1720, 1700.

The compounds shown in Table 21 were obtained in the same manner.

TABLE 21

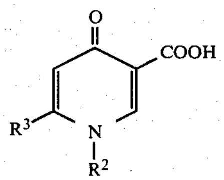

| $R^3$ | $R^2$ | m.p. (°C.) | IR (KBr) $cm^{-1}$: $\nu_{C=O}$ |
|---|---|---|---|
| 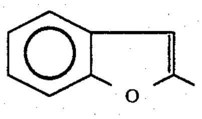 | 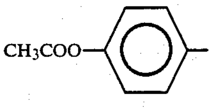 | 231-234 | 1760, 1720 |
| 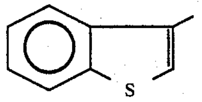 | 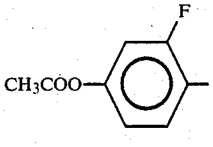 | 178-179 | 1765, 1730 |
| 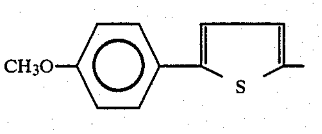 | 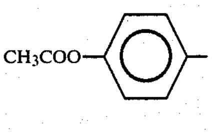 | 235-237 | 1760, 1700 |

TABLE 21-continued

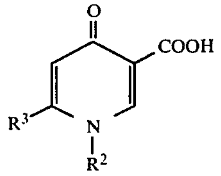

| $R^3$ | $R^2$ | m.p. (°C.) | IR (KBr) $cm^{-1}$: $\nu_{C=O}$ |
|---|---|---|---|
| 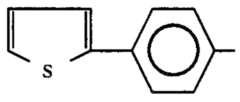 | 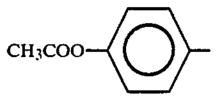 | 205-207 | 1760, 1740, 1720 |
| 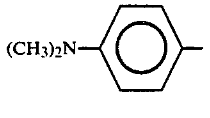 | 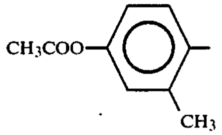 | 194-195 | 1760, 1715 |
| 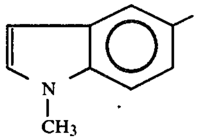 | 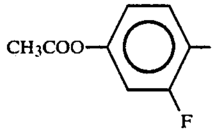 | 230.5-233 | 1770, 1730 |
| 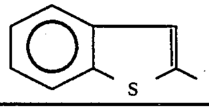 | 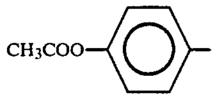 | 229-231 | 1760, 1720 |

EXAMPLE 18

(1) In the same manner as in Example 4, methyl 1-(4-fluorophenyl)-6-methyl-4-oxo-1,4-dihydronicotinate (m.p. 190°-195° C.) was prepared from methyl 3-oxo-4-hexenoate and 4-flouoroaniline, and 0.7 g of this ester was mixed with 0.32 g of nicotinaldehyde and 0.58 g of acetic anhydride, and they were refluxed for 5 hours. After completion of the reaction, the reaction mixture was cooled to room temperature, and 20 ml of water was added thereto, after which the mixture was successively extracted with three 40-ml portions of chloroform. The chloroform layer was washed with 50 ml of a saturated aqueous solution of sodium chloride and dried with anhydrous magnesium sulfate, and the solvent was removed by distillation under reduced pressure. The residue was purified by a column chromatography (Wako Silica Gel C-200; eluent: chloroform) to obtain 0.496 g of methyl 1-(4-fluorophenyl)-6-[2-(pyridin-3-yl)ethenyl]-4-oxo-1,4-dihydronicotinate having a melting point of 201°-204° C.

IR (KBr) $cm^{-1}$: $\nu_{C=O}$ 1725, 1700

(2) In a mixture of 9 ml of ethanol and 9 ml of a 10% by weight aqueous sodium hydroxide solution was suspended 0.45 g of methyl 1-(4-fluorophenyl)-6-[2-(pyridin-3-yl)ethenyl]-4-oxo-1,4-dihydronicotinate and the suspension was subjected to reaction at room temperature for 30 minutes. After completion of the reaction, the reaction mixture was adjusted to a pH of 6.0 with acetic acid, and the precipitated crystals were collected by filtration and dried to obtain 0.357 g of 1-(4-fluorophenyl)-6-[2-(pyridin-3-yl)ethenyl]-4-oxo-1,4-dihydronicotinic acid having a melting point of 250° C. or more.

IR (KBr) $cm^{-1}$: $\nu_{C=O}$ 1710.

NMR ($d_6$-DMSO) δ values: 6.64 (1H, d, J=16 Hz,

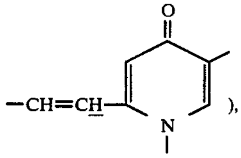

), 7.10-8.00 (8H, m,

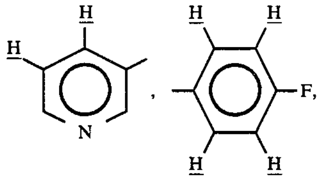

$C_5$—H,

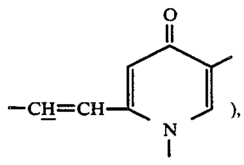

), 8.50-8.85 (3H, m,

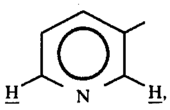

$C_2$—H)

EXAMPLE 19

To 0.7 g of 1-(4-fluorophenyl)-6-methyl-4-oxo-1,4-dihydronicotinic acid was added 0.33 g of isonicotinaldehyde and 0.61 g of acetic anhydride, and they were refluxed for 5 hours. After completion of the reaction, 30 ml of water was added to the reaction mixture, and the mixture was successively extracted with three 30-ml portions of chloroform. The chloroform layer was separated, washed with 20 ml of a saturated aqueous solution of sodium chloride, and then dried with anhydrous magnesium sulfate. The solvent was removed by distillation under reduced pressure to obtain 0.42 g of 1-(4-fluorophenyl)-6-[2-(pyridin-4-yl)ethenyl]-4-oxo-1,4-dihydronicotinic acid having a melting point of 205°-215° C.

IR (KBr) $cm^{-1}$: $\nu_{C=O}$ 1715, 1690

The compounds shown in Table 22 were obtained in the same manner.

TABLE 22

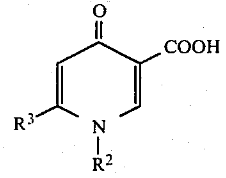

| $R^3$ | $R^2$ | m.p. (°C.) | IR (KBr) $cm^{-1}$: $\nu_{C=O}$ |
|---|---|---|---|
| 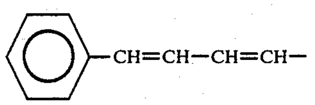 | 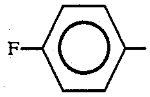 | 213-215 | 1720 |
| 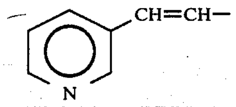 | 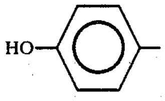 | 218-224 | 1700 |

EXAMPLE 20

In 5 ml of benzene was dissolved 1 g of methyl 3-oxo-5-(pyrrol-2-yl)-4-pentenoate and to this solution was added 0.74 g of N,N-dimethylformamidodimethylacetal. They were reacted at 70° C. for 1.5 hours. To the reaction mixture was then added 0.56 g of 4-hydroxyaniline, and they were further reacted at room temperature for 1 hour. The precipitated crystals were collected by filtration and dissolved in 10 ml of N,N-dimethylformamide. They were reacted at 140° C. for 3 hours. After completion of the reaction, the reaction mixture was cooled to room temperature and the solvent was removed by distillation under reduced pressure. The residue was purified by a column chromatography (Wako Silica Gel C-200; eluent: chloroform) to obtain an oily substance. This oily substance was dissolved in 10 ml of dioxane, and to this solution was added dropwise a solution of 0.54 g of 2,3,5,6-tetrachloro-p-benzoquinone in 5 ml of dioxane at 95° C. Thereafter, the mixture was subjected to reaction at the same temperature for 30 minutes, and the reaction mixture was cooled to room temperature. The precipitated crystals were collected by filtration, dissolved in a mixture of 5 ml of methanol and 10 ml of a 10% by weight aqueous sodium hydroxide solution, and they were reacted at room temperature for 30 minutes. After completion of the reaction, the reaction mixture was adjusted to a pH of 6.0 with acetic acid, and the precipitated crystals were collected by filtration, washed with water, and dried to obtain 0.3 g of 1-(4-hydroxyphenyl)-4-oxo-6-(pyrrol-2-yl)-1,4-dihydronicotinic acid having a melting point of 250° C. or more.

IR (KBr) $cm^{-1}$: $\nu_{C=O}$ 1710.

NMR (d-TFA) δ values: 7.18-7.90 (8H, m,

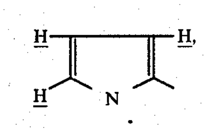, 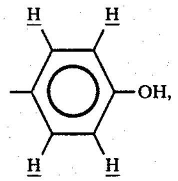, $C_5$—H), 9.0 (1H, s, $C_2$—H)

The compounds shown in Table 23 were obtained in the same manner.

TABLE 23
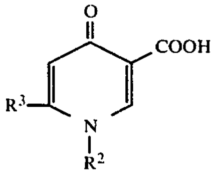
| $R^3$ | $R^2$ | m.p. (°C.) | IR (KBr) $cm^{-1}$: $\nu_{C=O}$ |
|---|---|---|---|
| 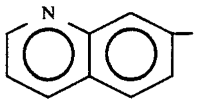 | 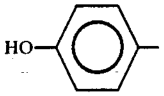 | 202–203.5 | 1720, 1700 |
| 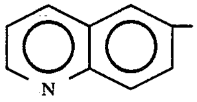 | 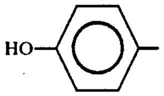 | 194–197 | 1715, 1700 |
| 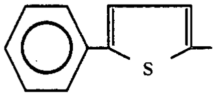 | 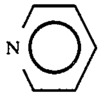 | >250 | 1720 |
| 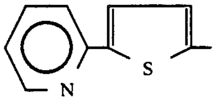 | 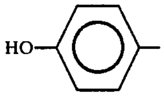 | >250 | 1705 |
| 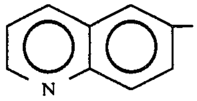 | 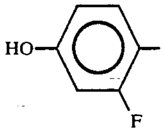 | 196–198 | 1715, 1700 |
| 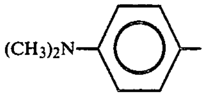 | 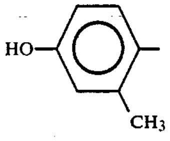 | >280 | 1725, 1700 |
| 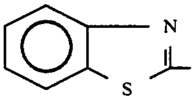 | 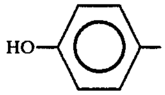 | >250 | 1730 |
| 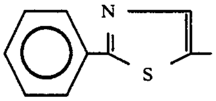 | 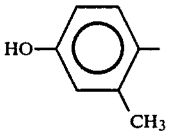 | >250 | 1720 |
| 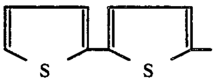 | 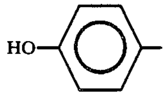 | >250 | 1750 |
| 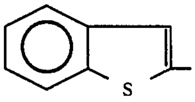 | 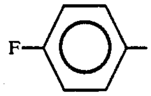 | 218–220 | 1715, 1700 |

TABLE 23-continued
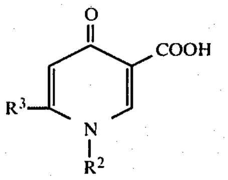
| $R^3$ | $R^2$ | m.p. (°C.) | IR (KBr) $cm^{-1}$: $\nu_{C=O}$ |
|---|---|---|---|
| 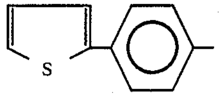 | 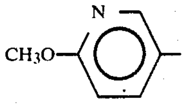 | 212–214 | 1725 |
| 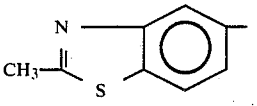 | 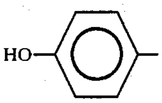 | >250 | 1725, 1710 |
| 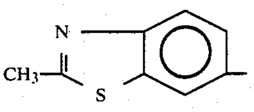 | 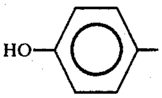 | >250 | 1720, 1700 |
| 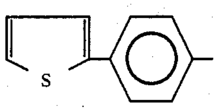 | 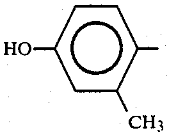 | 173–176 | 1715 |
| 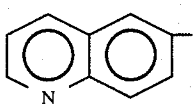 | 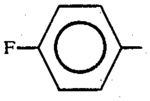 | 125–126 | 1725 |
| 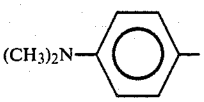 | 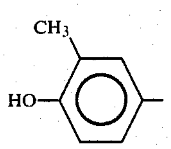 | 267–269 | 1730, 1700 |
| 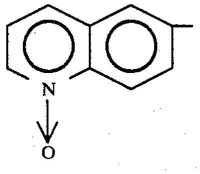 | 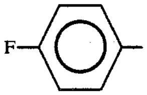 | >250 | 1725, 1700 |
| 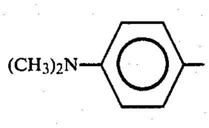 | 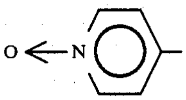 | >250 | 1730 |
| 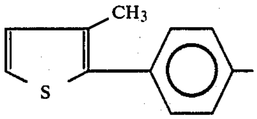 | 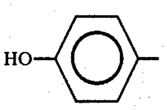 | >250 | 1730 |
| 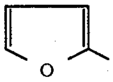 | 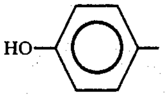 | >280 | 1720, 1705 |

TABLE 23-continued
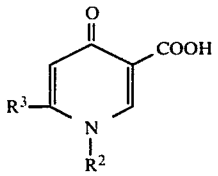
| $R^3$ | $R^2$ | m.p. (°C.) | IR (KBr) $cm^{-1}$: $\nu_{C=O}$ |
|---|---|---|---|
| 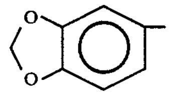 | 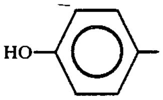 | 160–165 | 1720 |
| 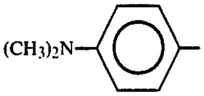 | 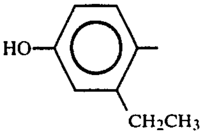 | 277–278 | 1725, 1700 |
| 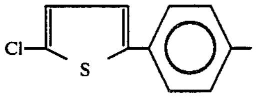 | 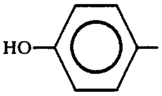 | 178–180 | 1720 |
| 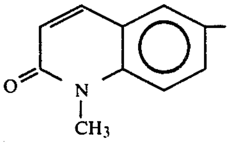 | 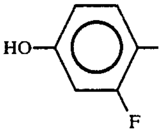 | 208–209 | 1725 |
| 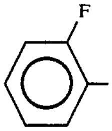 | 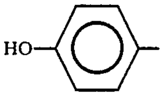 | >250 | 1735 |
| 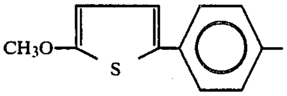 | 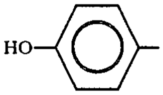 | >250 | 1740 |
| 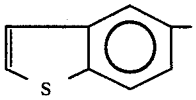 | 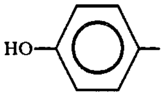 | >250 | 1750 |
| 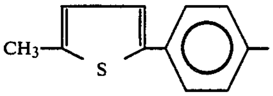 | 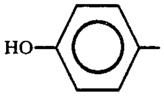 | >280 | 1745, 1715 |
| 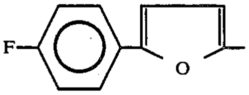 | 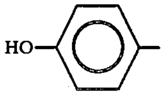 | >280 | 1725, 1715 |
| 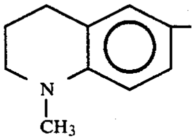 | 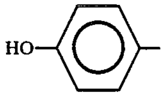 | >250 | 1730 |

TABLE 23-continued
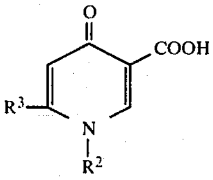
| $R^3$ | $R^2$ | m.p. (°C.) | IR (KBr) cm$^{-1}$: $\nu_{C=O}$ |
|---|---|---|---|
| 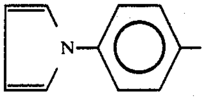 | 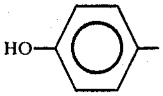 | >250 | 1735 |
| 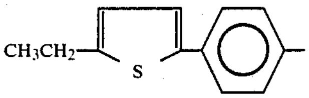 | 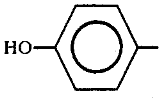 | 268-271 | 1735, 1700 |
| 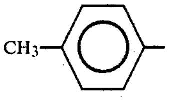 | 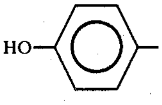 | 282-288 | 1730 |
| 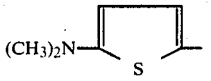 | 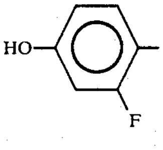 | 250 (decomp.) | 1725 |
| 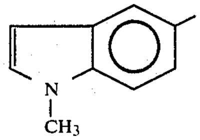 | 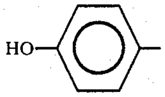 | 279-282 | 1720 |
| 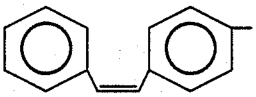 | 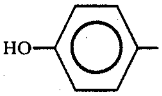 | >280 | 1730, 1710 |
| 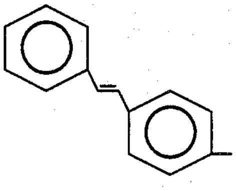 | 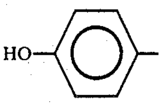 | 285-288 | 1735, 1720 |
| 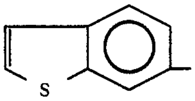 | 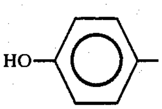 | >250 | 1750 |
| 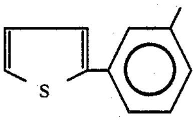 | 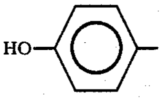 | >250 | 1730 |
| 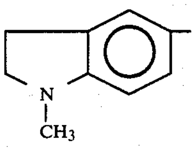 | 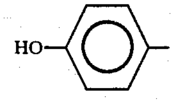 | 253-255.5 | 1730 |

TABLE 23-continued
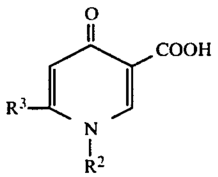
| $R^3$ | $R^2$ | m.p. (°C.) | IR (KBr) cm$^{-1}$: $\nu_{C=O}$ |
|---|---|---|---|
| 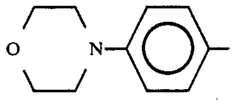 | 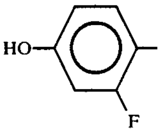 | 295-296 | 1725 |
| 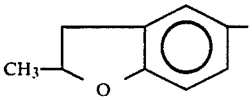 | 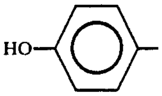 | 261-263 | 1720, 1700 |
| 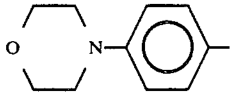 | 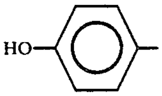 | >250 | 1720 |
| 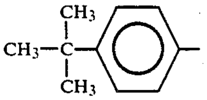 | 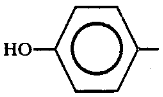 | 220-221 | 1730 |
| 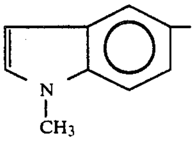 | 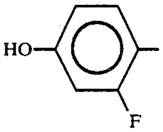 | 278-282 | 1725, 1715 |
| 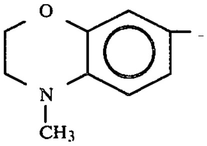 | 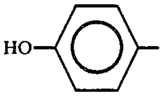 | >250 | 1720 |
| 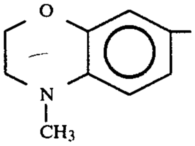 | 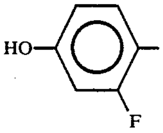 | >250 | 1720 |
| 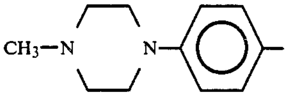 | 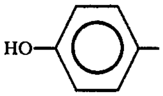 | >250 | 1720 |
| 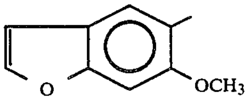 | 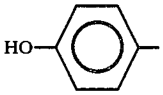 | 245-250 | 1720, 1705 |
| 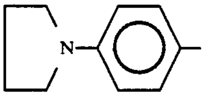 | 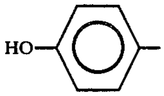 | >250 | 1710, 1690 |

TABLE 23-continued
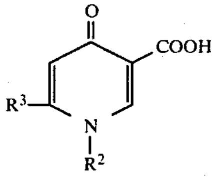
| $R^3$ | $R^2$ | m.p. (°C.) | IR (KBr) $cm^{-1}$: $\nu_{C=O}$ |
|---|---|---|---|
| 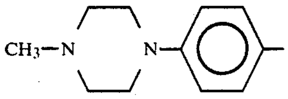 | 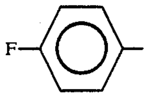 | >250 | 1720 |
| 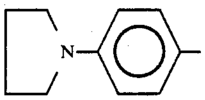 | 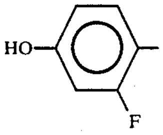 | 185-187 | 1720 |
| 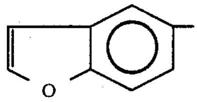 | 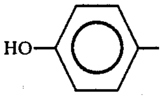 | 281-283 | 1735 |
| 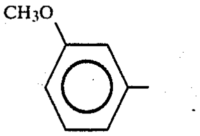 | 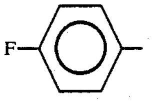 | 220-223 | 1715 |
| 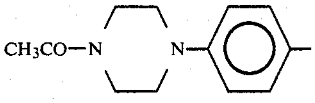 | 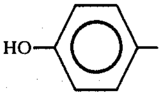 | 195-197 | 1720, 1700, 1660 |
| 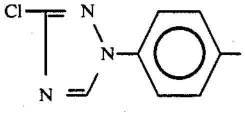 | 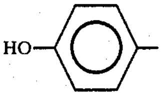 | 182-183 | 1715 |
| 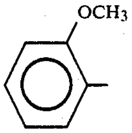 | 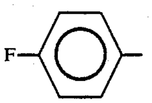 | 181-183 | 1720 |
| 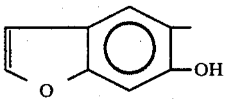 | 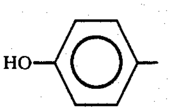 | 207-210 | 1705 |
| 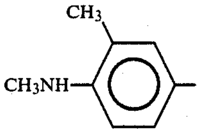 | 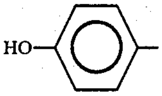 | >250 | 1730 |
| 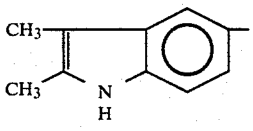 | 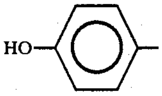 | >270 | 1725 |

TABLE 23-continued
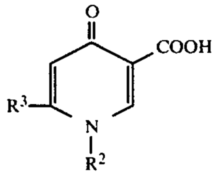
| $R^3$ | $R^2$ | m.p. (°C.) | IR (KBr) $cm^{-1}$: $\nu_{C=O}$ |
|---|---|---|---|
| 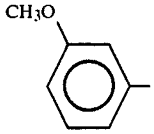 | 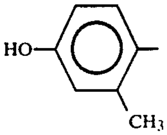 | 122–125 | 1720, 1700 |
| 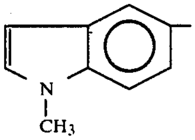 | 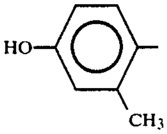 | >250 | 1725, 1710 |
| 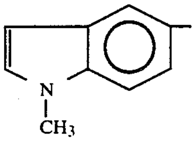 | 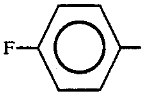 | 215–217 | 1725, 1705 |
| 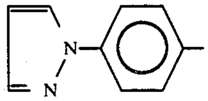 | 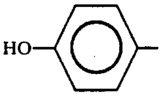 | 172–174 | 1720 |
| 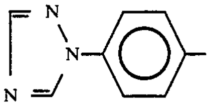 | 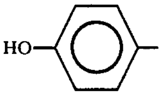 | 257–258 | 1715 |
| 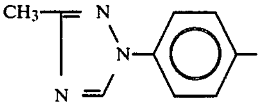 | 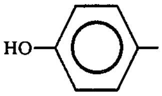 | >280 | 1710 |
| 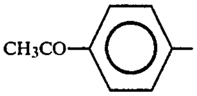 | 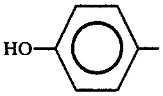 | >280 | 1725, 1665 |
| 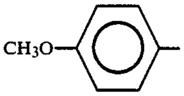 | 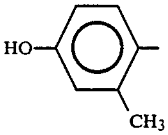 | 239–241 | 1720, 1700 |
| 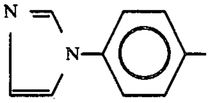 | 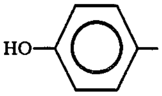 | 220–223 | 1725 |
| 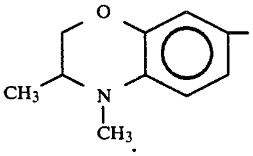 | 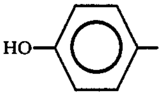 | >250 | 1725 |

TABLE 23-continued
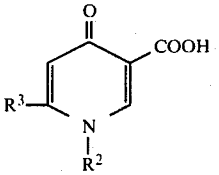
| $R^3$ | $R^2$ | m.p. (°C.) | IR (KBr) $cm^{-1}$: $\nu_{C=O}$ |
|---|---|---|---|
| 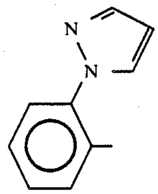 | 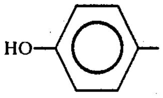 | >250 | 1715, 1705 |
| 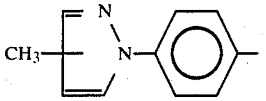 | 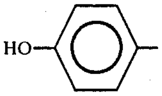 | >250 | 1720, 1710 |
| 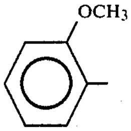 | 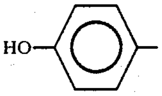 | >290 | 1725, 1710 |
| 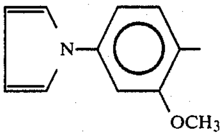 | 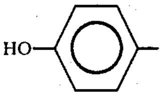 | >250 | 1720, 1700 |
| 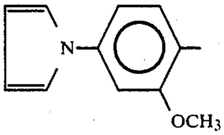 | 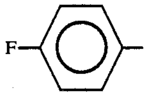 | 130-133 | 1720 |
| 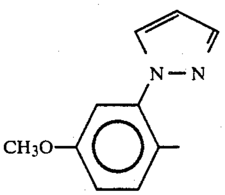 | 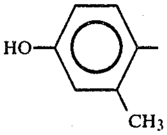 | 168-171 | 1720 |
| 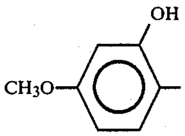 | 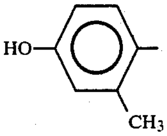 | >250 | 1720, 1700 |
| 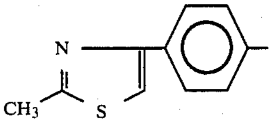 | 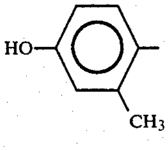 | 247-250 | 1720, 1710 |

TABLE 23-continued
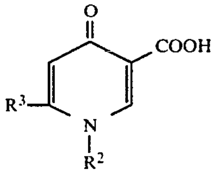
| $R^3$ | $R^2$ | m.p. (°C.) | IR (KBr) $cm^{-1}$: $\nu_{C=O}$ |
|---|---|---|---|
| 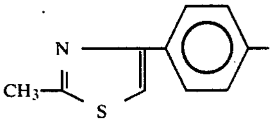 | 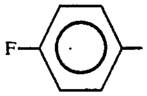 | 252-253 | 1715 |
| 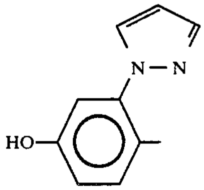 | 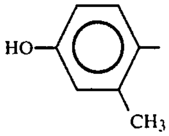 | 193-196 | 1720 |
| 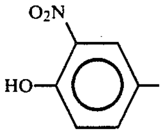 | 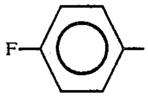 | 242-245 | 1720, 1710 |
| 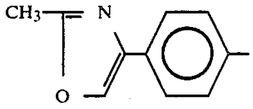 | 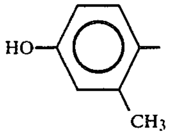 | 226-230 | 1710 |
| 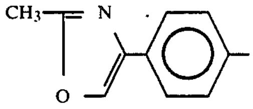 | 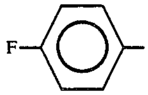 | 208-211 | 1720 |
| 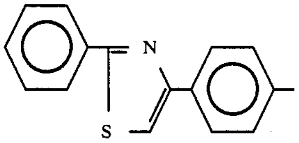 | 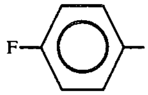 | 227-229 | 1725 |
| 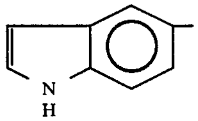 | 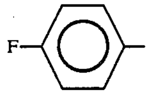 | 166-167 | 1730 |
| 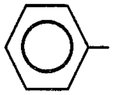 | 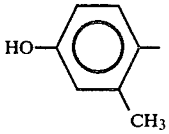 | 144-147 | 1715 |
| 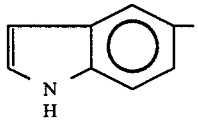 | 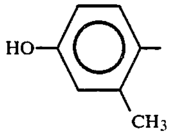 | 205-209 | 1715 |

TABLE 23-continued
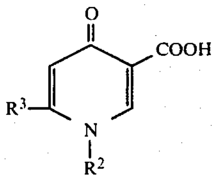
| $R^3$ | $R^2$ | m.p. (°C.) | IR (KBr) $cm^{-1}$: $\nu_{C=O}$ |
|---|---|---|---|
| 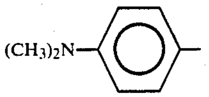 | 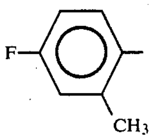 | 249–251 | 1730 |
| 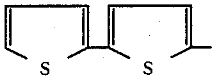 | 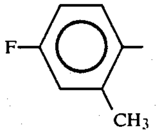 | 178–180 | 1720 |
| 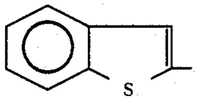 | 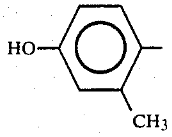 | 234–238 | 1670 |
| 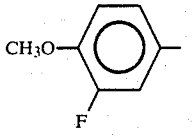 | 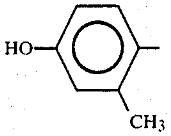 | 231–233 | 1730, 1710 |
| 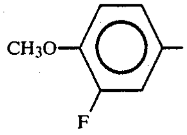 | 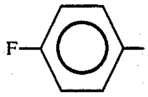 | 220–222 | 1730, 1710 |
| 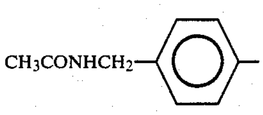 | 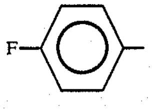 | 247–248 | 1720 |
| 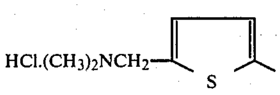 | 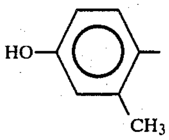 | 140–155 | 1725, 1710, 1685 |
| 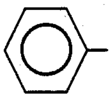 | 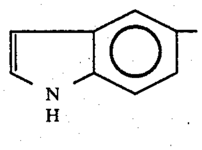 | >250 | 1730 |
| 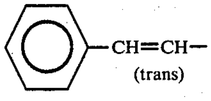 | 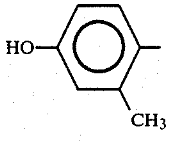 | >250 | 1725, 1715 |

TABLE 23-continued

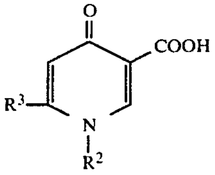

| R³ | R² | m.p. (°C.) | IR (KBr) cm⁻¹: $\nu_{C=O}$ |
|---|---|---|---|
| 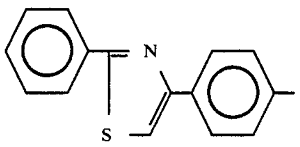 | 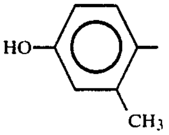 | 281-288 | 1720, 1700, 1680 |

EXAMPLE 21

In 10 ml of 47% by weight hydrobromic acid was suspended 0.15 g of 1-(3,4-methylenedioxyphenyl)-6-(4-dimethylaminophenyl)-4-oxo-1,4-dihydronicotinic acid, and they were refluxed for 2 hours. After completion of the reaction, the reaction mixture was cooled to room temperature, and diluted with 10 ml of water. This solution was adjusted to a pH of 12 with a 20% weight aqueous sodium hydroxide solution, washed with 20 ml of chloroform, and again adjusted to a pH of 6.0 with acetic acid. This solution was extracted with 50 ml of chloroform, and the extract was washed with 30 ml of a saturated aqueous solution of sodium chloride and dried with anhydrous magnesium sulfate. The solvent was removed by distillation under reduced pressure, and the residue was purified by a column chromatography (Wako Silica Gel C-200; eluent: chloroform/methanol (15:1 by volume) mixture) to obtain 0.05 g of 1-(3,4-dihydroxyphenyl)-6-(4-dimethylaminophenyl)-4-oxo-1,4-dihydronicotinic acid having a melting point of 223°-227° C.

IR (KBr) $cm^{-1}$: $\nu C{=}O$ 1720, 1700.

EXAMPLE 22

In 3 ml of methanol and 5 ml of 10% by weight aqueous sodium hydroxide solution was dissolved 0.5 g of methyl 6-(4-acetaminophenyl)-1-(3-pyridyl)-4-oxo-1,4-dihydronicotinate, and they were reacted at 60° C. for 4 hours. After completion of the reaction, the reaction mixture was cooled to room temperature and adjusted to a pH of 6.0 with acetic acid, and the precipitated crystals were collected by filtration, washed with 10 ml of water, and then dried to obtain 0.34 g of 6-(4-aminophenyl)-1-(3-pyridyl)-4-oxo-1,4-dihydronicotinic acid having a melting point of 207°-208° C.

IR (KBr) $cm^{-1}$: $\nu_{C=O}$ 1720, 1700.

The compounds shown in Table 24 were obtained in the same manner.

TABLE 24

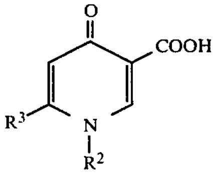

| R³ | R² | m.p. (°C.) | IR (KBr) cm⁻¹: $\nu_{C=O}$ |
|---|---|---|---|
| 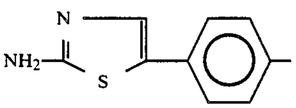 | 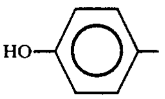 | 243-250 | 1720, 1710 |
| 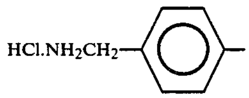 | 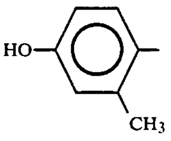 | >280 | 1720, 1700 1680 |
| 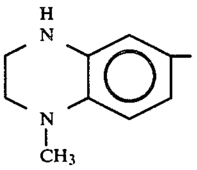 | 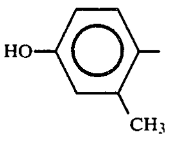 | >250 | 1710 |

EXAMPLE 23

In 18 ml of anhydrous methylene chloride was dissolved 0.36 g of 1-(4-acetoxyphenyl)-6-(2-benzo[b]-thienyl)-4-oxo-1,4-dihydronicotinic acid, and to this solution was added 0.137 ml of triethylamine at room temperature. The reaction mixture thus obtained was cooled to −40° C., and 0.094 ml of ethyl chlorocarbonate was added thereto. The resulting mixture was subjected to reaction at the same temperature for 1 hour. This reaction mixture was then mixed with 0.14 g of 5-indanol. The mixture was subjected to reaction for 1 hour, and elevated to room temperature. After completion of the reaction, the reaction mixture was washed successively with 15 ml of water and a saturated aqueous solution of sodium chloride, and then dried with anhydrous magnesium sulfate. The solvent was removed by distillation under reduced pressure, and the residue was purified by a column chromatography (Wako Silica Gel C-200; eluent: chloroform) to obtain 0.25 g of indanyl 1-(4-acetoxyphenyl)-6-(2-benzo[b]-thienyl)-4-oxo-1,4-dihydronicotinate having a melting point of 234°-236° C.

IR (KBr) $cm^{-1}$: $\nu_{C=O}$ 1760 (Sh), 1745, 1710.

The compounds shown in Table 25 were obtained in the same manner.

TABLE 25

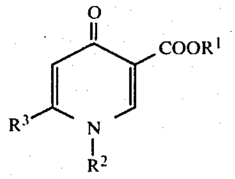

| $R^3$ | $R^2$ | $R^1$ | m.p. (°C.) | IR (KBr) $cm^{-1}$: $\nu_{C=O}$ |
|---|---|---|---|---|
| 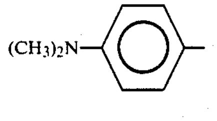 | 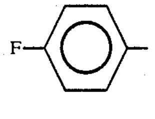 | 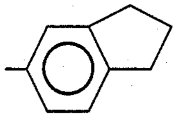 | 234-235 | 1745, 1710 |
| 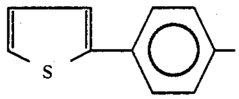 | 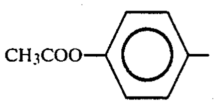 | 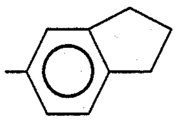 | 209-211 | 1760, 1745 |
| 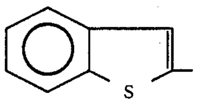 | 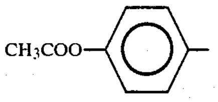 | $-CH_2CH_3$ | 232-234 | 1760, 1725, 1705 |
| 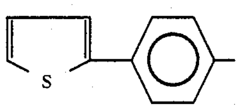 | 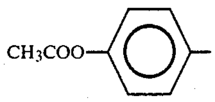 | $-CH_2CH_3$ | 188-190 | 1765, 1730, 1690 |
| 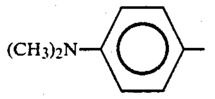 | 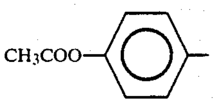 | $-CH_2CH_2N(CH_3)_2$ | 186-190 | 1760, 1730, 1695 |
| 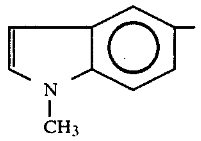 | 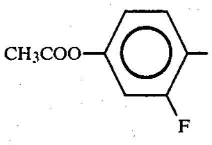 | $-CH_2CH_2N(CH_3)_2$ | 120-123 | 1765, 1730 |

EXAMPLE 24

(1) In 15 ml of N,N-dimethylformamide was dissolved 0.4 g of 6-(4-dimethylaminophenyl)-1-(4-hydroxyphenyl)-4-oxo-1,4-dihydronicotinic acid at room temperature, and to this solution was added 0.33 g of potassium carbonate. The resulting mixture was heated to 100° C. for 1 hour. The reaction mixture thus obtained was cooled to room temperature, and 0.2 g of methoxymethyl chloride was added thereto. The resulting mixture was subjected to reaction at room temperature for 1 hour. After completion of this reaction, the solvent was removed by distillation under reduced pressure, and the residue was purified by a column chromatography (Wako Silica Gel C-200; eluent: chloroform/ethanol (30:1 by volume) mixture) to obtain 0.16 g of methoxymethyl 6-(4-dimethylaminophenyl)-1-(4-methoxymethyloxyphenyl)-4-oxo-1,4-dihydronicotinate having a melting point of 199°-201° C. and 0.13 g of methoxymethyl 6-(4-dimethylaminophenyl)-1-(4- hydroxyphenyl)-4-oxo-1,4-dihydronicotinate having a melting point of 211°-213° C.

Methoxymethyl 6-(4-dimethylaminophenyl)-1-(4-methoxymethyloxyphenyl)-4-oxo-1,4-dihydronicotinate:

IR (KBr) $cm^{-1}$: $\nu_{C=O}$ 1725, 1695.

Methoxymethyl 6-(4-dimethylaminophenyl)-1-(4-hydroxyphenyl)-4-oxo-1,4-dihydronicotinate:

IR (KBr) $cm^{-1}$: $\nu_{C=O}$ 1735, 1700.

(2) In 1 ml of ethanol was dissolved 0.08 g of methoxymethyl 6-(4-dimethylaminophenyl)-1-(4-methoxymethyloxyphenyl)-4-oxo-1,4-dihydronicotinate at room temperature, and 1 ml of a 10% by weight aqueous sodium carbonate solution was added to the resulting solution. The resulting mixture was subjected to reaction at the same temperature for 1 hour. After completion of the reaction, the reaction mixture was adjusted to a pH of 6.0 with acetic acid, and the precipitated crystals were collected by filtration, washed with 5 ml of water, and dried to obtain 0.06 g of 6-(4-dimethylaminophenyl)-1-(4-methoxymethyloxyphenyl)-4-oxo-1,4-dihydronicotinic acid having a melting point of 150°-152° C.

IR (KBr) $cm^{-1}$: $\nu_{C=O}$ 1720.

EXAMPLE 25

In 12 ml of N,N-dimethylformamide was dissolved 0.6 g of methyl 1-(3-nitro-4-fluorophenyl)-6-(4-dimethylaminophenyl)-4-oxo-1,4-dihydronicotinate and to this solution was added 0.2 g of 5% by weight palladium carbon, and the above ester was hydrogenated under atmospheric pressure for 2 hours. Then, the catalyst was removed by filtration and the solvent was removed by distillation under reduced pressure. The resulting residue was dissolved in a mixture consisting of 2 ml of ethanol and 2 ml of a 1N aqueous sodium hydroxide solution, and the solution was subjected to reaction at room temperature for one hour. This reaction mixture was mixed with 10 ml of water and 10 ml of chloroform, and the mixture was adjusted to a pH of 5.5 with acetic acid. The organic layer was separated, washed successively with 10 ml of water and 10 ml of a saturated aqueous solution of sodium chloride, and dried with anhydrous magnesium sulfate. Then the solvent was removed by distillation under reduced pressure, and the residue was purified by a column chromatography (Wako Silica Gel C-200; eluent: chloroform/ethanol (100:1 by volume) mixture) to obtain 0.1 g of 1-(3-amino-4-fluorophenyl)-6-(4-dimethylaminophenyl)-4-oxo-1,4-dihydronicotinic acid having a melting point of 198°-201° C.

IR (KBr) $cm^{-1}$: $\nu_{C=O}$ 1720.

EXAMPLE 26

To 0.2 g of 5% by weight palladium carbon was added 5 ml of methanol, and the resulting mixture was stirred under atmospheric pressure in a hydrogen atmosphere for 10 minutes. To this mixture was added a solution prepared by dissolving 0.3 of methyl 6-[4-(p-nitrobenzyl)-2H-3,4-dihydrobenzo-1,4-oxazin-7-yl]-1-(4-fluorophenyl)-4-oxo-1,4-dihydronicotinate in 3 ml of methanol. The resulting mixture was subjected to hydrogenation at room temperature under 3 atm. for 2 hours. After completion of the reaction, the catalyst was removed by filtration and the solvent was removed by distillation under reduced pressure. The residue was purified by a column chromatography (Wako Silica Gel C-200; eluent: chloroform/ethanol (25:1 by volume) mixture) and the fraction containing the objective substance was concentrated to obtain 0.17 g of methyl 6-(2H-3,4-dihydrobenzo-1,4-oxazin-7-yl)-1-(4-fluorophenyl)-4-oxo-1,4-dihydronicotinate having a melting point of 194°-197° C.

IR (KBr) $cm^{-1}$: $\nu_{C=O}$ 1725, 1695.

EXAMPLE 27

In 10 ml of methanol was dissolved 0.5 g of 6-(4-hydroxy-3-nitrophenyl)-4-oxo-1-(4-fluorophenyl)-1,4-dihydronicotinic acid, and to this solution was added 0.1 g of 5% by weight palladium carbon. The said acid was hydrogenated under atmospheric pressure for 2 hours. After completion of the reaction, the reaction mixture was filtered and the filtrate was concentrated under reduced pressure to obtain 0.45 g of 6-(4-hydroxy-3-aminophenyl)-4-oxo-1-(4-fluorophenyl)-1,4-dihydronicotinic acid having a melting point of 231°-233° C.

IR (KBr) $cm^{-1}$: $\nu_{C=O}$ 1730.

EXAMPLE 28

In 7 ml of benzene was dissolved 0.6 g of methyl 5-(4-benzoyl-2H-3,4-dihydrobenzo-1,4-oxazin-6-yl)-3-oxo-4-pentenoate, and 0.2 g of N,N-dimethylformamidodimethylacetal was added to the solution. They were reacted at 60°-70° C. for 2 hours. The reaction mixture was cooled to room temperature, and 0.19 g of p-fluoroaniline was added thereto. The resulting mixture was subjected to reaction at room temperature for 4 hours. After completion of this reaction, the solvent was removed by distillation under reduced pressure, and the residue was purified by a column chromatography (Wako Silica Gel C-200; eluent: toluene/ethyl acetate (20:1 by volume) mixture). The fraction containing the objective substance was concentrated and the crystals thus formed were dissolved in 5 ml of N,N-dimethylformamide, and they were refluxed for 5 hours. After completion of the reaction, the solvent was removed by distillation under reduced pressure, and the residue was purified by a column chromatography (Wako Silica Gel C-200; eluent: chloroform). The fraction containing the objective substance was concentrated, and the oily substance thus formed was dissolved in 5 ml of toluene, and 0.11 g of 2,3,5,6-tetrachloro-p-benzoquinone was added to the resulting solution. The solution was subjected to reaction at 80°-90° C. for 30 minutes. After completion of the reaction, the solvent was removed by distillation under reduced pressure, and the residue was dissolved in 2 ml of chloroform. The insolubles were removed by filtration, and the filtrate was purified by a column chromatography (Wako Silica Gel C-200; eluent: chloroform). The fraction containing the objective substance was concentrated, and to crystals thus formed were added 5 ml of ethanol and 5 ml of a 1N aqueous sodium hydroxide solution, and they were reacted at room temperature for 2 hours. After completion of this reaction, ethanol was removed by distillation under reduced pressure, and the residue was adjusted to a pH of 6.5 with acetic acid. The precipitated crystals were collected by filtration, washed with water, and dried to obtain 0.4 g of 6-(2H-3,4-dihydrobenzo-1,4-oxazin-6-yl)-1-(4-fluorophenyl)-4-oxo-1,4-dihydronicotinic acid having a melting point of 155°-167° C.

IR (KBr) $cm^{-1}$: $\nu_{C=O}$ 1720.

The following compound was obtained in the same manner:

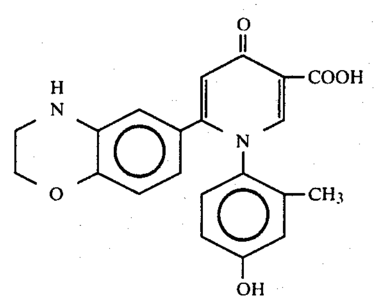

Melting point (°C.): 205-207
IR (KBr) $cm^{-1}$: $\nu_{C=O}$ 1725.

EXAMPLE 29

In 5 ml of benzene was dissolved 0.3 g of methyl 5-phenyl-3-oxo-4-pentenoate, and 0.2 g of N,N-dimethylformamidodimethylacetal was added to the solution. They were reacted at 60°-70° C. for 2 hours. The reaction mixture was cooled to room temperature, and 0.3 g of 4-(4-acetylpiperazino)-aniline was added thereto. The mixture was subjected to reaction at room temperature for 4 hours. After completion of the reaction, the solvent was removed by distillation under reduced pressure, and the oily substance thus obtained was dissolved in 5 ml of N,N-dimethylformamide, and they were refluxed for 5 hours. After completion of the reaction, the solvent was removed by distillation under reduced pressure, and the residue was purified by a column chromatography (Wako Silica Gel C-200; eluent: chloroform/ethanol (25:1 by volume) mixture). The fraction containing the objective substance was concentrated, and the oily substance thus obtained was dissolved in 4 ml of dioxane, and 0.12 g of 2,3,5,6-tetrachloro-p-benzoquinone was added thereto. They were reacted at 90°-100° C. for 30 minutes. After completion of the reaction, the solvent was removed by distillation under reduced pressure, and the residue was purified by a column chromatography (Wako Silica Gel C-200; eluent: chloroform/ethanol (100:3 by volume) mixture). The fraction containing the objective substance was concentrated, and to the crystals thus formed were added 3 ml of 6N hydrochloric acid, and the resulting mixture was refluxed for 2 hours. Water was removed by distillation under reduced pressure, to obtain 0.12 g of 6-phenyl-1-(4-piperazinophenyl)-4-oxo-1,4-dihydronicotinic acid dihydrochloride having a melting point of 211°-213° C. (decomp.)

IR (KBr) $cm^{-1}$: $\nu_{C=O}$ 1720, 1695.

EXAMPLE 30

5 ml of methanol was carefully added to 0.05 g of 5% by weight palladium carbon under ice cooling, and this mixture was stirred under a hydrogen atmosphere for 20 minutes, followed by addition of a solution of 0.4 g of methyl 6-(1-benzyloxycarbonyl-3-piperidinyl)-1-(4-hydroxy-2-methylphenyl)-4-oxo-1,4-dihydronicotinate in 2 ml of methanol, and the mixture was subjected to hydrogenation under atmospheric pressure for 4 hours. After completion of the reaction, the palladium carbon was removed by filtration, and the solvent was removed by distillation under reduced pressure. The residue was dissolved in 5 ml of methanol, and 1.4 ml of 1N aqueous sodium hydroxide was added thereto, and they were reacted at room temperature for 10 minutes. Thereafter, the solvent was removed by distillation under reduced pressure, to obtain 0.15 g of disodium 6-(3-piperidinyl)-1-(4-hydroxy-2-methylphenyl)-4-oxo-1,4-dihydronicotinate having a melting point of 250° C. or more.

IR (KBr) $cm^{-1}$: $\nu_{C=O}$ 1630.

NMR ($d_6$-DMSO-$D_2O$) δ values: 0.88-3.17 (12H, m,

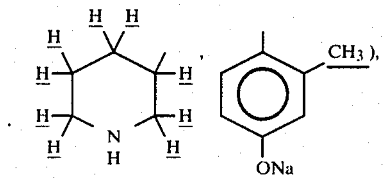

6.50-7.21 (4H, m,

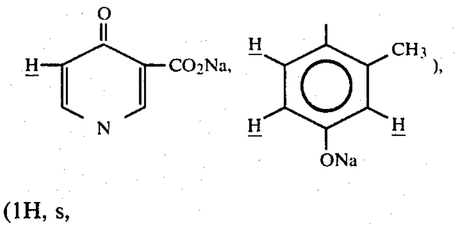

8.07 (1H, s,

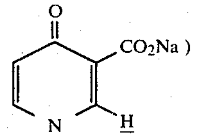

EXAMPLE 31

(1) 5 ml of methanol was carefully added to 0.06 g of 5% by weight palladium carbon under ice cooling, and this mixture was stirred under a hydrogen atomosphere at room temperature for 20 minutes, followed by addition of a solution of 0.4 g of methyl 6-(1-benzyloxycarbonyl-4-piperidinyl)-1-(4-hydroxy-2-methylphenyl)-4-oxo-1,4-dihydronicotinate in 2 ml of methanol, and the mixture was subjected to hydrogenation under atmospheric pressure for 4 hours. After completion of the reaction, the palladium carbon was removed by filtration and the solvent was removed by distillation under reduced pressure to obtain 0.24 g of methyl 6-(4-piperidinyl)-1-(4-hydroxy-2-methylphenyl)-4-oxo-1,4-dihydronicotinate having a melting point of 226°-228° C.

IR (KBr) $cm^{-1}$: $\nu_{C=O}$ 1730.

(2) In 4 ml of N,N-dimethylformamide was dissolved 0.24 g of methyl 6-(4-piperidinyl)-1-(4-hydroxy-2-methylphenyl)-4-oxo-1,4-dihydronicotinate, and 0.17 g of isopropyl bromide and 0.06 g of potassium carbonate were added to the solution, after which they were reacted at 60° C. for 6 hours. After completion of the reaction, the solvent was removed by distillation under reduced pressure, and the residue was dissolved in a mixture of 20 ml of chloroform and 20 ml of water. The organic layer was separated, washed twice with 20-ml portions of water, and dried with anhydrous sodium sulfate. Then, the solvent was removed by distillation under reduced pressure, and the oily substance thus obtained was purified by a column chromatography (Wako Silica Gel C-200; eluent: chloroform/ethanol (20:1 by volume) mixture). The fraction containing the objective substance was concentrated, and to the oily substance thus obtained was added 5 ml of 6N hydrochloric acid, and they were refluxed for 2 hours. The solvent was removed by distillation under reduced pressure to obtain 0.11 g of 1-(4-hydroxy-2-methylphenyl)-6-(1-isopropyl-4-piperidinyl)-4-oxo-1,4-dihydronicotinic acid hydrochloride having a melting point of 195.5°-200.5° C.

IR (KBr) $cm^{-1}$: $\nu_{C=O}$ 1720.

EXAMPLE 32

(1) In 20 ml benzene was dissolved 2.0 g of methyl 5-(cyclohexen-4-yl)-3-oxo-4-pentenoate, and 1.4 g of N,N-dimethylformamidodimethylacetal was added thereto. They were reacted at 70° C. for 1.5 hours. This reaction mixture was cooled to room temperature, and 1.2 g of p-hydroxyaniline was added thereto. They were reacted for 1.5 hours. After completion of the reaction, 50 ml of diisopropyl ether was added to the reaction mixture and the precipitated crystals were collected by filtration and washed with 20 ml of diisopropyl ether to obtain 2.1 g of methyl 5-(cyclohexen-4-yl)-2-(4-hydroxyphenylaminomethylene)-3-oxo-4-pentenoate having a melting point of 151°-153° C.

IR (KBr) $cm^{-1}$: $\nu_{C=O}$ 1710.

The compounds shown in Table 26 were obtained in the same manner.

TABLE 26

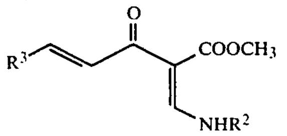

| $R^3$ | $R^2$ | m.p. (°C.) | IR (KBr) $cm^{-1}$: $\nu_{C=O}$ |
|---|---|---|---|
| 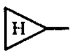 | 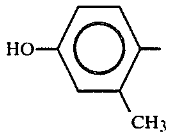 | 173-175 | 1705, 1655 |
| 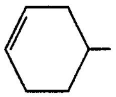 | 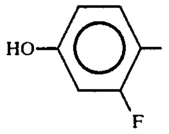 | 142-147 | 1700, 1660 |
| 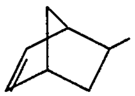 | 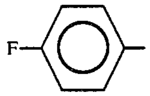 | — | 1700 (neat) |
| 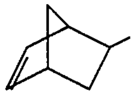 | 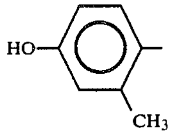 | 167-169 | 1700, 1680, 1660 |
| 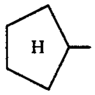 | 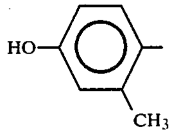 | 167-168 | 1720, 1700 |
| 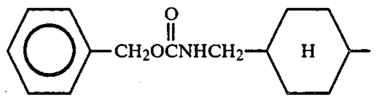 | 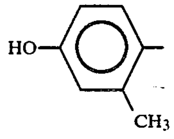 | 141-145 | 1725, 1695 |
| 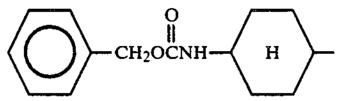 | 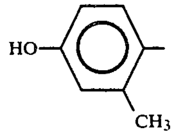 | 120-130 | 1725, 1710 |

(2) In 20 ml of N,N-dimethylformamide was dissolved 2.0 g of methyl 5-(cyclohexen-4-yl)-2-(4-hydroxyphenylaminomethylene)-3-oxo-4-pentenoate, and they were reacted at 140° C. for 4 hours. After completion of the reaction, the solvent was removed by distillation under reduced pressure, and to the residue was added 50 ml of dioxane, after which the precipitated crystals were collected by filtration and washed with 30 ml of diethyl ether to obtain 1.4 g of methyl 6-(cyclohexen-4-yl)-1-(4-hydroxyphenyl)-4-oxo-1,4,5,6-tetrahydronicotinate having a melting point of 155°-157° C.

IR (KBr) $cm^{-1}$: $\nu_{C=O}$ 1715.

The compounds shown in Table 27 were obtained in the same manner.

TABLE 27

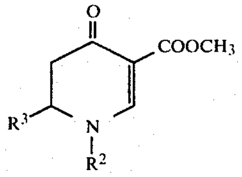

| $R^3$ | $R^2$ | m.p. (°C.) | IR (KBr) $cm^{-1}$: $\nu_{C=O}$ |
|---|---|---|---|
| 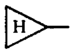 | 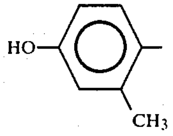 | 217-219 | 1720, 1690 |
| 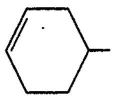 | 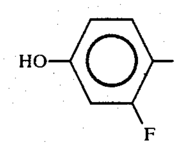 | 154-157 | 1720, 1705 |
| 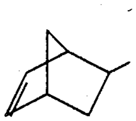 | 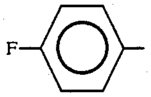 | — | 1720 (neat) |
| 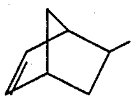 | 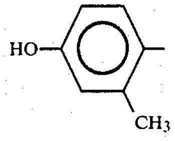 | 201-205 | 1720, 1710 |
| 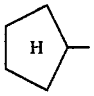 | 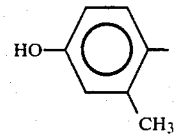 | 197-201 | 1725, 1710, 1670 |
| 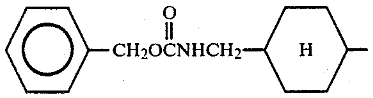 | 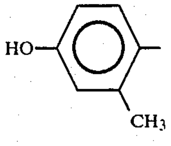 | 105-110 | 1725, 1710 |
| 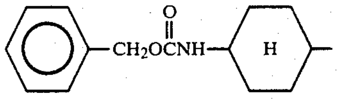 | 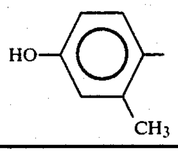 | 110-120 | 1720 |

(3) In 20 ml of dioxane was dissolved 1.0 g of methyl 6-(cyclohexen-4-yl)-1-(4-hydroxyphenyl)-4-oxo-1,4,5,6-tetrahydronicotinate, and the resulting solution was heated to 80° C. To this solution was added dropwise a solution of 0.83 g of 2,3,5,6-tetrachloro-p-benzoquinone in 20 ml of dioxane at 80° C., followed by reaction at the same temperature for 1 hour. After completion of this reaction, the reaction mixture was cooled to room temperature, and the precipitated crystals were collected by filtration and washed with 50 ml of dioxane to obtain 0.7 g of methyl 6-(cyclohexene-4-yl)-1-(4-hydroxyphenyl)-4-oxo-1,4-dihydronicotinate having a melting point of 250° C. or more.
IR (KBr) $cm^{-1}$: $\nu_{C=O}$ 1735, 1705.
NMR ($d_6$-DMSO) δ values:
1.5-2.65(7H, m, 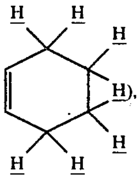 ), 3.75(3H, s, $-COOCH_3$),
5.65(2H, bs, 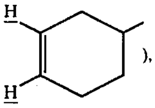 ), 6.34(1H, s, 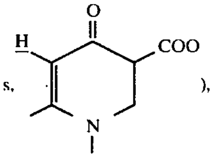 ),
-continued
6.97(2H, d, J=9Hz, 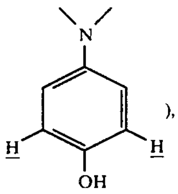 ), 7.45(2H, d, J =9Hz, 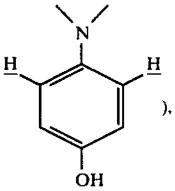 ), 8.12(1H, s, 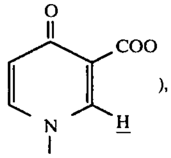 ), 10.12(1H, s, 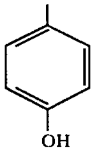 )
The compounds shown in Table 28 were obtained in the same manner.
TABLE 28
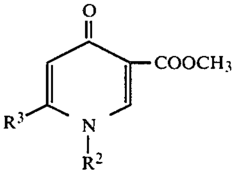
| $R^3$ | $R^2$ | m.p. (°C.) | IR (KBr) $cm^{-1}$: $\nu_{C=O}$ |
|---|---|---|---|
| 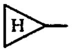 | 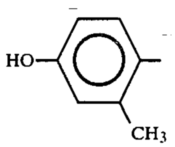 | >250 | 1730 |
| 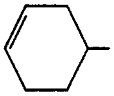 | 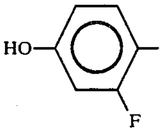 | >250 | 1735, 1705 |
| 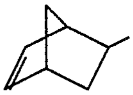 | 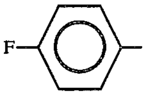 | 247-249 | 1725 |
| 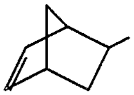 | 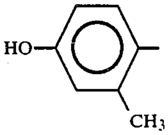 | 240-243 | 1730, 1700 |

TABLE 28-continued

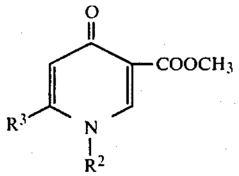

| $R^3$ | $R^2$ | m.p. (°C.) | IR (KBr) $cm^{-1}$: $\nu_{C=O}$ |
|---|---|---|---|
| 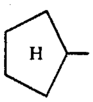 | 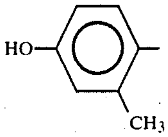 | 254-257 | 1725, 1695 |
| 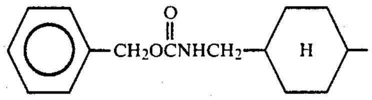 | 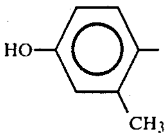 | 130-135 | 1725, 1710 |
| 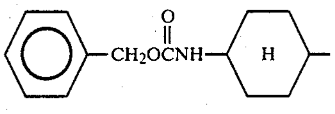 | 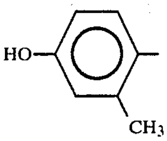 | 150-158 | 1720, 1700 |

(4) In a mixture consisting of 5 ml of methanol and 5 ml of a 1N aqueous sodium hydroxide solution was dissolved 0.5 g of methyl 6-(cyclohexen-4-yl)-1-(4-hydroxyphenyl)-4-oxo-1,4-dihydronicotinate, and they wre reacted at room temperature for 30 minutes. After completion of the reaction, the reaction mixture was adjusted to a pH of 5.5 with acetic acid, and the precipitated crystals were collected by filtration, washed with 30 ml of water, and dried to obtain 0.35 g of 6-(cyclohexen-4-yl)-1-(4-hydroxyphenyl)-4-oxo-1,4-dihydronicotinic acid having a melting point of 250° C. or more.

IR (KBr) $cm^{-1}$: $\nu_{C=O}$ 1725, 1700.

NMR ($D_6$-DMSO) δ values:

1.5-2.5(7H, m, 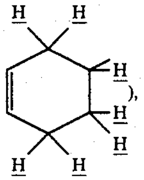 ), 5.50(2H, s, 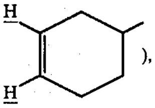 ),

-continued 6.77(1H, s, 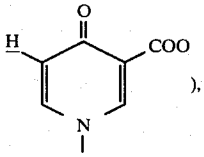 ), 6.88(2H, d, J=9Hz, 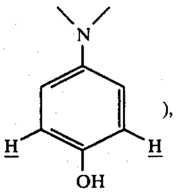 ), 7.40(2H, d, J=9Hz, 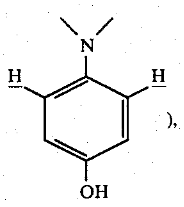 ), 8.28(1H, s, 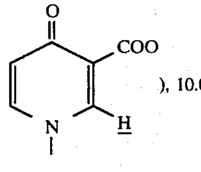 ), 10.05(1H, bs, 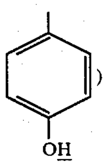 )

The compounds shown in Table 29 were obtained in the same manner.

TABLE 29

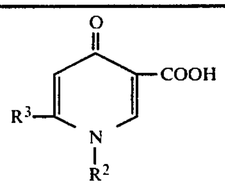

| $R^3$ | $R^2$ | m.p. (°C.) | IR (KBr) $cm^{-1}$: $\nu_{C=O}$ |
|---|---|---|---|
| 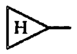 | 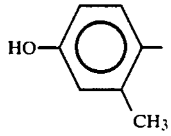 | >250 | 1725, 1710 |
| 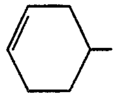 | 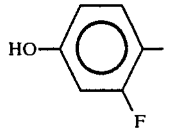 | 242-243 | 1742 |
| 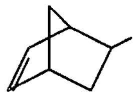 | 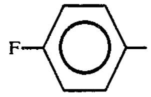 | 195-197 | 1715 |
| 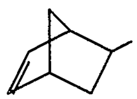 | 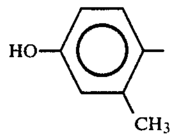 | 150-165 | 1720 |
| 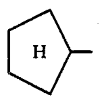 | 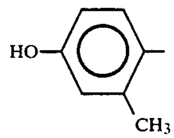 | 259-261 | 1725, 1710 |
| 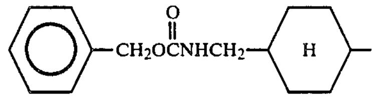 | 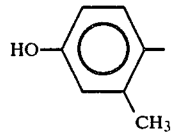 | 271-273 | 1730, 1685 |
| 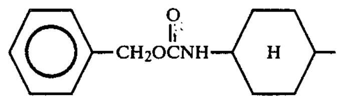 | 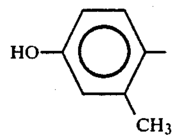 | 190-200 | 1720, 1705, 1690 |

EXAMPLE 33

In 30 ml of N,N-dimethylformamide was dissolved 2.0 g of methyl 5-(cyclohexen-4-yl)-3-oxo-4-pentenoate and 1.4 g of N,N-dimethylformamidodimethylacetal was added thereto. They were reacted at 70° C. for 1.5 hours. To the reaction mixture was then added 1.3 g of 4-hydroxy-2-methylaniline at 70° C., and the resulting mixture was subjected to reaction at 80° C. for 2 hours and at 140° C. for 3 hours. After completion of this reaction, the reaction mixture was cooled to room temperature, and the solvent was removed by distillation under reduced pressure. The residue was dissolved in 20 ml of dioxane, and a solution of 2.4 g of 2,3,5,6-tetrachloro-p-benzoquinone in 15 ml of dioxane was added dropwise thereto at 80° C., followed by reaction at the same temperature for one hour. After completion of the reaction, the solvent was removed by distillation under reduced pressure, and the residue was suspended in 30 ml of chloroform and 30 ml of water. After adjusting the pH of the suspension to 7.5 with sodium hydrogencarbonate, the organic layer was separated, washed successively with 10 ml of water and 20 ml of a saturated aqueous solution of sodium chloride, and then dried with anhydrous magnesium sulfate. The solvent was removed by distillation under reduced pressure to obtain 1.3 g of methyl 6-(cyclohexen-4-yl)-1-(4- hydroxy-2-methylphenyl)-4-oxo-1,4-dihydronicotinate having a melting point of 250° C. or more.
IR (KBr) $cm^{-1}$: $\nu_{C=O}$ 1735, 1705.
NMR ($d_6$-DMSO) δ values:
1.5-2.5 (10H, m, 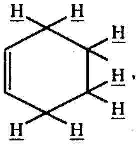, 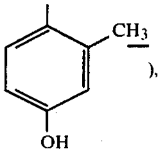),
3.82 (3H, s, $-COOC\underline{H}_3$), 5.67 (2H, s, 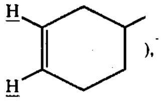),
6.46 (1H, s, 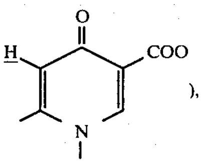),
6.88 (1H, d, J=9Hz, 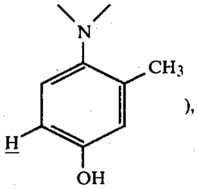),
-continued
6.97 (1H, s, 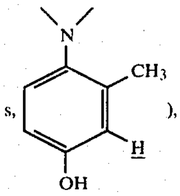),
7.47 (1H, d, J=9Hz, 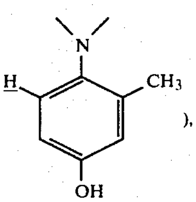),
8.14 (1H, s, 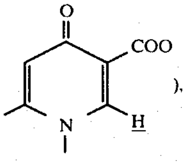), 10.0 (1H, s, 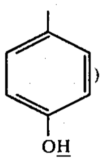)
TABLE 30
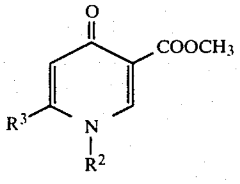
| $R^3$ | $R^2$ | m.p. (°C.) | IR (KBr) $cm^{-1}$: $\nu_{C=O}$ |
|---|---|---|---|
| 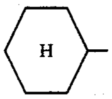 | 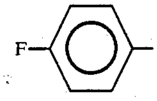 | 252-254 | 1730 |
| 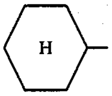 | 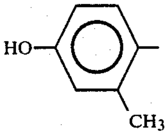 | >250 | 1725, 1705 |
| 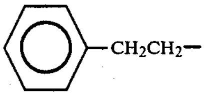 | 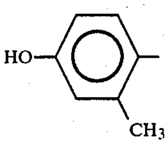 | >250 | 1725, 1700 |
| 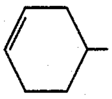 | 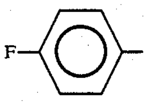 | >250 | 1725 |

TABLE 30-continued

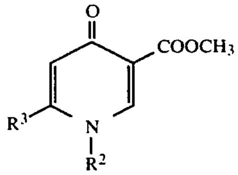

| $R^3$ | $R^2$ | m.p. (°C.) | IR (KBr) $cm^{-1}$: $\nu_{C=O}$ |
|---|---|---|---|
| 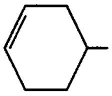 | 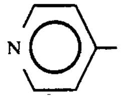 | >250 | 1730 |
| 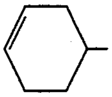 | 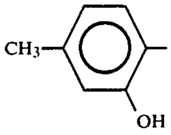 | >250 | 1735, 1705 |
| $CH_3CH{=}CH-$ (trans) | 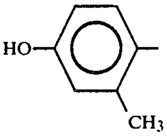 | 162–164 | 1740 |
| 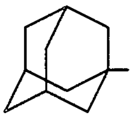 | 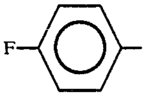 | 286–288 | 1740 |
| 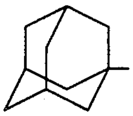 | 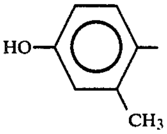 | 293–294 | 1730–1710 |
| 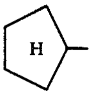 | 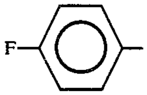 | 204–205 | 1730 |
| $ClCH_2CH_2-$ | 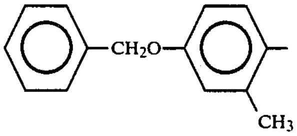 | 118–120 | 1730 |

EXAMPLE 34

In 80 ml of chloroform was dissolved 2.0 g of methyl 6-(cyclohexen-4-yl)-1-(4-hydroxy-2-methylphenyl)-4-oxo-1,4-dihydronicotinate and the solution was cooled to 5° C. To this solution was added dropwise a solution of 1.0 g of bromine in 5 ml of chloroform at 5° C. over 30 minutes. The mixture was subjected to reaction at room temperature for 30 minutes. After completion of the reaction, the solvent was removed by distillation under reduced pressure. Then, 50 ml of diethyl ether was added to the resulting residue, and the precipitated crystals were collected by filtration and washed with 20 ml of diethyl ether to obtain 2.5 g of methyl 6-(3,4-dibromocyclohexyl)-1-(4-hydroxy-2-methylphenyl)-4-oxo-1,4-dihydronicotinate having a melting point of 197°–200° C.

IR (KBr) $cm^{-1}$: $\nu_{C=O}$ 1730, 1700

EXAMPLE 35

The compounds shown in Table 31 were obtained by hydrolyzing the corresponding methyl esters in the same manner as in Example 32-(4).

TABLE 31

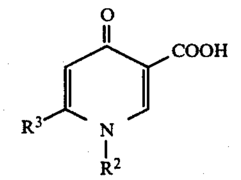

| $R^3$ | $R^2$ | m.p. (°C.) | IR (KBr) $cm^{-1}$: $\nu_{C=O}$ |
|---|---|---|---|
| 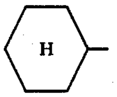 | 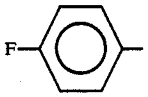 | 235-236 | 1715 |
| 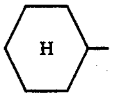 | 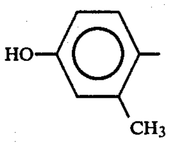 | 175-178 | 1725, 1700 |
| 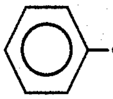 $-CH_2CH_2-$ | 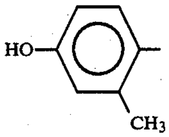 | 226-227 | 1725 |
| 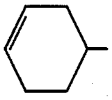 | 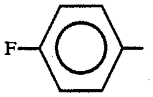 | 182-184 | 1720 |
| 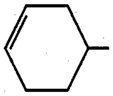 | 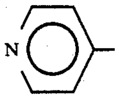 | 171-174 | 1720 |
| 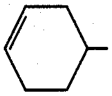 | 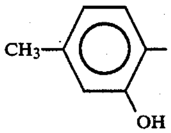 | >250 | 1720, 1710 |
| $CH_3CH=CH-$ (trans) | 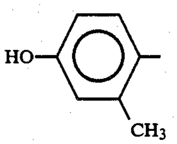 | 245-248 | 1730 |
| 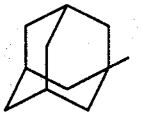 | 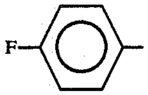 | >280 | 1720 |
| 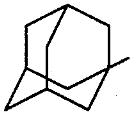 | 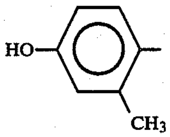 | >280 | 1730, 1710, 1690, 1660 |
| 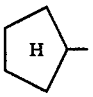 | 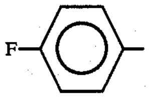 | 172-183 | 1725 |

TABLE 31-continued

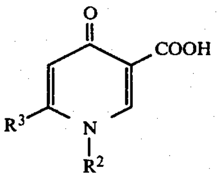

| $R^3$ | $R^2$ | m.p. (°C.) | IR (KBr) $cm^{-1}$: $\nu_{C=O}$ |
|---|---|---|---|
| 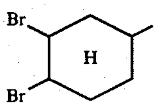 | 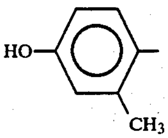 | 183-185 | 1725 |

EXAMPLE 36

(1) In 5 ml of benzene was dissolved 0.7 g of methyl 5-(cyclopenten-1-yl)-3-oxo-4-pentenoate, and 0.6 g of N,N-dimethylformamidodimethylacetal was added thereto. They were reacted at 70° C. for 1.5 hours. The reaction mixture was cooled to room temperature, and 0.44 g of 4-hydroxy-2-methylaniline was added thereto. The resulting mixture was subjected to reaction for addtional 1.5 hours. After completion of the reaction, 5 ml of diethyl ether was added, and the precipitated crystals were collected by filtration, and washed with 5 ml of diethyl ether to obtain 0.7 g of methyl 5-(cyclopenten-1-yl)-2-(4-hydroxy-2-methylphenylaminomethylene)-3-oxo-4-pentenoate having a melting point of 148°-151° C.

IR (KBr) $cm^{-1}$: $\nu_{C=O}$ 1705.

The compounds shown in Table 32 were obtained in the same manner.

TABLE 32

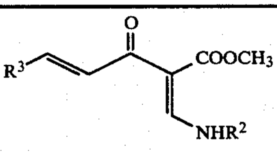

| $R^3$ | $R^2$ | m.p. (°C.) | IR (KBr) $cm^{-1}$: $\nu_{C=O}$ |
|---|---|---|---|
| 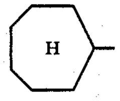 | 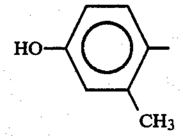 | 161-162 | 1700 |
| 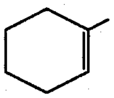 | 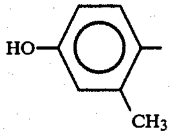 | 145-148 | 1660 |
| 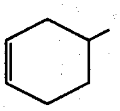 | 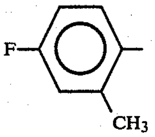 | 168-170 | 1700 |

(2) In 5 ml of N,N-dimethylformamide was dissolved 0.7 g of methyl 5-(cyclopenten-1-yl)-2-(4-hydroxy-2-methylphenylaminomethylene)-3-oxo-4-pentenoate, and they were reacted at 140° C. for 2 hours. After completion of the reaction, the solvent was removed by distillation under reduced pressure, and the residue was purified by a column chromatography (Wako Silica Gel C-200; eluent: chloroform) to obtain an oily substance. This oily substance was dissolved in 10 ml of dioxane, and 0.5 g of 2,3,5,6-tetrachloro-p-benzoquinone was added thereto. They were reacted at 80° C. for 30 minutes. The reaction mixture was cooled to room temperature, and the precipitated crystals were collected by filtration, and washed with 5 ml of dioxane. These crystals were dissolved in a mixture of 5 ml of methanol and 5 ml of a 1N aqueous sodium hydroxide solution, the resulting mixture was subjected to reaction at room temperature for 30 minutes. The reaction mixture was adjusted to a pH of 5.5 with acetic acid and the precipitated crystals were collected by filtration, washed with water, and dried to obtain 1.3 g of 6-(cyclopenten-1-yl)-1-(4-hydroxy-2-methylphenyl)-4-oxo-1,4-dihydronicotinic acid having a melting point of 211°-213° C.

IR (KBr) $cm^{-1}$: $\nu_{C=O}$ 1720, 1700.

The compounds shown in Table 33 were obtained in the same manner.

TABLE 33

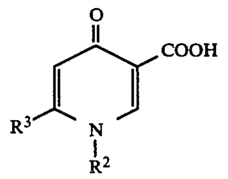

| $R^3$ | $R^2$ | m.p. (°C.) | IR (KBr) $cm^{-1}$: $\nu_{C=O}$ |
|---|---|---|---|
| 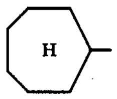 | 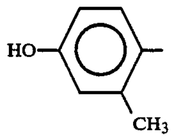 | >250 | 1720, 1710 |
| 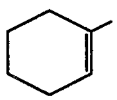 | 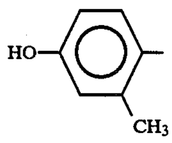 | >250 | 1730, 1725 |
| 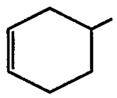 | 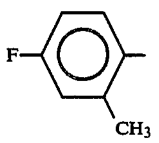 | 162-164 | 1720 |

EXAMPLE 37

In 5 ml of benzene was dissolved 0.3 g of methyl 5-cyclooctyl-3-oxo-4-pentenoate, and 0.3 g of N,N-dimethylformamidodimethylacetal was added thereto. They were reacted at 70° C. for one hour. Then, the reaction mixture was cooled to room temperature, and 0.27 g of 4-hydroxy-2-methylaniline was added thereto. The resulting mixture was subjected to reaction at room temperature for 2 hours. After completion of this reaction, the solvent was removed by distillation under reduced pressure, and the residue was purified by a column chromatography (Wako Silica Gel C-200; eluent: toluene/ethyl acetate (50:1 by volume) mixture). The fraction containing the objective substance was concentrated, and the oily substance thus obtained was dissolved in 5 ml of N,N-dimethylformamide and the resulting mixture was refluxed for 4 hours. After completion of the reaction, the solvent was removed by distillation under reduced pressure, and the residue was purified by a column chromatography (Wako Silica Gel C-200; eluent: chloroform/ethanol (50:1 by volume) mixture). The fraction containing the objective substance was concentrated and the oily substance thus obtained was dissolved in 5 ml of dioxane, and 0.2 g of 2,3,5,6-tetrachloro-p-benzoquinone was added thereto, and they were reacted at 80°-90° C. for 30 minutes. The reaction mixture was cooled to room temperature, and the precipitated crystals were collected by filtration. These crystals were dissolved in 20 ml of chloroform, and after removing the insolubles, the chloroform was removed by distillation under reduced pressure. To the residue was added 5 ml of a 1N aqueous sodium hydroxide solution and 5 ml of methanol, and they were reacted at room temperature for 30 minutes. After the methanol was removed by distillation under reduced pressure, the resulting solution was adjusted to a pH of 6.5 with 2N hydrochloric acid, and the precipitated crystals were collected by filtration, washed with water, and dried to obtain 0.14 g of 6-cyclooctyl-1-(4-hydroxy-2-methylphenyl)-4-oxo-1,4-dihydronicotinic acid having a melting point of 118°-120° C.

IR (KBr) $cm^{-1}$: $\nu_{C=O}$ 1725, 1710.

The compounds shown in Table 34 were obtained in the same manner.

TABLE 34

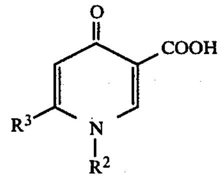

| R³ | R² | m.p. (°C.) | IR (KBr) cm$^{-1}$: $\nu_{C=O}$ |
|---|---|---|---|
| 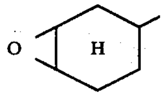 | 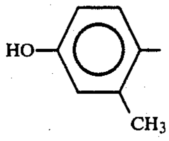 | >270 | 1720 |
| 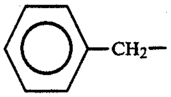 | 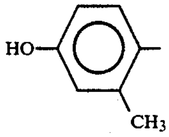 | 229–232 | 1720 |
| 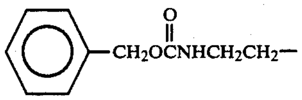 | 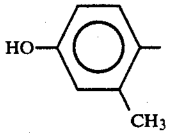 | 102–104 | 1720 |
| 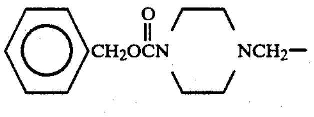 | 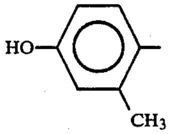 | 115–118 | 1720, 1700 |

TABLE 35

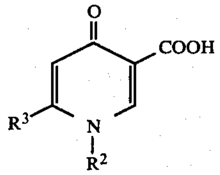

| R³ | R² | m.p. (°C.) | IR (KBr) cm$^{-1}$: $\nu_{C=O}$ |
|---|---|---|---|
| $H_2NCH_2CH_2$— | 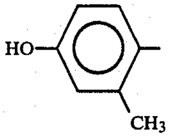 | 220–225 | 1725, 1710, 1690 |
| 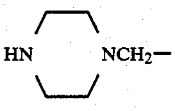 | 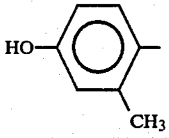 | >250 | 1720 |

EXAMPLE 38

In a mixture of 10 ml of dioxane and 5 ml of water was dissolved 0.15 g of 6-(4-benzyloxycarbonylaminocyclohexyl)-1-(4-hydroxy-2-methylphenyl)-4-oxo-1,4-dihydronicotinic acid, and 0.03 g of 5% by weight palladium carbon was added. The above acid was hydrogenated under atmospheric pressure for 3 hours. The catalyst was removed by filtration and the solvent was then removed by distillation under reduced pressure. To the residue was added 3 ml of diethyl ether, and the precipitated crystals were collected by filtration and washed with 3 ml of diethyl ether to obtain 0.095 g of 6-(4-aminocyclohexyl)-1-(4-hydroxy-2-methylphenyl)-4-oxo-1,4-dihydronicotinic acid having a melting point of 237°–250° C. (decomp.).

IR (KBr) cm$^{-1}$: $\nu_{C=O}$ 1715.

The compounds shown in Table 35 were obtained in the same manner.

EXAMPLE 39

In 15 ml of methanol was dissolved 0.2 g of methyl 6-(4-benzyloxycarbonylaminocyclohexyl)-1-(4-hydroxy-2-methylphenyl)-4-oxo-1,4-dihydronicotinate, and 0.05 g of 5% by weight palladium carbon was added to the resulting solution, and the above ester was hydrogenated under atmospheric pressure for 1.5 hours. Then, the catalyst was removed by filtration, and the solvent was removed by distillation under reduced pressure. To the residue was added 0.4 g of 37% by weight formalin and 0.1 g of formic acid, and they were reacted at 100° C. for 7.5 hours. After completion of this reaction, the solvent was removed by distillation under reduced pressure, and the residue was purified by a column chromatography (Wako Silica Gel C-200; eluent: chloroform/ethanol (3:1 by volume) mixture) to obtain 0.04 g of 6-(4-dimethylaminocyclohexyl)-1-(4-hydroxy-2-methylphenyl)-4-oxo-1,4-dihydronicotinic acid having a melting point of 207°-215° C.

IR (KBr) $cm^{-1}$: $\nu_{C=O}$ 1720.

The compound shown in Table 36 was obtained in the same manner.

TABLE 36

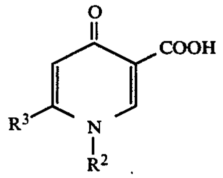

| $R^3$ | $R^2$ | m.p. (°C.) | IR (KBr) $cm^{-1}$: $\nu_{C=O}$ |
|---|---|---|---|
| 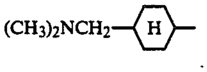 | 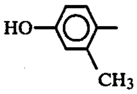 | 177-183 | 1720 |

EXAMPLE 40

(1) In 315 ml of dioxane was dissolved 10.5 g of methyl 1-(4-acetoxy-2-methylphenyl)-6-methyl-4-oxo-1,4-dihydronicotinate under heating, and 4.43 g of selenium dioxide was added thereto. They were reacted at 100° C. for 2 hours. After cooling the reaction mixture, to room temperature, selenium was removed by filtration, and then the solvent was removed by distillation under reduced pressure. The residue was purified by a column chromatography (Wako Silica Gel C-200; eluent: chloroform/ethanol (25:1 by volume) mixture) to obtain 7.9 g of methyl 1-(4-acetoxy-2-methylphenyl)-6-formyl-4-oxo-1,4-dihydronicotinate having a melting point of 216°-217° C.

IR (KBr) $cm^{-1}$: $\nu_{C=O}$ 1760, 1730, 1700 (sh)

(2) To 0.95 g of methyl 1-(4-acetoxy-2-methylphenyl)-6-formyl-4-oxo-1,4-dihydronicotinate was added 5 ml of 6N hydrochloric acid, and they were reacted at 100° C. for one hour. The reaction mixture was cooled to room temperature, and adjusted to a pH of 7.5 with a saturated aqueous sodium hydrogencarbonate solution. Then, 100 ml of acetonitrile was added, and the aqueous layer was saturated with sodium chloride. The organic layer was separated, washed with a saturated aqueous solution of sodium chloride and then dried with anhydrous magnesium sulfate. The solvent was removed by distillation under reduced pressure to obtain 0.6 g of 6-formyl-1-(4-hydroxy-2-methylphenyl)-4-oxo-1,4-dihydronicotinic acid having a melting point of 230°-250° C.

IR (KBr) $cm^{-1}$: $\nu_{C=O}$ 1715.

(3) In 5 ml of methanol was dissolved 0.15 g of 6-formyl-1-(4-hydroxy-2-methylphenyl)-4-oxo-1,4-dihydronicotinic acid, and 0.19 g of ethoxycarbonylmethylenetriphenylphosphorane was added thereto. They were reacted at room temperature for one hour. After completion of the reaction, the solvent was removed by distillation under reduced pressure, and the residue was purified by a column chromatography (Wako Silica Gel C-200; eluent: chloroform/ethanol (50:1 by volume) mixture) to obtain 0.06 g of 6-(2-ethoxycarbonylethenyl)-1-(4-hydroxy-2-methylphenyl)-4-oxo-1,4-dihydronicotinic acid having a melting point of 185°-189° C.

IR (KBr) $cm^{-1}$: $\nu_{C=O}$ 1720, 1705.

(4) To 0.09 g of 6-(2-ethoxycarbonylethenyl)-1-(4-hydroxy-2-methylphenyl)-4-oxo-1,4-dihydronicotinic acid was added 3 ml of 6N hydrochloric acid, and they were reacted at 100° C. for 1.5 hours. After completion of the reaction, the solvent was removed by distillation under reduced pressure, and to the crystals thus formed were added 3 ml of diethyl ether, and the resulting mixture was filtered to obtain 0.08 g of 6-(2-carboxyethenyl)-1-(4-hydroxy-2-methylphenyl)-4-oxo-1,4-dihydronicotinic acid having a melting point of 280° C. or more.

IR (KBr) $cm^{-1}$: $\nu_{C=O}$ 1720.

NMR ($d_6$-DMSO) δ values:

2.0 (3H, s,

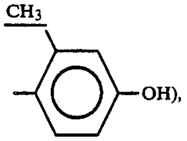

6.33—7.7 (6H, m,

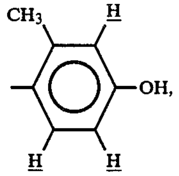

$C_5$—H, —CH=CH—), 8.63 (1H, s, $C_2$—H)

EXAMPLE 41

In 5 ml of methanol was dissolved 0.15 g of 6-formyl-1-(4-hydroxy-2-methylphenyl)-4-oxo-1,4-dihydronionicotinic acid, and 0.056 g of N-aminomorpholine was added thereto. They were reacted at 65° C. for one hour. After completion of this reaction, the solvent was removed by distillation under reduced pressure, and the residue was purified by a column chromatography (Wako Silica Gel C-200; eluent: chloroform) to obtain 0.06 g of 1-(4-hydroxy-2-methylphenyl)-6-(morpholinoiminomethyl)-4-oxo-1,4-dihydronicotinic acid having a melting point of 267°-268° C.

IR (KBr) $cm^{-1}$: $\nu_{C=O}$ 1730.

The compounds shown in Table 37 were obtained in the same manner.

TABLE 37

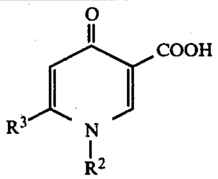

| $-R^3$ | $R^2$ | m.p. (°C.) | IR (KBr) $cm^{-1}$: $\nu_{C=O}$ |
|---|---|---|---|
| 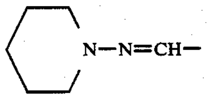 | 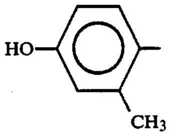 | 249-250 | 1725 |
| 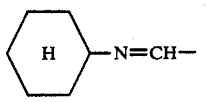 | 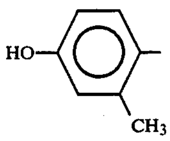 | 193-199 | 1725, 1710, 1695 |
| HO—N=CH— | 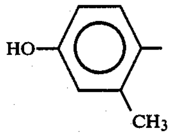 | 268-269 | 1715 |
| $CH_3O$—N=CH— | 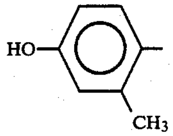 | 269-271 | 1730, 1710 |
| 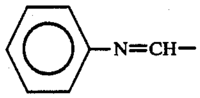 | 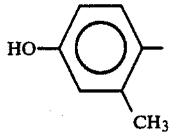 | 264-266 | 1750 |

EXAMPLE 42

In 20 ml of N,N-dimethylformamide was dissolved 2 g of methyl 1-(4-benzyloxy-2-methylphenyl)-6-(2-chloroethyl)-4-oxo-1,4-dihydronicotinate, and 0.9 g of 4-ethyl-2,3-dioxopiperazine-1-sodium was added thereto at 5° C. over 20 minutes, and they were reacted at the same temperature for 30 minutes. After completion of the reaction, the solvent was removed by distillation under reduced pressure, and the residue was dissolved in 20 ml of chloroform, washed successively with 20 ml of water and 20 ml of a saturated aqueous solution of sodium chloride and then dried with anhydrous magnesium sulfate. The solvent was removed by distillation under reduced pressure to obtain an oily substance, and this oily substance was dissolved in a mixture of 10 ml of methanol and 10 ml of a 1N aqueous sodium hydroxide solution. They were reacted at room temperature for 30 minutes. After completion of the reaction, the reaction mixture was adjusted to a pH of 6.0 with acetic acid, and the precipitated crystals were collected by filtration, washed with water, and then dissolved in 10 ml of dioxane and 5 ml of water. Further, 0.2 g of 5% by weight palladium carbon was added thereto, and the resulting mixture was subjected to hydrogenation for 10 hours. After completion of this reaction, the reaction mixture was filtered, and the filtrate was concentrated under reduced pressure to obtain 0.8 g of 6-[2-(4-ethyl-2,3-dioxopiperazin-1-yl)-ethyl]-1-(4-hydroxy-2-methylphenyl)-4-oxo-1,4-dihydronicotinic acid having a melting point of 182°-190° C. (decomp.).

IR (KBr) $cm^{-1}$: $\nu_{C=O}$ 1730.

EXAMPLE 43

In 20 ml of benzene was dissolved 3.0 g of methyl 7-(4-benzyloxycarbonyl-piperazin-1-yl)-3-oxo-4-heptenoate, and 1.2 g of N,N-dimethylformamidodimethylacetal was added thereto. They were reacted at 70° C. for 1.5 hours. The reaction mixture was cooled to room temperature, and 1.0 g of 4-hydroxy-2-methylaniline was added thereto. The resulting mixture was subjected to reaction at the same temperature for 1.5 hours. After completion of this reaction, the precipitated crystals were collected by filtration, and washed with 10 ml of benzene. The crystals thus formed were dissolved in 20 ml of N,N-dimethylformamide, and they were reacted at 140° C. for 3 hours. After completion of the reaction, the reaction mixture was cooled to room temperature, and the solvent was removed by distillation under reduced pressure. The residue was purified by a column chromatography (Wako Silica Gel C-200; eluent: chloroform) to obtain an oily substance. This oily substance was dissolved in 20 ml of dioxane, and 0.7 g of 2,3,5,6-tetrachloro-p-benzoquinone was added thereto, and they were reacted at 80° C. for 30 minutes. After completion of the reaction, the reaction mixture was cooled to room temperature, and the precipitated crystals were collected by filtration, and washed with 10 ml of dioxane. The resulting crystals were dissolved in 10 ml of a 1N aqueous sodium hydroxide solution, and the resulting solution was subjected to reaction at room temperature for 30 minutes. The reaction mixture was adjusted to a pH of 6.0 with acetic acid, and the precipitated crystals were collected by filtration, washed with water, and then dissolved in 10 ml of dioxane and 5 ml of water. Further, 0.2 g of 5% by weight palladium carbon was added thereto. The resulting mixture was subjected to hydrogenation under atmospheric pressure for 2 hours. After completion of the reaction, to the reaction mixture was added 5 ml of 2N hydrochloric acid, and the resulting mixture was filtered, after which the filtrate was concentrated to obtain 0.4 g of 1-(4-hydroxy-2-methylphenyl)-6-[2-(piperazine-1-yl)ethyl]-4-oxo-1,4-dihydronicotinic acid dihydrochloride having a melting point of 140°-148° C.

IR (KBr) $cm^{-1}$: $\nu_{C=O}$ 1720

EXAMPLE 44

In 5 ml of water was suspended 0.15 g of dimethylaminoethyl 1-(4-acetyloxyphenyl)-6-(4-dimethylaminophenyl)-4-oxo-1,4-dihydronicotinate at room temperature, and 0.04 g of L-aspartic acid was added thereto. They were reacted at 60° C. for 30 minutes, and the reaction mixture was cooled to room temperature. The insolubles were removed by filtration, and the solvent was removed by distillation under reduced pressure. The residue was dehydrated azeotropically with toluene and dried to obtain 1.2 g of L-aspartic salt of dimethylaminoethyl 1-(4-acetyloxyphenyl)-6-(4-dimethylaminophenyl)-4-oxo-1,4-dihydronicotinate having a melting point of 144°-147° C.

IR (KBr) $cm^{-1}$: $\nu_{C=O}$ 1760, 1725, 1700

The following compound was obtained in the same manner:

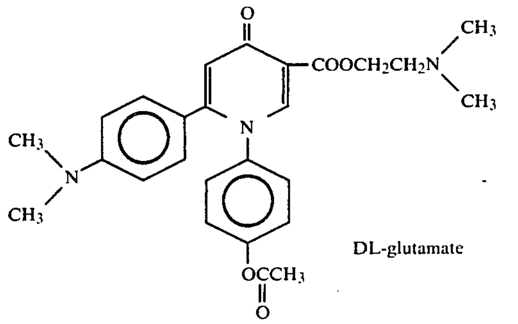

DL-glutamate

Melting point (°C.): 115-118.

IR (KBr) $cm^{-1}$: $\nu_{C=O}$ 1760, 1725, 1700.

EXAMPLE 45

In 20 ml of methylene chloride was dissolved 0.8 g of 1-(4-acetyloxyphenyl)-6-(4-dimethylaminophenyl)-4-oxo-1,4-dihydronicotinic acid, and the resulting solution was cooled to 5° C. To this solution was added dropwise 0.3 g of oxalyl chloride at the same temperature, and they were reacted for one hour. After completion of the reaction, 0.84 g of 1,2-O-isopropylidene glycerin and 0.26 g of triethylamine were added successively at the same temperature, and the resulting mixture was further subjected to reaction for 2 hours. This reaction mixture was introduced into 50 ml of ice water, and the organic layer was separated, washed successively with 50 ml of water and then with 50 ml of a saturated aqueous solution of sodium chloride, and dried with anhydrous magnesium sulfate. The solvent was removed by distillation under reduced pressure, and the residue was suspended in 15 ml of 60% by weight acetic acid. The suspension was subjected to reaction at 60° C. for 3 hours. After completion of this reaction, the solvent was removed by distillation under reduced pressure, and the residue was purified by a column chromatography (Wako Silica Gel C-200; eluent: chloroform/ethanol (15:1 by volume) mixture) to obtain 0.3 g of 2,3-dihydroxypropyl 1-(4-acetyloxyphenyl)-6-dimethylaminophenyl-4-oxo-1,4-dihydronicotinate having a melting point of 145°-147° C.

IR (KBr) $cm^{-1}$: $\nu_{C=O}$ 1760, 1730, 1680.

PREPARATION EXAMPLE 1

With 50 g of 1-pivaloyloxyethyl 6-(4-dimethylaminophenyl)-1-(4-fluorophenyl)-4-oxo-1,4-dihydronicotinate were mixed 49 g of crystalline cellulose, 50 g of corn starch and 1 g of magnesium stearate, and the resulting mixture was tableted into 1,000 flat tablets.

PREPARATION EXAMPLE 2

With 100 ml of 1-pivaloyloxyethyl 6-(4-dimethylaminophenyl)-1-(4-fluorophenyl)-4-oxo-1,4-dihydronicotinate was mixed 50 g of corn starch, and the resulting mixture was encapsulated to from 1,000 capsules.

PREPARATION EXAMPLE 3

In a suitable amount of distilled water for injection were dissolved 200 mg of sodium 1-(2-fluoro-4-hydroxyphenyl)-6-(1-methylindol-5-yl)-4-oxo-1,4-dihydronicotinate and 250 mg of dextrose, and this solution was placed in a 5-ml ampule. After purging with nitrogen, the ampul was sterilized under pressure at 121° C. for 15 minutes to obtain an injection.

What is claimed is:

1. A 4-oxo-1,4-dihydronicotinic acid derivative of the formula:

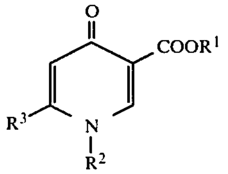

or a salt thereof, wherein $R^1$ is hydrogen or a carboxyl-protecting group;

$R^2$ is a group selected from the group consisting of substituted phenyl and naphthyl, and a substituted and unsubstituted heterocyclic group; and $R^3$ is a haloalkyl, aminoalkyl, or a group selected from the group consisting of substituted or unsubstituted alkenyl, phenylalkenyl, naphthylalkenyl, phenylalkyl, naphthylalkyl, phenylalkadienyl, naphthylalkadienyl, phenylalkynyl, naphthylalkynyl, heterocyclic alkyl, heterocyclic alkenyl, phenyl, naphthyl, cycloalkyl, cycloalkenyl, carboxylic acyl, iminoalkyl, heterocyclic and bridged hydrocarbon; wherein the substituents of said substituted $R^2$ and $R^3$ groups are selected from the group consisting of halogen, alkyl, phenylalkyl, naphthylalkyl, hydroxyl, alkoxy, alkylthio, nitro, cyano, amino, alkylamino, dialkylamino, alkenylamino, carboxyl, carbamoyl, carboxylic acyl, carboxylic acyloxy, carboxylic acylalkyl, carboxylic acylamino, alkoxycarbonyl, aminoalkyl, alkylaminoalkyl, dialkylaminoalkyl, hydroxyalkyl, hydroxyiminoalkyl, alkoxyalkyl, carboxyalkyl, alkoxycarbonylalkyl, sulfoalkyl, sulfo, sulfoxy, sulfamoyl, sulfamoylalkyl, carbamoylalkyl, phenyl, naphthyl, phenylthio, naphthylthio, phenoxy, naphthoxy, oxo, thioxo, mercapto, ureido, hydroxyamino, hydroxyalkylamino, haloalkyl, alkenyl, alkynyl, cycloalkyl, cycloalkadienyl, alkylenedioxy, epoxy, and a heterocyclic group; and wherein said substituents of $R^2$ and $R^3$ may be substituted with at least one substituent selected from the group consisting of halogen, hydroxyl, carboxyl, nitro, alkyl, alkoxy, amino, alkylamino, dialkylamino, phenyl, naphthyl, and carboxylic acyl; and the term heterocyclic of $R^2$ and $R^3$ is thienyl, furyl, pyrrolyl, imidazolyl, pyrazoyl, thiazolyl, isothiazolyl, oxazolyl, isoxazolyl, furazanyl, pyrrolidinyl, pyrrolinyl, imidazolidinyl, imidazolinyl, pyrazolidinyl, pyrazolinyl, oxadiazolyl, thiadiazolyl, triazolyl, tetrazolyl, thiatriazolyl, pyridyl, pyrazinyl, primidinyl, pyridazinyl, piperidinyl, piperazinyl, pyranyl, morpholinyl, pyridin-1-oxide-2-yl, pyridazin-1-oxide-6-yl, quinolin-1-oxide-6-yl, triazinyl, benzothienyl, naphthothienyl, benzofuryl, 2,3-dihydrobenzofuryl, benzothiazolyl, isobenzofuryl, chromenyl, indolidinyl, isoindolyl, indolyl, indazolyl, purinyl, quinolyl, isoquinolyl, 1,2,3,4-tetrahydroquinolyl, 1,2-dihydroquinolyl, phthalazinyl, naphthylidinyl, quinoxalinyl, 1,2,3,4- tetrahydroquinoxalinyl, quinazolinyl, cinnolinyl, pteridinyl, isochromanyl, chromanyl, indolinyl, isoindolinyl, benzoxazolyl, benzomorpholinyl, triazolopyridyl, tetrazolopyridazinyl, tetrazolopyrimidinyl, thiazolopyridazinyl, thiadiazolopyridazinyl, or triazolopyridazinyl; and the term "carboxylic acyl" of $R^3$ is formyl, alkanoyl, benzoyl, p-nitrobenzoyl or heterocyclic carbonyl group.

2. The 4-oxo-1,4-dihydronicotinic acid derivative of claim 1 or a salt thereof, wherein $R^3$ is substituted or unsubstituted phenylalkenyl, naphthylalkenyl, phenylalkadienyl, naphthylalkadienyl, phenylalkynyl, naphthylalkynyl, phenyl, naphthyl, heterocyclic alkenyl, heterocyclic or bridged hydrocarbon.

3. The 4-oxo-1,4-dihydronicotinic acid derivative of claim 1 or a salt thereof, wherein $R^3$ is haloalkyl, aminoalkyl, or a member selected from the group consisting of substituted or unsubstituted alkenyl, cycloalkyl, cycloalkenyl, phenylalkyl, naphthylalkyl, heterocyclic alkyl, iminoalkyl, carboxylic acyl and bridged hydrocarbon group; with the proviso that alkenyl substituted by a phenyl, naphthyl or heterocyclic group is excluded.

4. The 4-oxo-1,4-dihydronicotinic acid derivative of claim 1 or a salt thereof, wherein $R^2$ is substituted phenyl or naphthyl.

5. The 4-oxo-1,4-dihydronicotinic acid derivative of claim 4 or a salt thereof, wherein $R^2$ is phenyl or naphthyl substituted by at least one substituent selected from the group consisting of halogen, hydroxyl and alkyl.

6. The acid derivative of claim 1 being 1-(2-fluoro-4-hydroxylphenyl)-6-(1-methylindol-5-yl)-4-oxo-1,4-dihydronicotinic acid or a salt thereof.

7. The acid derivative of claim 1 wherein $R^2$ is phenyl or naphthyl substituted by at least one substituent selected from the group consisting of halogen, hydroxyl and alkyl; and $R^3$ is heterocyclic alkyl, heterocyclic alkenyl or a heterocyclic group which may be substituted by lower alkyl, said heterocyclic group selected from the group consisting of thienyl, furyl, pyrrolyl, imidazolyl, pyrazolyl, thiazolyl, isothiazolyl, oxazolyl, isoxazolyl, furazanyl, pyrrolidinyl, pyrrolinyl, imidazolidinyl, imidazolinyl, pyrazolidinyl, pyrazolinyl, oxadiazolyl, thiadiazolyl, triazolyl, tetrazolyl, thiatriazolyl, pyridyl, pyrazinyl, pyrimidinyl, pyridazinyl, piperidinyl, piperazinyl, pyranyl, morpholinyl, pyridin-1-oxide-3- or 4-yl, pyridazin-1-oxide-6-yl, quinolin-1-oxide-6-yl, triazinyl, benzothienyl, naphthothienyl, benzofuryl, 2,3-dihydrobenzofuryl, benzothiazolyl, isobenzofuryl, chromenyl, indolidinyl, isoindolyl, indolyl, indazolyl, purinyl, quinolyl, 1,2,3,4-tetrahydroquinolyl, 1,2-dihydroquinolyl, isoquinolyl, phthalazinyl, naphthyridinyl, quinoxalinyl, 1,2,3,4-tetrahydroquinoxalinyl, quinazolinyl, cinnolinyl, pteridinyl, isochromanyl, chromanyl, indolinyl, isoindolinyl, benzoxazolyl, benzomorpholinyl, triazolopyridyl, tetrazolopyridazinyl, tetrazolopyrimidinyl, thiazolopyridazinyl, thiadiazolopyridazinyl and triazolopyridazinyl.

8. An antibacterial agent comprising:

(a) an antibacterially effective amount of a 4-oxo-1,4-dihydronicotinic acid derivative of the formula:

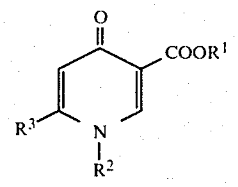

or a salt thereof, wherein $R^1$ is hydrogen or a carboxyl-protecting group;

$R^2$ is a group selected from the group consisting of substituted phenyl or naphthyl, and a substituted or unsubstituted heterocyclic group; and $R^3$ is haloalkyl, aminoalkyl, or a group selected from the group consisting of substituted or unsubstituted alkenyl, phenylalkenyl, naphthylalkenyl, phenylalkyl, naphthylalkyl, phenylalkadienyl, naphthylalkadienyl, phenylalkynyl, naphthylalkynyl, heterocyclic alkyl, heterocyclic alkenyl, phenyl, naphthyl, cycloalkyl, cycloalkenyl, carboxylic acyl, iminoalkyl, heterocyclic and bridged hydrocarbon; wherein the substituents of said substituted $R^2$ and $R^3$ groups are selected from the group consisting of halogen, alkyl, phenylalkyl, naphthylalkyl, hydroxyl, alkoxy, alkylthio, nitro, cyano, amino, alkylamino, dialkylamino, alkenylamino, carboxyl, carbamoyl, carboxylic acyl, carboxylic acyloxy, carboxylic acylalkyl, carboxylic acylamino, alkoxycarbonyl, aminoalkyl, alkylaminoalkyl, dialkylaminoalkyl, hydroxyalkyl, hydroxyiminoalkyl, alkoxyalkyl, carboxyalkyl alkoxycarbonylalkyl, sulfoalkyl, sulfo, sulfoxy, sulfamoyl, sulfamoylalkyl, carbamoylalkyl, phenyl, naphthyl, phenylthio, naphthylthio, phenoxy, naphthoxy, oxo, thioxo, mercapto, ureido, hydroxyamino, hydroxyalkylamino, haloalkyl, alkenyl, alkynyl, cycloalkyl, cycloalkadienyl, alkylenedioxy, epoxy, and a heterocyclic group; and wherein said substituents of $R^2$ and $R^3$ may be substituted with at least one substituent selected from the group consisting of halogen, hydroxyl, carboxyl, nitro, alkyl, alkoxy, amino, alkylamino, dialkylamino, phenyl, naphthyl, and carboxylic acyl; and the term heterocyclic of $R^2$ and $R^3$ is thienyl, furyl, pyrrolyl, imidazolyl, pyrazoyl, thiazolyl, isothiazolyl, oxazolyl, isoxazolyl, furazanyl, pyrrolidinyl, pyrrolinyl, imidazolidinyl, imidazolinyl, pyrazolidinyl, pyrazolinyl, oxadiazolyl, thiadiazolyl, triazolyl, tetrazolyl, thiatriazolyl, pyridyl, pyrazinyl, pyrimidinyl, pyridazinyl, piperidinyl, piperazinyl, pyranyl, morpholinyl, pyridin-1-oxide-2-yl, pyridazin-1-oxide-6-yl, quinolin-1-oxide-6-yl, triazinyl, benzothienyl, naphthothienyl, benzofuryl, 2,3-dihydrobenzofuryl, benzothiazolyl, isobenzofuryl, chromenyl, indolidinyl, isoindolyl, indolyl, indazolyl, purinyl, quinolyl, isoquinolyl, 1,2,3,4-tetrahydroquinolyl, 1,2-dihydroquinolyl, phthalazinyl, naphthylidinyl, quinoxalinyl, 1,2,3,4-tetrahydroquinoxalinyl, quinazolinyl, cinnolinyl, pteridinyl, isochromanyl, chromanyl, indolinyl, isoindolinyl, benzoxazolyl, benzomorpholinyl, triazolopyridyl, tetrazolopyridazinyl, tetrazolopyrimidinyl, thiazolopyridazinyl, thiadiazolopyridazinyl, or triazolopyridazinyl; and the term "carboxylic acyl" in $R^2$ and $R^3$ is formyl, alkanoyl, benzoyl, p-nitrobenzoyl or heterocyclic carbonyl group; and (b) a pharmaceutically acceptable carrier.

9. The antibacterial agent of claim 8 in the form of a tablet, capsule, powder, syrup, granule, suppository, ointment or injection.

10. The antibacterial agent of claim 8 for oral or parenteral administration.

11. The antibacterial agent of claim 8, wherein the antibacterial effective amount of the 4-oxo-1,4-dihydronicotinic acid derivative is a dose per adult of about 0.1 to 100 mg/kg per day.

12. The antibacterial agent of claim 8 wherein the acid derivative is 1-(2-fluoro-4-hydroxyphenyl)-6-(1-methylindol-5-yl)-4-oxo-1,4-dihydronicotinic acid or a salt thereof.

13. The antibacterial agent of claim 8 wherein in the acid derivative $R^1$ is H or a carboxyl-protecting group;

$R^2$ is phenyl or naphthyl substituted by at least one substituent selected from the group consisting of halogen, hydroxyl and alkyl; and $R^3$ is heterocyclic alkyl, heterocyclic alkenyl, or a heterocyclic group which may be substituted by lower alkyl, said heterocyclic group selected from the group consisting of thienyl, furyl, pyrrolyl, imidazolyl, pyrazolyl, thiazolyl, isothiazolyl, oxazolyl, isoxazolyl, furazanyl, pyrrolidinyl, pyrrolidinyl, imidazolidinyl, imidazolinyl, pyrazolidinyl, pyrazolinyl, oxadiazolyl, thiadiazolyl, triazolyl, tetrazolyl, thiatriazolyl, pyridyl, pyrazinyl, pyrimidinyl, pyridazinyl, piperidinyl, piperazinyl, pyranyl, morpholinyl, pyridin-1-oxide-3- or 4-yl, pyridazin-1-oxide-6-yl, quinolin-1-oxide-6-yl, triazinyl, benzothienyl, naphthothienyl, benzofuryl, 2,3-dihydrobenzofuryl, benzothiazolyl, isobenzofuryl, chromenyl, indolidinyl, isoindolyl, indolyl, indazolyl, purinyl, quinolyl, 1,2,3,4-tetrahydroquinolyl, 1,2-dihydroquinolyl, isoquinolyl, phthalazinyl, naphthyridinyl, quinoxalinyl, 1,2,3,4-tetrahydroquinoxalinyl, quinazolinyl, cinnolinyl, pteridinyl, isochromanyl, chromanyl, indolinyl, isoindolinyl, benzoxazolyl, benzomorpholinyl, triazolopyridyl, tetrazolopyridazinyl, tetrazolopyrimidinyl, thiazolopyridazinyl, thiadiazolopyridazinyl and triazolopyridazinyl.

* * * * *